US007740882B2

(12) United States Patent
Ramanathan et al.

(10) Patent No.: US 7,740,882 B2
(45) Date of Patent: *Jun. 22, 2010

(54) ENHANCED ORAL AND TRANSCOMPARTMENTAL DELIVERY OF THERAPEUTIC OR DIAGNOSTIC AGENTS

(76) Inventors: Srinivasan Ramanathan, 850 Maude Ave., Mountain View, CA (US) 94040; Stanley Stein, 6 Rowan Ct., East Brunswick, NJ (US) 08816; Michael Leibowitz, 3 Baron Ct., Manalapan, NJ (US) 07726; Patrick J. Sinko, 2 Country Pl., Lebanon, NJ (US) 08833; Tamara Minko, 2685 Wildberry Ct., Edison, NJ (US) 08817; Gregory C. Williams, 3 Mustang Trail., Warren, NJ (US) 07059; Goubao Zhang, 7699 Palmilla Dr., #3218, San Diego, CA (US) 92122; Xiaoping Zhang, 960 E. Lincoln Ave., Piscataway, NJ (US) 08854; Shahrair Pooyan, 25 Carlton Dr., Monnt Kisco, NY (US) 10549; Seong Hee Park, 23708 BPO, Piscataway, NJ (US) 08854; Bo Qiu, 7 Lake Ave., Apt. 1-B, East Brunswick, NJ (US) 08816; Pankaj Paranjpe, 23601 BPO, Piscataway, NJ (US) 08854

( * ) Notice: Subject to any disclaimer, the term of this patent is extended or adjusted under 35 U.S.C. 154(b) by 992 days.

This patent is subject to a terminal disclaimer.

(21) Appl. No.: 11/170,652

(22) Filed: Jun. 29, 2005

(65) Prior Publication Data

US 2006/0029667 A1 Feb. 9, 2006

Related U.S. Application Data

(63) Continuation of application No. 10/072,657, filed on Feb. 8, 2002, now abandoned.

(60) Provisional application No. 60/267,396, filed on Feb. 8, 2001.

(51) Int. Cl.
*A61K 9/20* (2006.01)
*A61K 38/04* (2006.01)
*A61K 38/00* (2006.01)
*A61K 51/00* (2006.01)

(52) U.S. Cl. .................. 424/465; 530/327; 514/2; 424/1.69

(58) Field of Classification Search .................. None
See application file for complete search history.

(56) References Cited

U.S. PATENT DOCUMENTS

| 6,254,852 B1 * | 7/2001 | Glajch et al. ............... 424/9.52 |
| 6,258,774 B1 | 7/2001 | Stein et al. |

FOREIGN PATENT DOCUMENTS

| WO | WO 99/47173 | * | 9/1999 |
| WO | WO9947173 | | 9/1999 |

OTHER PUBLICATIONS

Balimane, Praveen V. et al. Biochem Biophys Research Comm vol. 250; pp. 246-251 (1998).
Tsuji, Akira et la. Pharm Research vol. 13: (No. 7) pp. 963-9777 (1996).
Borchardt, Ronald T. Journal Controlled Release vol. 62: pp. 231-238 (1999).
Bai, Jane P.F. et al. Journal Pharm Pharmacol vol. 48: pp. 17-21 (1996).
Sinko, Patrick J. et al. Pharm Research vol. 16: (No. 4) pp. 527-533.
Fasano, Alessio Journal Pharm Sci vol. 87: (No. 11) pp. 1351-1356 (1998).
Guo, Ailan et al. Journal Pharmacol Exp Ther vol. 289: (No. 1) pp. 448-454 (1999).
Goodwin, J.T. et al. Journal of Peptide Res vol. 53: pp. 355-369 (1999).

* cited by examiner

*Primary Examiner*—Maury Audet
(74) *Attorney, Agent, or Firm*—Fox Rothschild LLP; Peter J. Butch, III

(57) ABSTRACT

The invention is directed to pharmaceutical compositions and methods for delivery of a therapeutic or diagnostic agent from one bodily compartment to one or more other bodily compartment by administering one of the following conjugates: a polymer having multiple functional groups at least one of which is covalently bound to a therapeutic or diagnostic agent, and at least one cell uptake promoter covalently bound to the therapeutic or diagnostic agent; or a polymer and at least one cell uptake promoter bound thereto; the polymer further comprising multiple functional groups at least one of which is covalently bound a therapeutic or diagnostic agent.

11 Claims, 25 Drawing Sheets

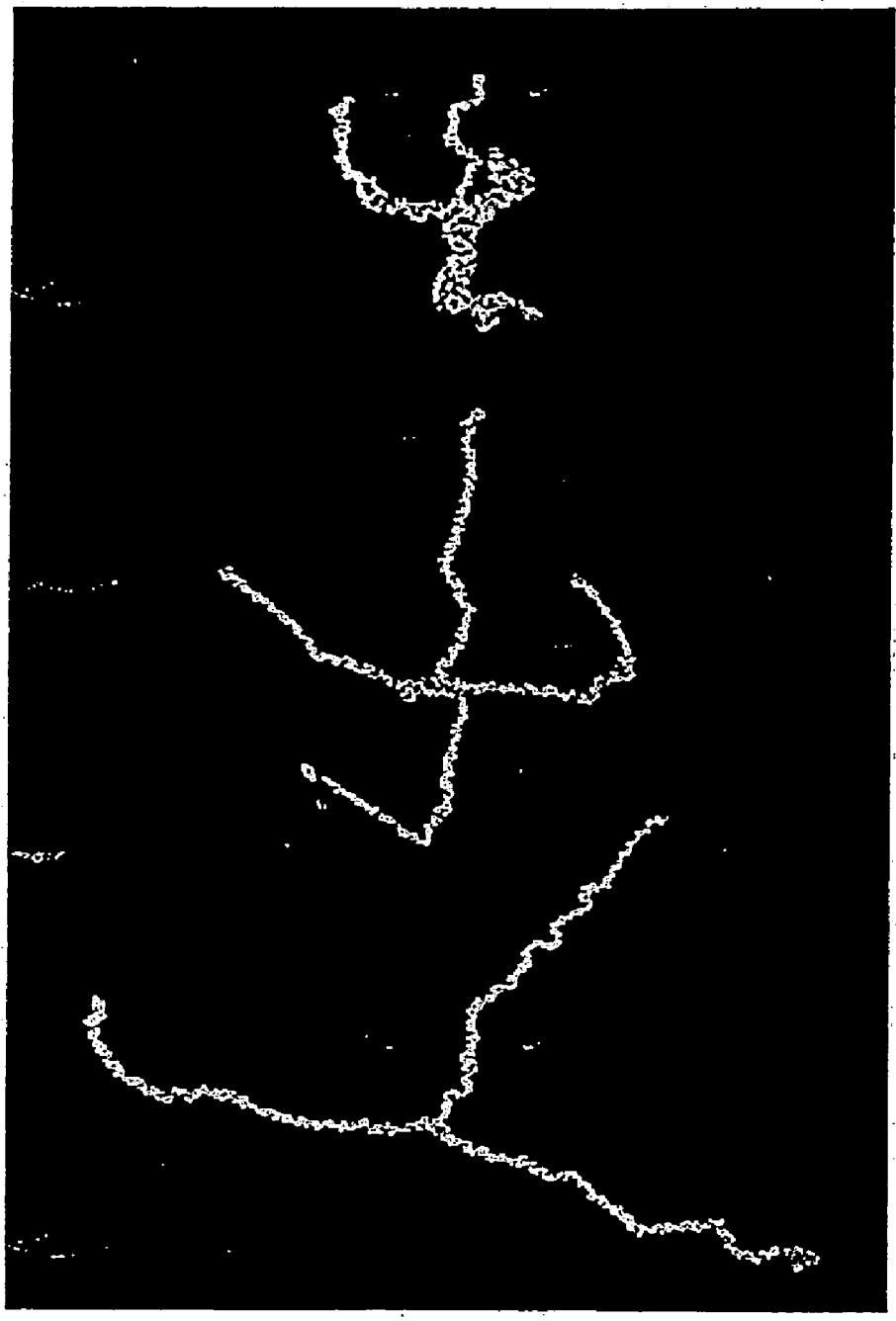

FIGURE 12 A-D

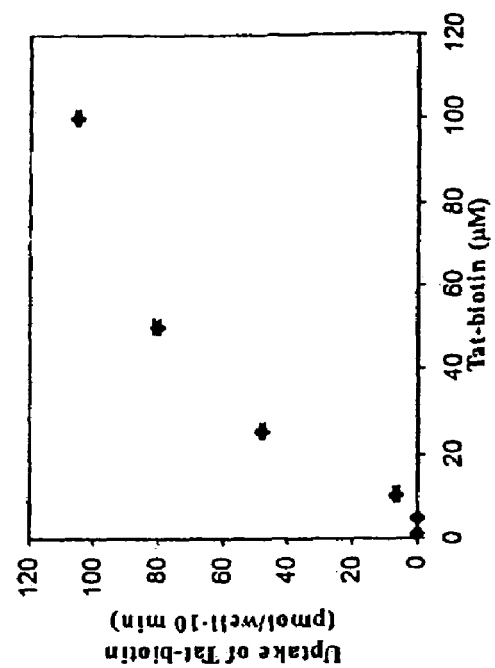
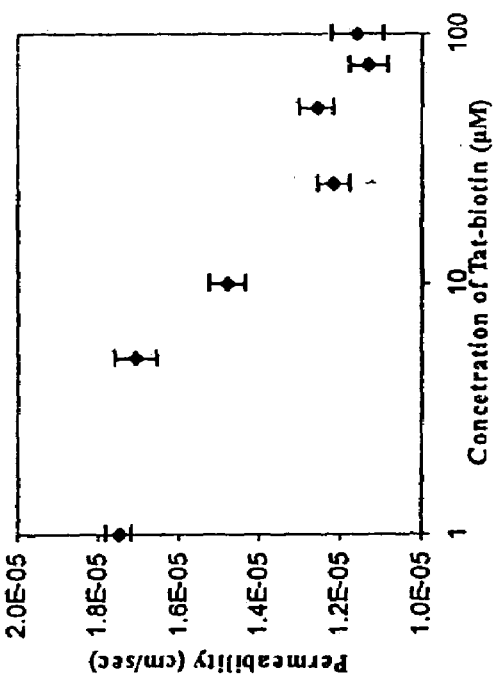
FIGURE 18A-B

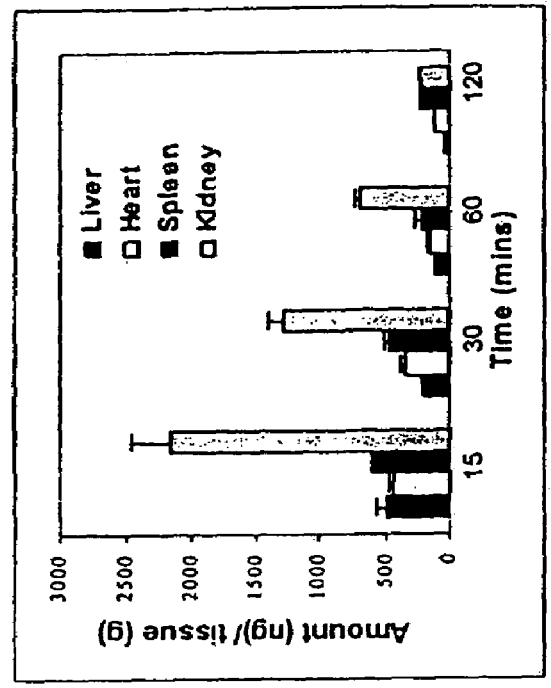
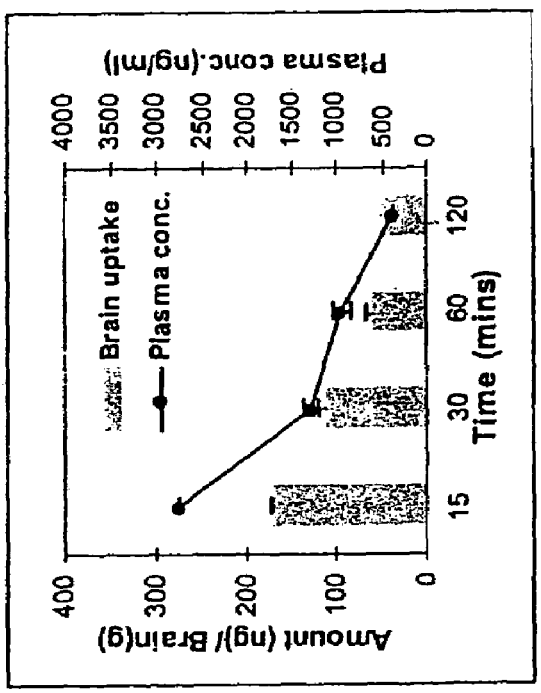
FIGURE 19 A-B

ENHANCED ORAL AND TRANSCOMPARTMENTAL DELIVERY OF THERAPEUTIC OR DIAGNOSTIC AGENTS

CROSS-REFERENCE TO RELATED APPLICATIONS

This application is a continuation application of U.S. Ser. No. 10/072,657, filed Feb. 8, 2002 now abandoned, which claims benefit of priority to Provisional Application Ser. No. 60/267,396, filed Feb. 8, 2001, the disclosures of which are both hereby incorporated by reference in their entireties.

BACKGROUND OF THE INVENTION

Although protein medicines have become more common with the advent of recombinant DNA technology, the pharmaceutical industry still prefers the more traditional small molecule drugs because of the poor pharmacokinetic and other properties (such as absorption, distribution, metabolism and excretion) of proteins as exogenously-administered therapeutic agents. Using proteins as therapeutic drugs, rather than small molecule mimics of these proteins, is certainly more natural and might be preferred if the aforementioned problems can be overcome.

The main problem is that proteins cannot be given orally since they are digested in the gastrointestinal tract. Even if the digestive process is suppressed, proteins alone still cannot transit from the lumen across the epithelial cell barrier into the bloodstream. Intramuscular or subcutaneous injection is most commonly used. Even so, most proteins have a very short half-life (measured in minutes), so the injected protein is present in the patient for only brief periods of time. A solution to this problem would be the development of orally-bioavailable protein drugs. The natural slowness of the digestive process would spread the absorption of the protein drug into the bloodstream over one or more hours, and there would be no significant obstacle to taking a pill several times each day.

The therapeutic efficacy of an orally-administered drug is dictated not only by its pharmacological properties such as potency and selectivity, but also by its biopharmaceutical characteristics such as membrane permeability and metabolic stability. In the past decade, several in-vitro and in-vivo screening techniques have been developed to assess intestinal membrane permeability of therapeutic agents as an indicator of oral absorption (e.g., B. H. Stewart, O. H. Chan, N. Jezyk, and D. Fleisher, 1997, Discrimination between drug candidates using models for evaluation of intestinal absorption, Adv. Drug Del. Res. 23:27-45). The rate of intestinal absorption of a compound is critically influenced by its physicochemical properties, which in turn is dependent on its structural features. Thus, in order to gain insight into the processes involved in the intestinal transport of compounds, elucidation of solute structure/permeability relationships is essential.

The successful oral delivery of peptides and peptidomimetics poses numerous challenges. Low permeability, lack of proteolytic stability, and binding to intestinal components are some of the main factors leading to their low oral bioavailability. The proton linked intestinal oligopeptide transporter (PepT1) facilitates the apical transport of smaller peptides (i.e., typically less than 4 amino acid residues) and some peptide-like drugs (P. V. Balimane, I. Tamai, A. Guo, T. Nakanishi, H. Kitada, F. H. Leibach, A. Tsuji, and P. J. Sinko. Direct evidence for a peptide transporter (PepT1)-mediated uptake of a nonpeptide prodrug valacyclovir, Biochem. Biophys. Res. Commun. 250:246-251 (1998); A. Tsuji and I. Tamai. Carrier-mediated intestinal transport of drugs, Pharm. Res. 13:963-977 (1996); A. Tsuji, I. Tamai, H. Hirooka and T. Terasaki. Beta-lactam antibiotics and transport via the dipeptide carrier system across the intestinal brush-border membrane, Biochem. Pharmacol. 36:565-567 (1987); P. J. Sinko and G. L. Amidon. Characterization of the oral absorption of beta-lactam antibiotics. II. Competitive absorption and peptide carrier specificity, J. Pharm. Sci. 78:723-727 (1989)). PepT1 is a low affinity, high capacity transporter that is involved with the absorption of relatively large doses (i.e., milligram quantities) of drugs such as the cephalosporins and penicillin antibiotics (P. J. Sinko and G. L. Amidon. Characterization of the oral absorption of beta-lactam antibiotics. II. Competitive absorption and peptide carrier specificity, J. Pharm. Sci. 78:723-727 (1989)). Larger peptides such as Leu-enkephalin, a pentapeptide, are not substrates for PepT1 and, therefore, are relatively poorly absorbed (R. T. Borchardt. Optimizing oral absorption of peptides using prodrug strategies. J. Controlled Rel. 62:231-8 (1999)). It is possible to enhance the oral absorption of low permeability, larger peptides by enhancing their stability to proteolytic degradation in the gastrointestinal (GI) tract (D. I. Friedman and G. L. Amidon. Oral absorption of peptides: Influence of pH and inhibitors on the intestinal hydrolysis of leu-enkephalin and analogues, Pharm. Res. 8:93-96 (1991); J. P. Bai, L. L. Chang, and J. H. Guo. Effects of polyacrylic polymers on the luminal proteolysis of peptide drugs in the colon, J. Pharm. Sci. 84:1291-1294 (1995); J. P. Bai, L. L. Chang, and J. H. Guo. Effects of polyacrylic polymers on the degradation of insulin and peptide drugs by chymotrypsin and trypsin, J. Pharm. Pharmacol. 48:17-21 (1996)). However, net peptide absorption remains relatively low if the effective permeability across the intestinal mucosa is also not enhanced. Using citric acid to reduce intestinal pH and minimize trypsin activity and lauroyl carnitine to enhance permeability, a significant enhancement in the oral bioavailability of a large peptide, salmon calcitonin, was achieved (Y-H. Lee, B. A. Perry, S. Labruno, H. S. Lee, W. Stern, L. M. Falzone, and P. J. Sinko. Impact of regional intestinal pH modulation on absorption of peptide drugs: Oral absorption studies of salmon calcitonin in beagle dogs, Pharm. Res. 16(8):1233-1239 (1999); P. J. Sinko, Y-H. Lee, V. Makhey, G. D. Leesman, J. P. Sutyak, H. Yu, B. Perry, C. L. Smith, P. Hu, E. J. Wagner, L. M. Falzone, L. T. McWhorter, J. P. Gilligan, and W. Stern. Biopharmaceutical approaches for developing and assessing oral peptide delivery strategies and systems: In Vitro permeability and In Vivo oral absorption of salmon calcitonin (sCT), Pharm. Res. 16(4):527-533 (1999); P. J. Sinko, C. L. Smith, L. T. McWhorter, W. Stern, E. Wagner, and J. P. Gilligan. Utility of pharmacodynamic measures for assessing the oral bioavailability of peptides. 1. Administration of recombinant salmon calcitonin in rats, J. Pharm. Sci. 84(11): 1374-1378 (1995)).

Another common strategy for improving the intestinal permeability of poorly absorbed compounds is the use of permeation enhancers that transiently modify the barrier properties of biological membranes. Despite initial enthusiasm, the invasive nature of this approach and its associated side-effects have severely hampered the use of absorption enhancers as a viable strategy for improving intestinal permeability (Hochman, J.; Artursson, P. Mechanisms of absorption enhancement and tight junction regulation. J. Controlled Release 1994, 29, 253-267. Citi, S.; Protein kinase inhibitors prevent junction dissociation induced by low extracellular calcium in MDCK epithelial cells. J. Cell Biol. 1992, 117(1), 169-178). Newer agents such as zonulin (Fasano, A.; Novel approaches for oral delivery of macromolecules. J. Pharm. Sci. 1998, 87(11), 1351-1356; Fasano, A. Modulation of intestinal permeability: An innovative method of oral drug delivery for the treatment of inherited and acquired human diseases. Mol Gen. Metabolism 1998, 64, 12-18), that act by receptor-mediated, regio-specific and reversible mechanisms displaying considerably lower cytotoxicity and systemic side-effects, now offer a promising tool in permeability enhancement. However, further studies are still necessary to fully establish their therapeutic utility.

An alternative, non-invasive approach to facilitate intestinal drug absorption is to target specific absorptive transporter systems by chemical modification of drugs to prodrugs and analogues. For instance, it has previously been demonstrated that unlike acyclovir (an anti-herpetic nucleoside), its L-valyl ester prodrug, valacyclovir, is a substrate of the intestinal proton-linked oligopeptide transporter, PepT1 (Guo, A.; Hu, P.; Balimane, P. V.; Leibach, F. H.; Sinko, P. J. Interactions of a nonpeptidic drug, valacyclovir, with the human intestinal peptide transporter (hPepT1) expressed in a mammalian cell line. J. Pharmacol. Exp. Ther. 1999, 289, 448-454; Balimane, P. V.; Tamai, I.; Guo, A.; Nakanishi T.; Kitada, H.; Leibach, F. H.; Tsuji, A.; Sinko, P. J. Direct evidence for peptide transporter (PepT1)-mediated uptake of a nonpeptide prodrug, valacyclovir. Biochem. Biophys. Res. Commun. 1998, 250, 246-251). Due to the low affinity, high capacity nature of PepT1, the interaction between valacyclovir and PepT1 results in a three to four-fold increase in the bioavailability of acyclovir. Despite accepting a wide range of endogenous and exogenous substrates with peptide-like structures, PepT1, facilitates the apical transport of only di- and tri-peptides, which makes it an unsuitable target for transporting larger peptides (>5 amino acid residues) across the intestine (Amidon, G. L.; Lee, H. J. Absorption of peptide and peptidomimetic drugs. Annu. Rev. Pharmacol. Toxicol. 1994, 34, 321-341., Ganaphthy, V.; Leibach, F. H.; Expression and regulation of the taurine transporter in cultured cell lines of human origin. Adv. Exp. Med. Biol. 1994, 359, 51-57.). However, like most currently used strategies for enhancing peptide absorption, it is nonspecific or the mechanisms of action are unknown making it difficult to precisely control the resulting in vivo effect.

The foregoing comments have their counterparts in transport across the blood-brain (and other related) barriers in which endothelial cell tight junctions gate the transport from the lumen of the capillary into the tissue or organ. Various obstacles to the transport of compounds are known and impact the availability of central nervous system active agents to those with the ability to translocate across the capillary endothelium or disrupt the intercellular connections.

The advent of combinatorial chemistry has facilitated potential correlations between intestinal absorption of congeneric series of compounds and iteratively designed newer compounds and their physicochemical properties. Several groups have tried to correlate the Caco-2 cell monolayer permeability of candidate compounds with their structural attributes derived using computational techniques. Parameters such as hydrogen bonding potential, solute lipophilicity, size, charge, and conformation have been shown to be important descriptors of intestinal transport (see, for example, K. Palm, K. Luthman, A-L. Ungell, G. Strandlund, and P. Artursson, Correlation of drug absorption with molecular surface properties, J. Pharm. Sci. 85 (1996) 32-39; C. A. Lipinski, F. Lombardo, B. W. Dominy, and P. J. Feeney, Experimental and computational approaches to estimate solubility and permeability in drug discovery and development settings, Adv. Drug Del. Res. 23 (1997) 3-25; O. S. Gudmundsson, S. D. S Jois, D. G. Vander Velde, T. J. Siahaan, B. Wang, R. T. Borchardt, The effect of conformation on the membrane permeation of coumarinic acid- and phenylpropionic acid-based cyclic prodrugs of opioid peptides, J. Peptide Res. 53 (1999) 383-392; K. Palm, K. Luthman, A-L. Ungell, G. Strandlund, F. Beigi, P. Lundahl, and P. Artursson, Evaluation of dynamic polar molecular surface area as predictor of drug absorption: Comparison with other computational and experimental predictors, J. Med. Chem. 41 (1998) 5382-5392; J. T. Goodwin, B. Mao, T. J. Vidmar, R. A. Conradi, and P. J. Burton, Strategies toward predicting peptide cellular permeability from computed molecular descriptors, J. Peptide Res. 53 (1999) 355-369; and E. G. Chikhale, K-Y. Ng, P. S. Burton, and R. T. Borchardt, Hydrogen bonding potential as a determinant of the in vitro and in situ blood-brain barrier permeability of peptides, Pharm. Res. 11 (1994) 412-419.). Conventional structure-transport analyses have only explored paracellular and passive transcellular routes of diffusion. Very little progress has been made in our understanding on the role of structural descriptors in transporter-mediated absorption processes, primarily due to the non-availability of 3-dimensional structure of membrane transporters.

With regard to the blood-brain barrier (BBB), in vitro models of BBB, the physiological interface regulating drug entry to the central nervous system (CNS), can mimic its in vivo barrier properties. These models offer an alternative to in vivo or in situ animal studies for the evaluation drug transport across the cell monolayers.

In co-pending application Ser. No. 09/044,411, now U.S. Pat. Nos. 6,258,774 and 60/267,396, disulfide-linked conjugates of polymers and therapeutic agents were prepared and shown to enhance intracellular delivery, particularly when a cell uptake promoter such as biotin was bound either to the polymer or to the therapeutic agent.

It is towards the further identification of means to enhance the ability of protein and other drugs to cross various barriers in the body, such as the intestinal mucosa and the blood-brain barrier, and to exhibit acceptable pharmacokinetic and other properties suitable for therapeutic use, that the present invention is directed.

The citation of any reference herein should not be construed as an admission that such reference is available as "Prior Art" to the instant application.

SUMMARY OF THE INVENTION

In its broadest aspect, the invention is directed to a method for delivery of a therapeutic agent or a diagnostic agent from an initial bodily compartment to at least one target bodily compartment, the method carried out by at least administering to the initial bodily compartment an effective transcompartmental delivery promoting amount of one of the following conjugates:

a) a polymer having multiple functional groups at least one of which is covalently bound to a therapeutic or diagnostic agent, and at least one cell uptake promoter is covalently bound to the therapeutic or diagnostic agent; or b) a polymer and at least one cell uptake promoter bound thereto; the polymer further comprising multiple functional groups at least one of which is covalently bound to a therapeutic or diagnostic agent.

The conjugates described above include compounds having the general formulas:

$$(X)_o\text{—}(Y)_m\text{-(linker)}_n \qquad \text{a)}$$

where X is one or more transporter, receptor, binding or targeting ligands, including retro inverso peptides, which may be identical or non-identical;

where Y is one or more of any therapeutic or diagnostic moieties, naturally occurring or artificial, including retro inverso peptides, which may be identical or nonidentical:

where linker comprises polymer with functional groups and provides covalent bonds between linker and Y; and m, n, and o may be any independently varying integers, or more specifically may each independently vary from 1 to about 100: or $$(Y)_m\text{-(linker)}_n\text{-}(X)_o \quad \text{b)}$$

where X is one or more transporter, receptor, binding or targeting ligands, including retro inverso peptides, which may be identical or non-identical;

where Y is one or more of any therapeutic or diagnostic moieties, naturally occurring or artificial, including retro inverso peptides, which may be identical or nonidentical;

where linker comprises polymer with functional groups and provides covalent bonds between linker and X, and/ or Y, or the combination thereof; and m, n, and o may be any independently varying integers, or more specifically may each independently vary from 1 to about 100.

The initial bodily compartment may be an extravascular or an intravascular site, which may be, by way of non-limiting examples, gastrointestinal tract, nasal, pulmonary, ocular, skin, organs, cells, tissues, bodily fluids, circulation, extracellular fluid, cerebrospinal fluid, ventricular fluid, lymphatic fluid, subdermal space, and intradermal space. The target bodily compartment may be, by way of non-limiting example, circulation, the central nervous system, the brain, the eye, or an intracellular environment. The target bodily compartment may be several compartments sequentially traversed by the conjugate of the invention, for example, an orally-delivered conjugate may pass from the initial intestinal luminal compartment across the intestinal epithelium into the circulation, from which it then may pass across the capillary endothelial cells into the central nervous system. In preferred embodiments, the intracellular environment is within an epithelial cell, an endothelial cell, a phagocytic cell, a lymphocyte, a neuron, or a cancer cell. An epithelial cell may be an intestinal cell; a phagocyte may be a macrophage.

The administering may be, for example, parenterally, ocularly, transmucosally or transdermally; transmucosally may be orally, nasally, pulmonarily, vaginally or rectally; parenterally may be intravenous, intra-arterial, intramuscular, intradermal, subcutaneous, intraperitoneal, intraventricular, or intracranial. Preferably, administering is orally.

The linker may be a linear or branched polymer, for example, poly(ethylene glycol), carboxymethylcellulose, dextran, polyvinyl alcohol, polyvinyl pyrrolidone, poly-1,3-dioxolane, poly-1,3,6-trioxane, an amino acid homopolymer, polypropylene oxide, a copolymer of ethylene glycol/propylene glycol, an ethylene/maleic anhydride copolymer, an amino acid copolymer, an amino acid copolymer of polyethylene glycol and an amino acid, a polypropylene oxide/ethylene oxide copolymer, and a polyethylene glycol/thiomalic acid copolymer. Poly(ethylene glycol) is preferred. Branched polyethylene glycol is most preferred. The linker may have a molecular weight ranging from about 200 to about 200,000 Daltons; preferably 2,000 to about 50,000 Daltons, and most preferably about 10,000 Daltons. The multiple thiol compounds are attached to said polymer at an interval, preferably the interval is every about 100 to about 10,000 Daltons; most preferably it is about 300 to about 5,000 Daltons.

The cell uptake promoter, transporter, receptor, binding or targeting ligand may be a vitamin such as, but not limited to, biotin, pantothenate, vitamin B6, or vitamin B12, or analogs thereof. It may also be a carbohydrate for which a transporter exists, such as for glucose and glucose derivatives. It may also be a chemotactic peptide such as a formyl-methionyl peptide. Examples of other peptide targeting agents with a range of size and amino acid order includes the peptide formyl-methionyl-leucyl-phenylalanine (fMLF) peptide and variants thereof which serves as a transport enhancing moiety and increases drug delivery into cells expressing the receptor for that peptide. fMLF is only one example of the class of formyl-methionyl peptides that binds to this receptor. Other examples include other formylmethionyl peptides and proteins capable of binding to the formyl peptide receptor on the surface of phagocytic cells, which also has been reported to bind to certain other, unrelated peptides lacking the formylmethionyl moiety, and these latter peptides unrelated to formylmethionyl peptides but capable of binding to the receptor are fully embraced herein. Other transport enhancing moieties may include Tat-biotin, retro-inverso (RI)-Tat, and RI-TAT-biotin. It may be a chemokine, such as RANTES or IL-2. It may also be a peptide such as Tat, penetratin or VEGF, or a membrane fusion peptide such as gp41. It may also be an enzyme such as neuraminidase. It may be an antibody or an antibody fragment with specific affinity for lymphocyte subpopulations, neurons or other cell types. Examples of such antibodies include antibodies to CD4, which may target helper T-cells, or CD44, which may target ovarian cancer cells. It may also be an antigen or epitope such as influenza virus hemagglutinin. It may also be a hormone such as estrogen, progesterone, LHRH, ACTH or growth hormone. It may also be an adhesion molecule such as ICAM, NCAM or a lectin. It may also be a lipid, such as myristic acid or stearic acid. It may be an oligonucleotide or an antisense oligonucleotide such as aptamers containing 5-(1-pentyl)-2'-deoxyuridine. These are merely non-limiting examples. Any of the cell uptake promoters embraced herein may be provided as a form which is capable of being covalently attached to a polymer or therapeutic agent as described above, such as through a functional or reactive group on the cell uptake promoter or by a chemical modification to provide one.

The functional group on the polymer may be any of a number of moieties which may serve for reacting the various components of the conjugates together, that is, for binding the therapeutic agent and, in the cased in which the cell uptake promoter is bound to the polymer, for binding the cell uptake promoter. Non-limiting examples include a ketone, an ester, a carboxylic acid, an aldehyde, an alcohol, a thiol, or an amine, but these are merely illustrative of the invention. Conjugation of the therapeutic agent and cell uptake promoter may be achieved using bifunctional cross-linking agents, oxidation in the case of two sulfhydral groups forming the cross-link, or any other means for covalently linking the aforementioned components. The functional groups may be activated groups, such as N-ethylmaleimide, which will react directly with a moiety to form a covalent bond. Labile bonds, such as disulfide bonds which are reducible in vivo, are preferred, or enzyme-attackable bonds such as ester bonds. Thioether bonds are also embodied herein. Non-cleavable bonds are also embraced herein, wherein the therapeutic agent is active when covalently bound to the composition of the invention. The bond between the polymer and therapeutic or diagnostic agent, and the bond between the polymer and the cell uptake promoter (in that particular embodiment) are independently labile or non-labile. Where the cell uptake promoter is bound to the therapeutic agent, it may be bound through a labile or non-labile bond. One of skill in the art will readily determine the activity of the therapeutic agent when bound to the polymer and/or cell uptake promoter and construct the composition of the invention to maximize both transcompartmental transport and activity of the therapeutic agent at the desired compartment or compartments. As will be seen below, the lability of the labile bond may be adjusted to maximize delivery to the desired compartment(s) and maximize pharmacological activity of the therapeutic agent at that compartment(s). Moreover, it would be desirable that the polymer contain orthogonal functional groups, such that the number of substituent groups on the polymer can be specified and well controlled during manufacturing. Also, by controlling the addition of appended groups to one or more specific functional groups on the polymer backbone, a monodisperse product, defined as a population of molecules having the same molecular mass, may be readily achieved. By definition, orthogonal refers to chemical groups that can be involved in specific chemical reactions independently of one another. By way of non-limiting examples, when working with peptides, the two most commonly used orthogonal groups are the amino group (—NH$_2$) and the thiol group (—SH). Reagents are available that will react with only amino groups or thiol groups, but not with both. In manufacturing a particular conjugate, one may begin with a scaffold that contains amino and thiol groups, each present in integer numbers. The scaffold may be a peptide, such as Lys-Cys-Cys-Cys. The amino acid Cys has a thiol group, so this peptide can react with 3_molar equivalents of a thiol specific reagent, such as maleimide-PEG to give the product: Lys-Cys(PEG)-Cys(PEG)-Cys (PEG) where by convention the thiol and maleimide groups are understood to be present but not specifically written.

The amino acid Lys has one amino group, but there is one amino group present due to the peptide backbone structure. Therefore, this peptide can react with two equivalents of an amino group specific reagent, such as the N-hydroxysuccinimide activated ester of biotin to give:

(biotin)Lys(biotin)-Cys(PEG)-Cys(PEG)-Cys(PEG)
(SEQ ID NO: 12)

where by convention, the biotin that reacts due to the peptide backbone structure is written at the extreme left and the biotin associated with the Lys is written in parentheses.

Thus, a peptide acting as a scaffold of the formula: (Lys)$_n$-(Cys)$_m$ can be derivatized using two orthogonal reactions to give a product with exactly n+1 copies of the amine-reactive chemical and m copies of the thiol-reactive chemical. By being orthogonal, these 2 reactions can be carried out with either the thiol or the amino reaction first and without regard to any significant improper cross-reaction occuring.

An additional methodology is to use orthogonal protecting groups, such as in the peptide: Cys(t-butyl)-Cys(trityl)-Cys (trityl). All 3 thiol groups in this peptide are blocked from reacting with thiol-specific reagents. However, treatment with reducing agent (e.g. dithiothreitol at pH 8) will remove the t-butyl group to give: Cys-Cys(trityl)-Cys(trityl) which may be reacted with maleimide-PEG to give: Cys(PEG)-Cys (trityl)-Cys(trityl). Then treatment with acid will remove the trityl group to give: Cys(PEG)-Cys-Cys which may be reacted with maleimide-biotin to give: Cys(PEG)-Cys(biotin)-Cys(biotin).

The acid treatment and dithiothreitol treatment may be performed in the reverse order. This peptide still has an amino group available, such as for reacting with amine-reactive fluorescein isothiocyanate to give: (fluorescein)-Cys(PEG)-Cys(biotin)-Cys(biotin). Similarly, the Fmoc and tBoc protecting groups for amines are orthogonal in that the first is base-labile and the second is acid-labile, such as in the peptide: (Fmoc)Lys(tBoc)-Cys(t-butyl)-Cys(trityl) which can accomodate 4 separate reactions.

In a preferred embodiment, multiple cell uptake promoter molecules and multiple therapeutic agent molecules are bound to a branched polymer. In a non-limiting example, a conjugate of the invention with multiple branches and cell uptake promoters on each branch, provide effective delivery. Moreover, combined drug therapy using a composition of the invention may provide a fixed delivery ratio between two or more compounds desirably delivered at a particular ratio, and avoids the problem of varied pharmacokinetics using alternate routes of administration The therapeutic agent may be any pharmaceutically useful compound that may be bound via a functional group thereon to the composition of the invention. Such agents may be therapeutic agents of many types, such as bioactive proteins, peptides, including, but not limited to, retro inverso (RI) peptides, small-molecule compounds, antisense oligonucleotides, and the like. The invention is not limited in any way as to the nature of the therapeutic agent component of the compositions. If no functional group is present on the compound, it may be derivatized to bear one. As noted above, the compositions and methods of the invention provide transcompartmental delivery of such compounds.

The diagnostic agent may be any diagnostically useful compound that may be bound via a functional group thereon to the composition of the invention. Diagnostic moieties having reporter molecules that can be detected by imaging equipment may include radioactive, paramagnetic, fluorescent or radioopaque chemical entities. Specific examples include iodinated sugars that are used as radioopaque agents, and can be appended to linker backbones using ester or other linkages as described above. Additional diagnostic examples include the use of radioactive metal complexes such as Technetium-99m in coordination compounds such as types of, e.g. $^{99m}$Tc-Tetrofosmin or $^{99m}$Tc-Sestamibi, which are used in various types of scintigraphic imaging. Peptidic or other chelating groups can be used to prepare and append chelators that are able to coordinate isotopes of this type.

In a preferred embodiment, the functional groups on the polymer are thiol groups, and in a further preferred embodiment, the therapeutic agent also has a thiol group or is derivatized to have a thiol group. Thus, a preferred conjugate of the invention may be a) a polymer to which multiple thiol compounds each comprising a thiol group are bound, and at least one therapeutic or diagnostic agent comprising a thiol group bound to said polymer through a disulfide bond, and wherein said therapeutic or diagnostic agent comprising a thiol group, further comprises a cell uptake promoter bound thereto; or b) a polymer and a cell uptake promoter conjugated thereto, the polymer having multiple thiol compounds bound thereto, and at least one therapeutic or diagnostic agent comprising a thiol group bound to said polymer through a disulfide bond.

In a preferred embodiment, the multiple thiol groups are attached to said polymer at an interval. Preferably, the interval is about 100 to about 10,000 Daltons. The thiol compound may be, by way of non-limiting example, cysteamine, 1-amino-2-methyl-2-propanethiol, or 1-amino-2-propanethiol.

The cell uptake promoter may be biotin, pantothenate, vitamin B6, vitamin B12, a carbohydrate, a chemokine, a membrane fusion peptide, a lipid, an oligonucleotide, an antisense oligonucleotide, an enzyme, a hormone, an adhesion molecule, a peptide or protein, a formyl-methionyl peptide, a retro inverso peptide or protein, or an antibody molecule or antibody fragment, but it is not so limiting.

The therapeutic or diagnostic agent comprising a thiol group may be a synthetic or naturally-occurring protein or peptide. It may also be a therapeutic agent or a diagnostic agent with or modified to have a thiol group, or be conjugatable to a thiol group, such a modified antisense oligonucleotide or a thioamide-moiety-containing therapeutic agent. It may be a small-molecule compound with a pharmacological activity. It may be a retro-inverso form of a biologically-active peptide, retro-inverso form possessing the same or similar biological activity but possessing other desirable characteristics such as decreased susceptibility to enzymatic attack or metabolic enzymes. In one non-limiting example, the peptide comprises a Tat-inhibitory polypeptide, comprising an amino acid sequence of formula I:

R-Arg-Lys-Lys-Arg-Arg-Gln-Arg-Arg-Arg-X-(biotin)-Cys-NHz (SEQ ID NO:1), and biologically and pharmaceutically acceptable salts thereof, stereo, optical and geometrical isomers thereof where such isomers exist, as well as the pharmaceutically acceptable salts and solvates thereof, wherein R comprises the residue of a carboxylic acid or an acetyl group; and X is a Cys or Lys residue. Examples of the foregoing include N-acetyl-Arg-Lys-Lys-Arg-Arg-Gln-Arg-Arg-Arg-Cys-(biotin)-Cys-NH$_2$ (SEQ ID NO:2)

N-acetyl-Arg-Lys-Lys-Arg-Arg-Gln-Arg-Arg-Arg-Lys-(biotin)-Cys-NH$_2$ (SEQ ID NO:3)

N-acetyl-Arg-Lys-Lys-Arg-Arg-Gln-Arg-Arg-Arg-D-Cys-(biotin)-Cys-NHz (SEQ ID NO:4)

N-acetyl-Arg-Lys-Lys-Arg-Arg-Gln-Arg-Arg-Arg-D-Lys-(biotin)-Cys-NH$_2$ (SEQ ID NO:5)

N-acetyl-Gln-Lys-Lys-Arg-Arg-Gln-Arg-Arg-Arg-D-Lys-(biotin)-Cys-NH$_2$ (SEQ ID NO:6);

N-acetyl-Arg-Lys-Lys-Arg-Arg-Pro-Arg-Arg-Arg-Cys-(biotin-Cys-NH$_2$ (SEQ ID NO:7); or N-acetyl-DCys-DLys-(biotin)-DArg-DArg-DArg-DGln-DArg-DArg-DLys-DLys-DArg-NH$_2$ (SEQ ID NO: 8)

or biologically and pharmaceutically acceptable salts thereof.

The number of copies of the therapeutic or diagnostic agent and the cell uptake promoter on the composition of the invention may be independently varied depending on the initial and target compartments, the desired pharmacokinetics of the product, and other factors. In some cases, the cell uptake promoter is a retro inverso peptide that acts as a transport enhancing moiety which increases therapeutic drug delivery into cells expressing receptors for the retro inverso peptide. In some case, the transport enhancing moiety may also serve as a therapeutic agent itself.

These and other aspects of the invention will be apparent from the consideration of the following figures and detailed description.

BRIEF DESCRIPTION OF THE DRAWINGS

FIG. 18 A-B shows the concentration dependence (18A) and uptake (18B) of Tat-biotin across BBMECs.

FIG. 19 A-B shows the in-vivo uptake by brain of biotin-PEG (FIG. 19A), and the distribution of biotin-PEG to other tissues (FIG. 19B).

DETAILED DESCRIPTION OF THE INVENTION

Figure 1B:
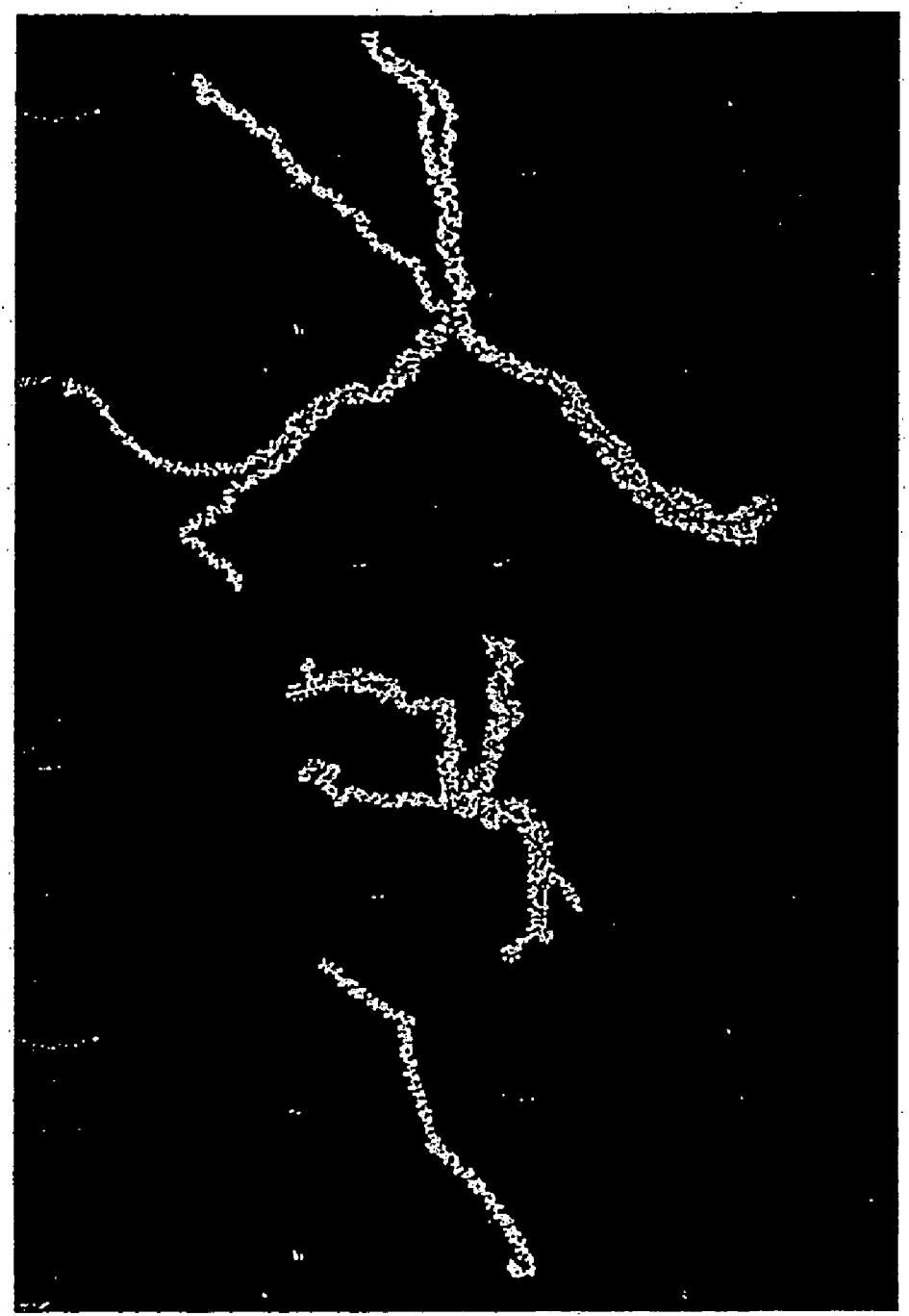
FIG. 1 A-B shows the three-dimensional energy minimized structures of (A) 10 kDa 3-arm, 4-arm, and 8-arm biotin-PEGs; (B) linear (biotin-PEG-3400), 8-arm/10 kDa, and 8-arm/20 kDa biotin-PEGs.

As used herein, a bodily compartment refers to any place or location in or on the body, including extravascular and intravascular sites. Intravascular sites as related to bodily compartments refers to a site within a blood vessel. Extravascular sites or bodily compartments refer to all other areas within or outside of the body not associated directly with a blood vessel, such as but not limited to the gastrointestinal tract, nasal, pulmonary, ocular, skin surface, intradermal, subcutaneous, an organ, cell, tissue, non-blood bodily fluid such as cerebrospinal fluid, lymphatic fluid, etc.

In Ser. No. 09/044,411, now U.S. Pat. No. 6,258,774, incorporated herein by reference, certain of the inventors herein described the utility of an intracellular delivery system for a therapeutic agent comprising a thiol group, using a conjugate of a polymer comprising thiol groups disulfide linked to the therapeutic agent, and a cell uptake promoter such as biotin covalently bound to the therapeutic agent or to the polymer. The cell uptake promoter enhances the intracellular access of the conjugate, and the susceptibility of the disulfide bond between the therapeutic agent and the polymer under reducing conditions within the cell results in release of the therapeutic agent within the cell, where it may exert its desirable effect. The present application is directed to further properties, aspects, compositions and uses of the conjugates therein described, for example, in delivery of therapeutic agents across the intestinal mucosa, across the blood-brain barrier, and enhancement of transport by altering the number of therapeutic agent molecules and/or cell uptake promoter molecules on the polymer, as well as altering the size and branching of the polymer. Further types of bonds, both labile and non-labile, between the polymer, the therapeutic agent and the cell uptake promoter are described. By following the teachings herein with regard to the nature of the polymer, therapeutic agent and cell uptake promoter, one can readily design a conjugate composition capable of delivery from a preselected initial bodily compartment, such as the gastrointestinal tract, to a target bodily compartment, such as the central nervous system. The initial bodily compartment may be accessed through oral or parenteral delivery, such as but not limited to oral, nasal, pulmonary, rectal, vaginal and transdermal; parenteral includes, but is not limited to, intravenous, intraarterial, intramuscular, intradermal, intraocular, subcutaneous, intraperitoneal, intraventricular, intraorbital and intracranial administration.

Applicants have found that the conjugates of the invention are capable of transcytosis across various cell types, in order to deliver the therapeutic agent across one or more compartments. In some cases, the conjugate remains intact after passage and is available for further targeting to a second target cell or organ. In some cases, the therapeutic agent may upon passage across a target cell become partially or fully released from the conjugate, in which it may desirably act locally or within the target compartment, or other locations contiguous with the target compartment. Moreover, several target compartments may be traversed by the compositions of the invention, such as an orally-absorbable compound which passes from the intestinal lumen into the circulation, and then from the circulation across capillary endothelial cells into the central nervous system. Thus, more than one barrier may be traversed by the compositions herein.

Target cells, tissues and organs include, for example, the central nervous system, which requires the conjugate to cross the endothelial cell tight junctions of the brain capillaries. Another target is circulation, for which access is gained from the gastrointestinal tract by delivery of the conjugate across the intestinal epithelium. A preferred embodiment of the invention is the oral delivery into the circulation of protein or peptide therapeutic agents bound to the aforementioned conjugate, administered orally. A second preferred embodiment is the delivery of therapeutic agents across the blood-brain barrier in the form of a conjugate as described above. Other targets include macrophages, a reservoir for HIV infection, and tumor cells. Targeting of particular agents, such as chemotherapeutic agents, to tumor cells is a further embodiment of the present invention.

Moreover, the methods and compositions of the present invention also take advantage of the known selective accumulation in tumors of macromolecular conjugates of chemotherapeutic agents, increasing their cytotoxicity for the tumor and decreasing their systemic toxicity for the host [see Seymour L W, Miyamoto H, Maeda H, Brereton M, Strohalm J, Ulbrich K, Duncan R. Influence of molecular weight on passive tumour accumulation of a soluble macromolecular drug carrier, Eur. J. Cancer 31A(5): 766-770 (1995), and Soyez H, Seymour L W, Schacht E. Macromolecular derivatives of N,N-di-(2-chloroethyl)4-phenylene diamine mustard. 2. In vitro cytotoxicity and in vivo anticancer efficacy, J. Control. Release 57(2): 187-196 (1999)].

Cell uptake promoters include but are not limited to various vitamins and other molecules which are recognized by and are transported by various transporters. These include, but are not limited to, various forms of biotin, various forms of vitamin $B_6$, various forms of vitamin $B_{12}$. Other examples of cell uptake promoters include sugars which are recognized and taken up by specific cell surface transporters. Others include chemotactic peptides such as formyl-methionyl peptides, and in a preferred embodiment, formyl-methionine-leucine-phenylalanine, which specifically targets phagocytic cells. The cell uptake promoter embraces analogs and derivatives of the foregoing and related molecules which are covalently attachable to the polymer, therapeutic or diagnostic agents of the invention. For example, a variety of biotin derivatives with functional or reactive groups are available from Sigma Chemical Co., and a skilled artisan can readily prepare a cell uptake promoter with a functional or reactive group for conjugation, wherein the cell uptake promoter on the conjugate retains its cell uptake promoting activity. As noted herein, multiple copies of the cell uptake promoter may be used on a polymer herein bearing one or more copies of the therapeutic or diagnostic agent, or multiple copies of a therapeutic or diagnostic agent conjugated to a cell uptake promoter may be present on the polymer.

With regard to the cell uptake promoter being chemotactic N-formyl-methionyl peptides that can specifically bind to surface receptors on phagocytic cells, as will be seen below, a single copy of N-formyl-methionine-leucine-phenylalanine (fMLF) covalently linked to a poly(ethylene glycol)-based polymer displayed reduced binding avidity (Kd=190 nM) for differentiated HL-60 cells relative to free fMLF (Kd=28-nM). Increasing the number of fMLF residues attached to a single polymer up to eight results in enhanced avidity for these cells (Kd=0.18 nM), that appears to be independent of whether the polymer backbone is linear or branched. However, no polymer showed enhanced ability to activate phagocytic cells, relative to the free peptide ($EC_{50}$=5 nM), as measured by transient stimulation of release of calcium ions from intracellular stores into the cytoplasm. A polymer bearing four fMLF and four digoxigenin residues showed specific enhancement in binding to differentiated HL-60 cells and mouse peritoneal macrophages in situ relative to a polymer lacking fMLF; no such enhancement was seen in binding to receptor negative lymphocytic Jurkat cells. These results suggest that multiple fMLF residues linked to a drug-delivery polymer can be used to target appended drugs to phagocytic cells with relatively little toxicity due to cellular activation.

Therapeutic agents as defined herein include any prophylactically- or therapeutically-useful compound which is possesses or can be derivatized to possess a functional group through which the therapeutic agent may be conjugated to a polymer of the invention. These include various biologically-active proteins, polypeptides and peptides, which may be naturally-occurring, artificial, and comprise other molecular substituents other than amino acids, including oligonucleotides such as antisense oligonucleotides. While such therapeutic agents are known in the art, several non-limiting examples include growth factors such as insulin, anti-HIV peptides such as Tat inhibitor (see below), erythropoietin, growth hormone, interferon, immunoglobulin, parathyroid hormone, calcitonin, enkephalin, and endorphin. Other therapeutic agents include those which are modified to be able to form a functional or reactive group. Examples of such groups include but are not limited to a thiol (sulfhydryl) group. Such therapeutic agents also include those which possess a thiol group or effectively have a thiol group which may be conjugated to a polymer of the invention, such as a thioamide moiety. Examples of thioamide-moiety-containing therapeutic agents are described in co-pending application Ser. No. 09/621,109, incorporated herein by reference in its entirety. Such compounds include but are not limited to UC781; R82150; HBY097; troviridine; S2720; UC38 and 2',3'-dideoxy-3'-fluoro-4-thiothymidine.

In one embodiment, the conjugates of the invention have been found to be particularly useful for the transport and subsequent delivery of active therapeutic or diagnostic agents across the intestine, the blood-brain barrier, or across both barriers. As will be seen in the examples below, the conjugates of the invention are capable of apical to basal transport in intestinal epithelial cells, and the same directional transport in endothelial cells. These studies demonstrate the utility of the conjugates of the invention for permitting oral delivery of therapeutic or diagnostic agents into the circulation of an animal, as well as the transport of the conjugate from the circulation across the endothelial cell barrier of the brain, and into the central nervous system. These examples demonstrate further the release of the active therapeutic or diagnostic agent from the conjugate through in-vivo reduction of the disulfide bond, and thus the desired pharmacological activity, although the invention is not limited to reducible conjugates and embraces those in which the therapeutic or diagnostic agent is active in a conjugate with or without reduction, enzymatic cleavage or hydrolysis. Of course, access to the endothelium or to other cell types within the body may be provided by oral delivery of the conjugates of the invention, or by other means such as parenteral administration.

Moreover, by adjusting the copy number of both the therapeutic or diagnostic agent and the cell uptake promoter on the selected polymer, and the environment of the reducible disulfide bond between the therapeutic or diagnostic agent and the polymer, the pharmacokinetics, transport and delivery properties of the conjugate may be selected for a particular target cell type, persistence of the conjugate in transit or terminal bodily compartments, particular reducing environment which frees the active therapeutic or diagnostic agent, among other parameters, can be selected to maximize the therapeutic or diagnostic value of the conjugate for its particular utility. The skilled artisan, by the guidance provided herein, will be able to prepare and administer a composition of the invention for the desired end use.

While the preferred embodiments of the invention consist of a therapeutic or diagnostic agent, polymer and cell uptake promoter (the latter bound either to the therapeutic or diagnostic agent or the polymer), and the therapeutic or diagnostic agent reversibly bound to the polymer by way of a labile or non-labile bond, such as but not limited to a disulfide bond, the conjugate may consist of only the therapeutic or diagnostic agent and the polymer, or the therapeutic or diagnostic agent and the cell uptake promoter. Applicants have found enhanced transport of therapeutic agents bound to a polymer of the invention, preferably multiple copies of the therapeutic agent bound to a polymer but it is not necessarily so limited.

Furthermore, the delivery of therapeutic or diagnostic agents into various other desirable target cell types is demonstrated herein, particularly in cancer cells, and in certain cells types for which particular targeting or therapeutic or diagnostic agents is desirable, such as macrophages for the treatment of HIV infection. The targeted delivery and release of the compound within particular cell types provides a therapeutically or diagnostically effective drug at the desired site, rather than elsewhere in the body or at levels too low to be therapeutically or diagnostically effective to achieve the desired therapeutic, diagnostic or prophylactic effect. It has been found that N-formyl-methionyl peptides such as fMLP provide the selective targeting to phagocytic cells such as but not limited to macrophages, to achieve the targeted delivery of therapeutic or diagnostic agents for the aforementioned purposes.

It is a further aspect of the invention to increase the amount of therapeutic or diagnostic agent that can be delivered to a target site by adjusting the number of copies of the therapeutic or diagnostic agent and the number of copies of the cell uptake promoter on the polymer, as well as adjust the molecular weight of the polymer to suit the particular application.

Furthermore, in order to elucidate the structural features that potentially govern the interaction between biotinylated-PEGs and SMVT, or other cellular components, the interactions of linear biotin-PEG-3400 and branched biotin-PEGs differing in size and shape with the human biotin transporter, hSMVT, were determined in CHO cells overexpressing SMVT (CHO/SMVT). Specifically, the branched biotin-PEGs used were 3 arm/10 kDa, 4 arm/10 kDa, 8 arm/10 kDa and 8 arm/20 kDa. The molecular weight of each branched biotin-PEG molecule is evenly distributed among all the arms. Thus, biotin-PEG-8 arm/10 kDa consists of ~1250 monomers in each arm, while biotin-PEG-8 arm/20 kDa consists of ~2500 monomers per arm. Therefore, these molecules vary considerably in their size based on their differential arm-length. In contrast, biotin-PEG-3 arm/10 kDa, and 8 arm/10 kDa would vary in their shape. The uptake of these compounds was evaluated in CHO/hSMVT cells in order to avoid potentially confounding transporters that may be present in Caco-2 cells. Computational techniques were used to explore the influence of conformational flexibility on the physical properties of the substrates. Various structural, geometric and topological descriptors of the compounds were estimated and their correlation with kinetic parameters of transport determined.

The present results suggest that the linear and branched biotin-PEGs of varying shapes and sizes exhibit unique interactions with SMVT with different relative affinities towards SMVT. The maximal affinity of the biotin-PEGs towards SMVT is exhibited within a specific window of topological and structural properties, outside of loss of affinity in paralleled by an increase in the net SMVT-mediated cellular uptake. However, Applicants are not bound by said theory.

In another study using endothelial cells, the following table illustrates the effect of ratio of the number of biotins in a poly(ethylene glycol) molecule on permeability to the blood-brain barrier. Various branched (3 arm/10 kDa, 4 arm/10 kDa, 8 arm/10 kDa and 8 arm/20 kDa) biotin-PEGs were evaluated at a fixed concentration (10 µM) using bovine brain microvessel endothelial cells (BBMECs), an in vitro BBB model. Non-biotinylated PEGs were used in the control studies. Permeabilities of biotin conjugated 3 arm/10 kDa, 4 arm/10 kDa, 8 ar/10 kDa and 8 arm/20 kDa PEGs were 4.8-, 11-, 15- and 19-fold greater, respectively, than the permeabilites of their controls. Transport of the non-biotinylated PEGs were significantly lower (p<0.005) in all cases. There is a positive relationship between the number of branches and the transport of the biotin-PEGs, as shown in Table 1, below.

TABLE 1

| Biotinylated PEGs | $P_{app}$¶ ($\square 10^6$ cm/sec) | Non biotinylated PEGs (Controls) | $P_{app}$¶ ($\square 10^6$ cm/sec) |
|---|---|---|---|
| Biotin-3 arm/10 kDa | 16.8 ± 0.12 | 3 arm/10 kDa | 3.48 ± 0.40 |
| Biotin-4 arm/10 kDa | 19.3 ± 0.15 | 4 arm/10 kDa | 1.78 ± 0.19 |
| Biotin-8 arm/10 kDa | 20.5 ± 0.17 | 8 arm/10 kDa | 1.40 ± 0.39 |
| Biotin-8 arm/20 kDa | 18.0 ± 0.12 | 8 arm/20 kDa | 0.93 ± 0.23 |

¶$P_{app}$: the apparent permeability coefficient (n = 3)

The present invention embraces various ratios between the number of cell uptake promoter molecules and the polymer molecule, including, for example, in branched polymers from one cell uptake promoter per branch to one cell uptake promoter per branched polymer molecule, to linear or branched polymers with repeating cell uptake promoter molecules at intervals. The same parameters apply to the therapeutic or diagnostic agent. As noted herein, the ratios may be readily selected to maximize both delivery at the desired target and amount of therapeutic or diagnostic agent delivered at the target.

In the studies herein, the intestinal transport properties of another large peptide, RI-K(biotin)-Tat9, are characterized. HIV-1 tat protein enters cells and transactivates the HIV-1 long terminal repeat (LTR) when added exogenously to cell culture media (A. D. Frankel and C. O. Pabo. Cellular uptake of the tat protein from human immunodeficiency virus, Cell. 55:1189-1193 (1988); D. A. Mann and A. D. Frankel. Endocytosis and targeting of exogenous HIV-1 Tat protein, EMBO J. 10:1733-1739 (1991)). It has been suggested that adsorptive endocytosis (D. A. Mann and A. D. Frankel. Endocytosis and targeting of exogenous HIV-1 Tat protein, EMBO J. 10:1733-1739 (1991)) or specific cell-surface proteins are involved in the uptake of HIV-1 tat (B. E. Vogel, S. J. Lee, A. Hildebrand, W. Craig, M. D. Pierschbacher, F. Wong-Staal, E. Ruoslahti. A novel integrin specificity exemplified by binding of the alpha v beta 5 integrin to the basic domain of the HIV Tat protein and vitronectin, J. Cell Biol. 121:461-468 (1993); D. A. Brake, C. Debouck, and G. Biesecker. Identification of an Arg-Gly-Asp (RGD) cell adhesion site in human immunodeficiency virus type 1 transactivation protein, tat, J. Cell Biol. 111: 1275-1281 (1990); B. S. Weeks, K. Desai, P. M. Loewenstein, M. E. Klotman, P. E. Klotman, M. Green, and H. K. Kleinman. Identification of a novel cell attachment domain in the HIV-1 Tat protein and its 90-kDa cell surface binding protein, J. Biol. Chem. 268:5279-5284 (1993)). The mechanisms behind the uptake of HIV-1 tat remain controversial, however, the ability of tat to enter cells and to serve as a carrier for heterologous proteins is well established (D. A. Mann and A. D. Frankel. Endocytosis and targeting of exogenous HIV-1 Tat protein, EMBO J. 10:1733-1739 (1991); S. Fawell, J. Seery, Y. Daikh, C. Moore, L. L. Chen, B. Pepinsky, and J. Barsoum. Tat-mediated delivery of heterologous proteins into cells, Proc. Natl. Acad. Sci. USA 91:664-668 (1994); D. C. Anderson, E. Nichols, R. Manger, D. Woodle, M. Barry, A. R. Fritzberg. Tumor cell retention of antibody Fab fragments is enhanced by an attached HIV TAT protein-derived peptide, Biochem. Biophys. Res. Commun. 194:876-884 (1993); R. B. Pepinsky, E. J. Androphy, K. Corina, R. Brown J. Barsoum. Specific inhibition of a human papillomavirus E2 trans-activator by intracellular delivery of its repressor, DNA Cell Biol. 13:1011-1019 (1994)). Chen et al. (L. L. Chen, A. D. Frankel, J. L. Harder, S. Fawell, J. Barsoum, B. Pepinsky. Increased cellular uptake of the human immunodeficiency virus-1 Tat protein after modification with biotin, Anal Biochem. 227:168-175 (1995)) reported a six-fold increase in uptake of tat by the addition of hydrophobic biotin groups. The amount of tat protein that reaches the intracellular compartment, however, is quite low (D. A. Brake, C. Debouck, and G. Biesecker. Identification of an Arg-Gly-Asp (RGD) cell adhesion site in human immunodeficiency virus type 1 transactivation protein, tat, J. Cell Biol. 111: 1275-1281 (1990)). Choudhury et al. (I. Choudhury, J. Wang, A. B. Rabson, S. Stein, S. Pooyan, S. Stein, and M. Leibowitz. Inhibition of HIV-1 replication by a Tat RNA-binding domain peptide analog, J. AIDS Human Retrovir. 17:104-111 (1998)) synthesized a 10-amino acid tat inhibitor, N-acetyl-L-Arg-L-Lys-L-Lys-L-Arg-L-Arg-L-Gln-L-Arg-L-Arg-L-Arg-L-Cys-NH$_2$, denoted Tat9-C, consisting of the 9 amino acid RNA binding domain of Tat linked to a C-terminal cysteine, with its amino terminus acetylated and its carboxy terminus amidated. They showed that Tat9-C, upon S-biotinylation on the cysteine residue (Tat9-C(biotin)) was taken up 30-fold more efficiently by Jurkat cells than was Tat9-C (3% versus 0.1%, respectively). Subsequently, Tat9-K(biotin), which resembles Tat9-C(biotin) except that the cysteine-S-biotin moiety is replaced by lysine-e-N-biotin, was synthesized (I. Choudhury, J. Wang, S. Stein, A. Rabson, and M. J. Leibowitz. Translational effects of peptide antagonists of Tat protein of human immunodeficiency virus type 1, J. Gen. Virol. 80: 777-782 (1999)). Tat9-K(biotin) and Tat9-C(biotin) showed similar ability to compete with Tat protein binding to the TAR domain of viral RNA preventing Tat-dependent gene expression in cultured cells (I. Choudhury, J. Wang, S. Stein, A. Rabson, and M. J. Leibowitz. Translational effects of peptide antagonists of Tat protein of human immunodeficiency virus type 1, J. Gen. Virol. 80: 777-782 (1999)). The replacement of L-amino acids by their D-stereoisomers generally resulted in a reduced ability of Tat9-K(biotin) to bind to the TAR RNA (J. Wang. Development of an HIV-1 Tat antagonist based on TAR RNA as the strategic target. Ph.D. Thesis, Rutgers, The State University of New Jersey, New Brunswick (1997)). The inventors herein found that a retro-inverso (RI) derivative of Tat9-K(biotin), denoted RI-K(biotin)-Tat9, had comparable TAR RNA binding activity to Tat9-K(biotin) (J. Wang, S. Pooyan, M. J. Leibowitz, S. Stein, unpublished results). RI-K(biotin)-Tat9, with its lack of L-amino acids and blocked termini was found to be highly resistant to proteolysis in 10% fetal calf serum. With its reversed order of mirror-image amino acids, it should have steric similarity to Tat9-K(biotin), differing only in the polarity of the underlying peptide backbone. Therefore, RI-K(biotin)-Tat9 was used for some of the studies described herein. In the present study, a mechanistic evaluation of the transport of RI-K(biotin)-Tat9 was performed to determine its suitability for oral administration. The absorptive transport kinetics of RI-K(biotin)-Tat9 was characterized using Caco-2 cell monolayers, a widely used and well established model for investigating drug transport. The specific interactions between RI-K(biotin)-Tat9 and the biotin transporter, SMVT, were determined using CHO cells overexpressing hSMVT (CHO/hSMVT). The current results suggest that a novel strategy for enhancing the intestinal absorption of large peptides may be to add a targeting moiety such as biotin in order to significantly alter its absorption pathway and significantly enhance intestinal permeability.

SMVT, the sodium dependent multivitamin transporter, which transports the water soluble vitamins biotin, pantothenate and lipoic acid, is a protein of 635 amino acids with 12 transmembrane domains. It is expressed in the placenta, intestine, brain, liver, lung, kidney and heart in rats, rabbits and humans. Further, within the intestinal tract, different variants of SMVT (variant I) are also expressed in the duodenum (II), jejunum (II, IV), ileum (II, III), and colon (III). In mammalian cells, the cDNA-induced uptake of physiological substrates biotin, pantothenate and lipoate is electrogenic and sodium dependent with a $Na^+$:vitamin stoichiometry of 2:1 (P. D. Prasad, H. Wang, W. Huang, Y-J. Fei, F. H. Leibach, L. D. Devoe, and V. Ganaphthy. Molecular and functional characterization of the intestinal $Na^+$-dependent multivitamin transporter, Arch. Biochem. Biophys. 366:95-106 (1999)). The physiological aspects involved in the cellular entry of intact HIV-1 Tat protein (86 amino acid residues) and fragments such as residues 1-36 or 36-72 have been extensively documented. However, the specific transport pathways for cellular uptake were not identified. In the present study, a novel Tat inhibitor, RI-K(biotin)-Tat9, with substantial anti-HIV-1 activity was synthesized. As will be seen in the examples below, the absorptive transport of RI-K(biotin)-Tat9 through Caco-2 cell monolayers was found to be concentration dependent and saturable suggesting the involvement of a carrier mediated transport pathway. Inhibition studies implicate the involvement of SMVT. The expression of SMVT in Caco-2 cell monolayers was validated by using a functional assay and known competitive substrates and verified using RT-PCR. The $K_m$ value (11.28 µM) calculated for biotin transport in the current study is consistent with those obtained from human intestinal brush-border membrane vesicles (5.26 µM), colonic epithelial NCM460 cells (19.7 µM), rat small intestine (8.77 µM) and other reports suggesting the involvement of SMVT (T. Y. Ma, D. L. Dyer, and H. M. Said. Human intestinal cell line Caco-2: A useful model for studying the cellular and molecular regulation of biotin uptake, Biochim. Biophys. Acta. 1189: 81-88 (1994); P. D. Prasad, S. Ramamoorthy, F. H. Leibach, and V. Ganaphthy. Characterization of a sodium-dependent vitamin transporter mediating the uptake of pantothenate, biotin and lipoate in human placental choriocarcinoma cells, Placenta 18: 527-533 (1997); H. M. Said, R. Redha, and W. Nylander. A carrier-mediated, Na+ gradient-dependent transport for biotin in human intestinal brush-border membrane vesicles, J. Amer. Physiol. 253: G631-G636 (1987); H. M. Said, R. Redha, W. Nylander. Biotin transport in basolateral membrane vesicles of human intestine, Gasteroenterology 94: 1157-1163 (1988); H. M. Said, A. Ortiz, E. McCloud, D. Dyer, M. P. Moyer, and S. Rubin. Biotin uptake by human colonic epithelial NCM460 cells: a carrier-mediated process with pantothenic acid, Amer. J. Physiol. 275: C1365-C1371 (1998); P. D. Prasad, H. Wang, W. Huang, Y-J. Fei, F. H. Leibach, L. D. Devoe, and V. Ganaphthy. Molecular and functional characterization of the intestinal Na+-dependent multivitamin transporter, Arch. Biochem. Biophys. 366:95-106 (1999)). The absorptive transport of RI-K-Tat9, which lacks biotin, across Caco-2 cell monolayers was modest ($0.8 \times 10^{-7} - 1 \times 10^{-6}$ cm/s) and not mediated by a carrier system, as indicated by its lack of concentration dependence. The chemical modification of RI-K-Tat9 to RI-K(biotin)-Tat9 resulted in a significant increase (3.2-fold; $p<0.001$) in the absorptive permeability (at 1 µM). More importantly, RI-K(biotin)-Tat9 transport was concentration dependent and saturable, suggestive of a carrier mediated transport pathway. The absorptive transport was also temperature dependent with an estimated $E_a$ of 9.11 kcal/mole. It is generally believed that $E_a$ values for active carrier-mediated transport range from 7 to 25 kcal/mole while the $E_a$ value for passive diffusion is less than 4 kcal/mole (I. J. Hidalgo and R. T. Borchardt. Transport of a large neutral amino acid (phenylalanine) in a human intestinal epithelial cell line: Caco-2, Biochim. Biophys. Acta 1028:25-30 (1990)). The $E_a$ value in the present study was more than 2 fold greater than that required for passive diffusion, indicating the active, carrier-mediated transport of RI-K(biotin)-Tat9. The presence of a carrier system was further evident from the significantly larger $P_c$ ($3.22 \times 10^{-6}$ cm/s) component compared to the $P_m$ ($0.57 \times 10^{-6}$ cm/s). The specific interactions between RI-K(biotin)-Tat9 and SMVT were confirmed using hSMVT transfected CHO cells. The presence and expression of SMVT in the CHO/SMVT cells was confirmed by molecular and functional assays. The uptake of RI-K(biotin)-Tat9 and biotin was significantly higher ($p<0.01$) in CHO/hSMVT cells than in the vector transfected CHO/pSPORT cells with similar $K_m$ values (1.00 and 1.39 µM, respectively). It appears that, upon biotinylation, the transport properties of the passively absorbed RI-K-Tat9 were modified, rendering RI-K(biotin)-Tat9 a substrate of SMVT. While Caco-2 cell transport entails passage of compounds across the apical and basolateral membranes, the non-polarized CHO cells represent a model of apical membrane uptake process. The similarity in the $K_m$ values for RI-K(biotin)-Tat9 transport from the Caco-2 (3.27 µM) and CHO/hSMVT (1.00 µM) cell studies suggests that the SMVT protein may be located in the apical domain of Caco-2 cells or there are transporters on both cellular domains. Further studies are required to determine the localization of SMVT.

As mentioned earlier, the Caco-2 cell monolayer transport of RI-K-Tat9 was low ($P_e \sim 0.9 \times 10^{-6}$ cm/s) and the likely result of a passive diffusion process. Upon biotinylation, despite the greater overall permeability of RI-K(biotin)-Tat9, its passive permeability component ($P_m \sim 0.57 \times 10^{-6}$ cm/s) was not statistically different ($p>0.05$) from that of RI-K-Tat9. The apparent lack of increase in the $P_m$ of RI-K(biotin)-Tat9 could be the result of confounding factors, such the presence or absence of other potential transport pathways in the Caco-2 cell model (e.g., active secretory transport) or the realization that transport occurs by means of paths of least resistance in intact systems. The consequent inability of Caco-2 cell monolayers to discriminate between the relative intrinsic contributions of active and passive transport pathways could result in inaccurate estimates of $P_m$. On the other hand, CHO cells, being non-polarized with minimal transporter expression, do not suffer from these drawbacks. Accordingly, in CHO/hSMVT cells, the $J_{max}$ of RI-K(biotin)-Tat9 uptake in CHO/hSMVT cells substantially decreased (from 675.95 to 227.26 pmol/mg protein/10 min) when the $P_m$ component was included in the non-linear regression model. RI-K(biotin)-Tat9 uptake in CHO/pSPORT cells was also significantly higher ($p<0.01$) than RI-K-Tat9 uptake in CHO/hSMVT and CHO/pSPORT (<1 pmol/mg protein/10 min) cells, indicating the cellular uptake enhancing properties of biotin even in the absence of SMVT. This result is consistent with earlier reports on the increased uptake of biotinylated Tat peptides in Jurkat and HL3T1 cells, presumably due to the enhanced hydrophobicity gained by adding biotin to the peptide.

The substrate specificity of SMVT and its specific interaction with RI-K(biotin)-Tat9 were demonstrated by studying the inhibition of RI-K(biotin)-Tat9 transport across Caco-2 cells and uptake in CHO/hSMVT cells in the presence of biotin, biocytin and desthiobiotin. While all three compounds competitively inhibited the Caco-2 cell transport of RI-K(biotin)-Tat9, they also significantly lowered ($p<0.001$) RI-K(biotin)-Tat9 uptake in CHO/hSMVT cells, thereby confirming their specific interaction with SMVT. Previous reports have indicated the requirement of a free carboxyl group on substrates for efficient interactions with SMVT. In these studies, biotin uptake was significantly inhibited by unlabeled biotin, pantothenate, thioctic acid and desthiobiotin compared to biocytin, biotin methyl ester, and thioctic acid amide (the latter three being compounds with a blocked or no carboxyl group). Other reports suggest that the keto group at the second position of the imidazole ring is essential for substrate-SMVT interactions, based on the inability of iminobiotin and diaminobiotin to inhibit biotin uptake. It is believed that SMVT interacts primarily, but not exclusively, with the carboxylic side-chain, which is observed in the known substrates biotin, lipoic acid (containing a valeric carboxyl group) and pantothenic acid (containing a propionic carboxyl group). In the current studies, we observed that RI-K(biotin)-Tat9, a compound in which the valeric carboxyl group is blocked, was indeed a substrate for SMVT. Additionally, we observed that biocytin (biotin conjugated to lysine through an amide bond) substantially inhibited RI-K(biotin)-Tat9 transport across Caco-2 cells. Although RI-K(biotin)-Tat9 does not meet the hypothesized requirements of SMVT substrates as outlined in earlier reports, our results point towards the involvement of SMVT in its absorptive transport. The reason behind this apparent incongruity could be the inconclusive characterization of SMVT substrates in the previous reports. For instance, the requirement of a free carboxyl group on the valeric acid moiety has been emphasized. Yet, pantothenic acid and short chain fatty acids, compounds with non-valeric carboxyl groups, have been reported to significantly inhibit biotin transport. The inhibitory properties of biocytin observed in the present study may well be due to the free carboxyl group on the lysine moiety.

Although the foregoing results show that appending biotin as a targeting moiety may be applied as a novel and useful strategy to enhance the intestinal absorption of large peptides, due to the high affinity, low capacity nature of SMVT (Km values of substrates are typically in the low micromolar range), the resultant saturation of the transporter may limit the dose of drug that can be delivered via this transporter. In order to overcome this drawback, we evaluated the ability of a poly(ethylene glycol) (PEG)-based biopolymeric delivery vehicle to maximize the therapeutic or diagnostic payload of the peptide. As described above, the PEGylated delivery vehicle (or conjugate) was designed to (i) carry multiple copies of a drug, (ii) have an extended half-life in blood or extracellular fluid, (iii) enhance cellular uptake of the drug and subsequently (iv) release the appended drug molecules inside the cell. In a preliminary study, the conjugate, containing multiple copies of an 11-amino acid Tat-peptide with an appended biotin molecule, N-acetyl-Arg-Lys-Lys-Arg-Arg-Gln-Arg-Arg-Arg-Lys(biotin)-Cys-NH$_2$ (SEQ ID NO: 3), displayed 5-fold greater potency (compared to the single copy Tat-peptide) in preventing Tat-dependent gene expression in a cultured cell system (which was not tested for expression of SMVT).

RI refers to the retro-inverso form of a peptide or protein, in which the protein is chemically synthesized from all D-amino acids in a sequence that is of the opposite polarity to that of the natural protein. It is slowly becoming accepted that the retro-inverso form of a peptide most often has the full biological activity inherent to the natural peptide. With improvements in solid phase peptide synthesis and fragment condensation technology, it is becoming possible to extend the size range from peptides to proteins. Since the structure/activity relationships are unique for every protein, some research may be required to modify the retro-inverso protein into a form with suitable biological activity. For example, the charge status of the N- or C-terminus might have to be changed. Use of the retro-inverso form is important to this invention in order to protect against digestion. For proteins or peptides that are naturally resistant to digestion by conditions in the intestinal environment, the naturally-occurring form of the peptide or protein may be used. The invention is not so limited as to the type of therapeutic or diagnostic agent that is the portion of the compound of the invention, only that its desired biological activity is achieved by oral delivery to the body. Other peptide analogs, such as but not limited to peptoids, may also be used in the practice of the present invention.

The transporter provides the enhanced oral uptake and delivery of the compounds of the invention from the lumen of the intestine into the circulation of the animal. As will be seen in the examples herein, which are merely illustrative of the invention and notsoever limiting as to scope, one or more (up to 8) copies of the transporter, the vitamin biotin, were chemically linked to poly(ethylene glycol) (PEG) polymers ranging in molecular weight from 10 to 20 kDa. Carrier-mediated transport, involving the intestinal multivitamin transport protein, was demonstrated. The flux was found to increase with increasing copy number of biotins on PEG. The flux is in the range indicative of good oral bioavailability. In a separate study, a biotin moiety was linked directly to an RI-peptide which in turn was linked (8 copies) to a PEG carrier. Again, the flux was in the range useful for oral bioavailability for both the biotin-linked peptide and its multicopy version on PEG. This biotin-mediated transport can be extended to proteins, as well as to other therapeutic or diagnostic agents, including but not limited to polynucleotides, oligonucleotides, lipids, small-molecule compounds, and other macromolecules and small molecules.

The linker may be used to connect the transporter to the therapeutic or diagnostic agent. By way of example, merely illustrative of the invention but not limiting the scope thereof, PEG polymers containing multiple attachment sites can be appended with one or more biotin groups to yield conjugates capable of being transported across the intestinal epithelia. The linkage of a protein therapeutic or diagnostic agent to this PEG-biotin conjugate still allows the functioning of the biotin transporter, thereby providing delivery of the protein across the intestinal barrier. The protein may be attached to the PEG vehicle by a disulfide bond for eventual release of the protein from its carrier vehicle or by a more biostable bond if the appended PEG-biotin has no deleterious effect on the functioning of that protein drug. However, having a PEG polymer on a therapeutic protein can be useful to extend half-life in vivo by inhibiting renal or hepatic clearance (especially for a small peptide or a small antisense DNA).

As shown in example 1 below, the absorptive transport of the carrier molecule, biotin-PEG-3400 (~3700 Da), and the peptide-loaded carrier molecule PEG:(RI-K(biotin)-Tat9)8 (~27 kDa containing ~8 appended copies of RI-K(biotin)-Tat9), was studied using Caco-2 cell monolayers and CHO cells transfected with human SMVT (hSMVT). The absorptive transport of biotin-PEG-3400 (0.6-100 µM) and PEG:(RI-K(biotin)Tat9)$_8$ (0.1-30 µM) and kinetics of biotin-PEG-3400 inhibition by biotin, biocytin, desthiobiotin (positive controls) were determined using Caco-2 cells. Uptake of biotin-PEG-3400 (0.05-12.5 µM) and PEG:(RI-K(biotin)Tat9)8 (0.003-30 µM) in CHO/hSMVT and CHO/pSPORT (control) was also determined. PEG-3350 and PEG:(RI-K-Tat9)8 were used in the control studies. As shown, biotin-PEG-3400 transport was found to be concentration dependent and saturable in Caco-2 cells (Km=6.61 µM) and CHO/hSMVT cells (Km=1.26 µM) with significant inhibition by various SMVT substrates. PEG:(RI-K(biotin)Tat9)$_8$ also showed carrier-mediated transport kinetics in Caco-2 cells ((Km=6.13 μM) and CHO/hSMVT cells (Km=8.19 μM) cells with a substantially large Jmax (1288.18 pmol/mg protein). Transport of PEG-3350 and PEG:(RI-K-Tat9)$_8$ (controls without biotin) transport was significantly lower (p<0.001) in both cell lines. The studies demonstrate that biotin-PEG-3400 and PEG:(RI-K(biotin)Tat9)$_8$ are substrates of SMVT. The kinetic nature of SMVT can be changed from low to high capacity by using targeted PEG conjugates. Efficient intestinal transport of large molecules such as peptides can be accomplished by targeting the SMVT system.

In example 2 below, the absorptive transport of retro-inverso (RI-) K-Tat9 and RI-K(biotin)-Tat9, novel peptidic inhibitors of the Tat protein of HIV-1, and their interactions with human SMVT (hSMVT), a high affinity, low capacity transporter, were investigated using Caco-2 and transfected Chinese Hamster Ovary (CHO) cells. Following synthesis on a PAL resin using Fmoc chemistry, the transport of RI-K-Tat9 (0.01-25 μM) and RI-K(biotin)-Tat9 (0.1-25 μM) was evaluated across Caco-2 cells. The transport and kinetics of biotin, biocytin and desthiobiotin (positive controls for SMVT) were also determined. Uptake of RI-K-Tat9 and RI-K(biotin)-Tat9 (both 0.1-10 μM) was determined in CHO/hSMVT and CHO/pSPORT (control) cells. The absorptive transport of RI-K-Tat9 was passive, low (Pm~1×10$^{-6}$ cm/sec) and not concentration dependent. RI-K(biotin)-Tat9 permeability was 3.2-fold higher than RI-K-Tat9 demonstrating active (Ea=9.11 kcal/mole), concentration dependent and saturable transport (Km=3.27 μM). RI-K(biotin)-Tat9 uptake in CHO/hSMVT cells (Km=1.0 μM) was ~500-fold greater than RI-K-Tat9 (at 10 μM). RI-K(biotin)-Tat9 transport in Caco-2 and CHO/hSMVT cells was significantly inhibited by known substrates of SMVT including biotin, biocytin, and desthiobiotin. Passive uptake of RI-K(biotin)-Tat9 was significantly greater than RI-K-Tat9 uptake in CHO/pSPORT cells. These studies demonstrate that the structural modification of RI-K-Tat9 to RI-K(biotin)-Tat9 altered its intestinal transport pathway resulting in a significant improvement in its absorptive permeability by enhancing nonspecific passive uptake and carrier-mediated uptake by means of SMVT. The specific interactions between RI-K(biotin)-Tat9 and SMVT show that targeting approaches utilizing transporters such as SMVT substantially improve the oral delivery of large peptides.

In example 3 below, the potential for targeting SMVT for oral delivery of biotinylated-macromolecules was further evaluated. The absorptive transport of the carrier molecule, biotin-PEG-3400 (~3700 Da), and the peptide-loaded carrier molecule PEG:(RI-K(biotin)-Tat9)$_8$ (~27 kDa containing ~8 appended copies of RI-K(biotin)-Tat9), was studied using Caco-2 cell monolayers and CHO cells transfected with human SMVT (hSMVT). The absorptive transport of biotin-PEG-3400 (0.6-100 μM) and PEG:(RI-K(biotin)Tat9)$_8$ (0.1-30 μM) and kinetics of biotin-PEG-3400 inhibition by biotin, biocytin, desthiobiotin (positive controls) were determined using Caco-2 cells. Uptake of biotin-PEG-3400 (0.05-12.5 μM) and PEG:(RI-K(biotin)Tat9)$_8$ (0.003-30 μM) in CHO/hSMVT and CHO/pSPORT (control) was also determined. PEG-3350 and PEG:(RI-K-Tat9)$_8$ were used in the control studies. The studies showed that biotin-PEG-3400 transport was found to be concentration dependent and saturable in Caco-2 cells (Km=6.61 μM) and CHO/hSMVT cells (Km=1.26 μM) with significant inhibition by various SMVT substrates. PEG:(RI-K(biotin)Tat9)$_8$ also showed carrier-mediated transport kinetics in Caco-2 cells ((Km=6.13 μM) and CHO/hSMVT cells (Km=8.19 μM) cells with a substantially large Jmax (1288.18 pmol/mg protein). Transport of PEG-3350 and PEG:(RI-K-Tat9)$_8$ (controls without biotin) trans-port Was significantly lower (p<0.001) in both cell lines. The present results demonstrate that biotin-PEG-3400 and PEG:(RI-K(biotin)Tat9)$_8$ are substrates of SMVT. The kinetic nature of SMVT can be changed from low to high capacity by using targeted PEG conjugates. This general principle that efficient intestinal transport of large molecules such as peptides can be accomplished by targeting the SMVT system may be used as described herein for enhancing oral uptake and delivery of various therapeutic or diagnostic agents.

In example 4 below, the molecular and functional expressions of SMVT in BBMECs were confirmed using RT-PCR and biotin uptake studies, respectively, confirming the utility of in vitro brain microvessel cell culture model to evaluate the SMVT-mediated cellular regulation of biotin conjugated peptide and polymer transport. Upon biotinylating the passively transported RI-K-Tat9, the permeability of RI-K(biotin)-Tat9 was concentration dependent and saturable. The permeability of biotin-PEGs was enhanced by SMVT-mediation. Increased number of branches in the biotin-PEG resulted in greater transport as well as uptake.

In example 5 below, the utility of a chemotactic N-formylmethionyl-bearing peptide was shown to target polymers to macrophages.

EXAMPLE 1

Effect on Transcellular Polymer Transport of Number of Biotin Molecules Per Polymer The following abbreviations are used herein throughout. BOC: Tertiary-butyloxycarbonyl; BOP/HOBt: (benzotriazolyl-oxy-tris-(dimethylamino)-phosphonium/hexafluoro phosphate/hydroxybenzotriazole); DMF: Dimethylformamide; DIEA: N,N-diisopropylethylamine; DTT: Dithiothreitol; Fmoc: Fluorenylmethoxylcarbonyl; RI: retro-inverso; K: lysine; RI-K-Tat9: N-acetyl-D-Lys-D-Arg-D-Arg-D-Arg-D-Gln-D-Arg-D-Arg-D-Lys-D-Lys-D-Arg-NH$_2$ (SEQ ID NO: 9); RI-K(biotin)-Tat9: RI-K-Tat9 with biotin linked to ε-N of N-terminal D-Lys; RI-K(biotin)Tat9-Cys: N-acetyl-D-Cys-D-Lys(ε-biotin)-D-Arg-D-Arg-D-Arg-D-Gln-D-Arg-D-Arg-D-Lys-D-Lys-D-Arg-NH$_2$ (SEQ ID NO: 8); SMVT: Sodium dependent multivitamin transporter; and SPDP: N-succinimidyl-3-(2-pyridylthio) propionate.

Materials The starting materials used on the synthesis of the branched biotin-PEGs (3 arm/10 kDa, 4 arm/10 kDa, 8 arm/10 kDa and 8 arm/20 kDa) consisted of α, ω-NH$_2$-PEGs (Shearwater Polymers, Huntsville, Ala.), which were then biotinylated as detailed below. Biotin-PEG-3400 was purchased as α, ω-Biotin-PEG-NHS (PEG M.W.=3400) (Shearwater Polymers, Huntsville, Ala.) and tritiated (specific radioactivity 1.542 mCi/mmol) as described below. The human sodium dependent multivitamin transporter, hSMVT, subcloned in the mammalian expression vector, pSPORT, was kindly provided by Dr. Puttur D. Prasad (Medical College of Georgia, Augusta, Ga.). All medium components and reagents for cell culture were obtained from Gibco Life Technologies, Inc. (Grand Island, N.Y.). All other chemicals were received from Sigma Chemical Co. (St. Louis, Mo.) or Fisher Scientific (Fair Lawn, N.J.) and used as received.

Synthesis of Branched biotin-PEG compounds Branched NH$_2$-PEGs (NH$_2$-PEG-3 arm/10 kDa, NH$_2$-PEG4 arm/10 kDa, NH$_2$-PEG-8 arm/10 kDa, NH$_2$-PEG-8 arm/20 kDa) were dissolved in 0.5 ml of 50 mM Na$_2$CO$_3$ (pH 9.0). To these solutions, 1.0 equivalent of biotin-NHS (Pierce, Rockford, Ill.) was added and the reaction stirred overnight. Fluorescamine assays [S. Udenfriend, S. Stein, P. Bohlen, W. Dairman, W. Leimgruber, M. Weigele. Fluorescamine, a new reagent for assay of amino acids, peptides, protein and primary amines in the picomole range, Science, 178 (1972) 871-872] resulted in 90% reduction in fluorescence indicating that 90% of the amino groups on PEG had reacted with biotin. The resultant product was purified by ultracentrifugation using an Amicon filter (Amicon Inc., Beverly, Mass.) with a molecular weight cut-off ~3000 Da. The branched biotin-PEGs were then dissolved in 0.5 ml DMF and remaining 10% of amino groups were reacted with [$^3$H]-acetic anhydride using 3 equivalent BOP/HOBt as coupling reagents. Finally, the product was ether precipitated and dried under air. According to the manufacturer, the molecular weight of each biotin-PEG molecule was evenly distributed between all the arms.

Biotin-PEG-3400 Tritiation The succinimide ester of biotin-PEG-3400 (biotin-PEG-CO$_2$-NHS, 15.6 µmol) (Shearwater Polymers, Inc.) dissolved in 4 ml sodium carbonate (50 mM, pH 9.0) was added to 10-equivalent diaminobutane (1.64 mmol) and the mixture stirred overnight. Following aqueous dilution (30 ml), the resultant product was with extracted thrice with methylene chloride (30 ml) and reduced to 0.5 ml using a rotary evaporator. Subsequently, it was precipitated with ethyl ether, purified using HPLC with SEC column and dried under speed vacuum. It was then dissolved in 0.5 ml DMF and reacted with [$^3$H]acetic anhydride using BOP/HOBt as coupling reagents. The product was ether precipitated and dried under air.

Cell Culture Protocols The CHO cell line was obtained from American Type Culture Collection (ATCC) (Rockville, Md.) at passage 4. Cells were maintained in Dulbecco's Modified Eagle's Medium (DMEM) containing 10% heat-inactivated fetal bovine serum, 1% nonessential amino acids, penicillin (100 U/ml), and streptomycin (100 mg/ml), in an atmosphere of 95% air and 5% CO$_2$ at 37° C. Culture medium was changed every other day and cells were passed every 2-3 days by trypsinizing with 0.05% trypsin and 0.53 mM EDTA at 37° C. for 2 minutes. After harvesting at 90% confluency (determined using a Zeiss Telaval 31 inverse phase contrast microscope), cells were seeded at a density of 3×10$^5$ cells/well in 12-well culture plates and incubated at 37° C. for 24 hours (Corning-Costar, Cambridge, Mass.). For cell density determinations, the cell suspensions grown in various T-flasks were combined into a centrifuge tube and shaken gently for even distribution. Using aseptic technique, the cell suspension were stained with trypan blue, counted using a hemacytometer, and then appropriately diluted with fresh media (in a centrifuge tube) to the target density. Approximately 24 hours post-seeding, the cells were transfected with the human sodium dependent multivitamin transporter, hSMVT, subcloned in the mammalian expression vector, pSPORT. The cells were transfected with hSMVT or pSPORT (vector control) by Lipofectamine™ according to the manufacturer's instructions (Life Technologies). For each well, 1 µg of DNA was mixed gently with 200 µl of serum-free medium and 10 µg of Lipofectamine™ reagent. The mixture was incubated at room temperature for 15 minutes and transferred to each well. Then 0.8 ml of serum-free medium was subsequently added to the mixture. After a 5-hour incubation at 37° C., the transfection mixture was removed and replaced with 1 ml of complete growth containing 10% FBS.

CHO Cell Uptake Studies CHO cells transiently transfected with hSMVT (CHO/hSMVT) were washed twice with 25 mM uptake buffer, containing 25 mM Hepes/Tris pH 7.5, 140 mM NaCl, 5.4 mM KCl, 1.8 CaCl$_2$, 0.8 mM MgSO$_4$ and 5 mM glucose, approximately 48 hours post-transfection. Subsequently, the cells were incubated with the permeant at 37° C. for 10 minutes. Uptake was stopped by washing the cells thrice with ice-cold buffer. Non-specific uptake was measured in parallel experiments with the control pSPORT vector-transfected CHO cells. Finally, the cells were solubilized by 0.1% v/v Triton X-100, and 0.6 ml was used for scintillation counting. From the remaining volume, 10 µl of solution was taken from each well and protein concentration was determined using the Bio-Rad reagent according to the Bradford technique [M. Bradford, A rapid and sensitive method of quantitation of microgram quantities of protein utilizing the principle of protein-dye binding, Anal. Biochem. 72 (1976) 248]. Bovine serum albumin was used as the standard.

Biotin-PEG-3400 Experiments The uptake of biotin-PEG-3400 uptake in CHO/hSMVT cells was studied in the concentration range of 0.05-12.5 µM with simultaneous determinations in control CHO/pSPORT cells. Uptake of PEG-3350 (0.05-10 µM) in CHO/hSMVT cells was evaluated in the control studies. Further, uptake of biotin-PEG-3400 (0.1 µM) was determined in CHO/hSMVT cells in the presence of putative substrates of SMVT such as biotin, pantothenic acid, desthiobiotin, biocytin, and a transport competitor, biotin-PEG-biotin (50 µM).

Branched Biotin-PEG Experiments The uptake of biotin-PEG-3 arm/10 kDa, biotin-PEG4 arm/10 kDa, biotin-PEG-8 arm/10 kDa and biotin-PEG-8 arm/20 kDa in CHO/hSMVT cells was determined in the concentration range of 0.5-100 µM. Parallel uptake experiments were performed using CHO/pSPORT control cells. Uptake of NH$_2$-PEG-3 arm/10 kDa, NH$_2$-PEG-4 arm/10 kDa, NH$_2$-PEG-8 arm/10 kDa and NH$_2$-PEG-8 arm/20 kDa in CHO/hSMVT cells was determined in the control studies.

Molecular Modeling of branched biotin-PEG Multiconformer Ensembles In order to investigate the role of topological, geometric and structural properties of the various biotin-PEG molecules on the interaction with SMVT, molecular modeling studies were performed using Molecular Operating Environment (MOE) software program (Chemical Computing Group, Montreal, Calif.). The linear and branched biotin-PEGs used in this study were constructed from "SMILES" strings and energy-minimized using steepest descent and truncated Newton conjugate gradient minimization protocols to obtain reasonable low energy starting conformations. Conformational analyses were performed by molecular mechanics force field (MMFF94) using a hybrid Monte Carlo randomization program entailing four 10,000-step conformational searches. The in vacuo conformers generated were then energy-minimized using truncated Newton conjugate gradient minimization with a convergence criterion of 0.01 kcal/mol. Using the QSAR-descriptor feature of MOE, simple and valence delta values of Kier and Hall molecular connectivity indices $^0\chi$, $^0\chi^v$, $^1\chi$ and $^1\chi^v$, molecular refractivity and van der Waals volume were calculated to obtain information relating to global volume of the biotin PEGs. The van der Waals surface area of the compounds studied was also determined. In order to understand shape attributes of the compounds, kappa shape indices. $^1\kappa$, $^2\kappa$, and $^3\kappa$, that encode information relating to molecular cyclicity, spatial atomic density, and centrality of branching, respectively, were estimated. Typically, these indices are greater for linear or non-cyclic structures. The relative flexibility of biotin-PEGs was determined using the Kierflex index. Finally, the relationship between the computed molecular descriptors and the kinetic parameters of CHO/hSMVT cell uptake was then determined.

Figure 2:
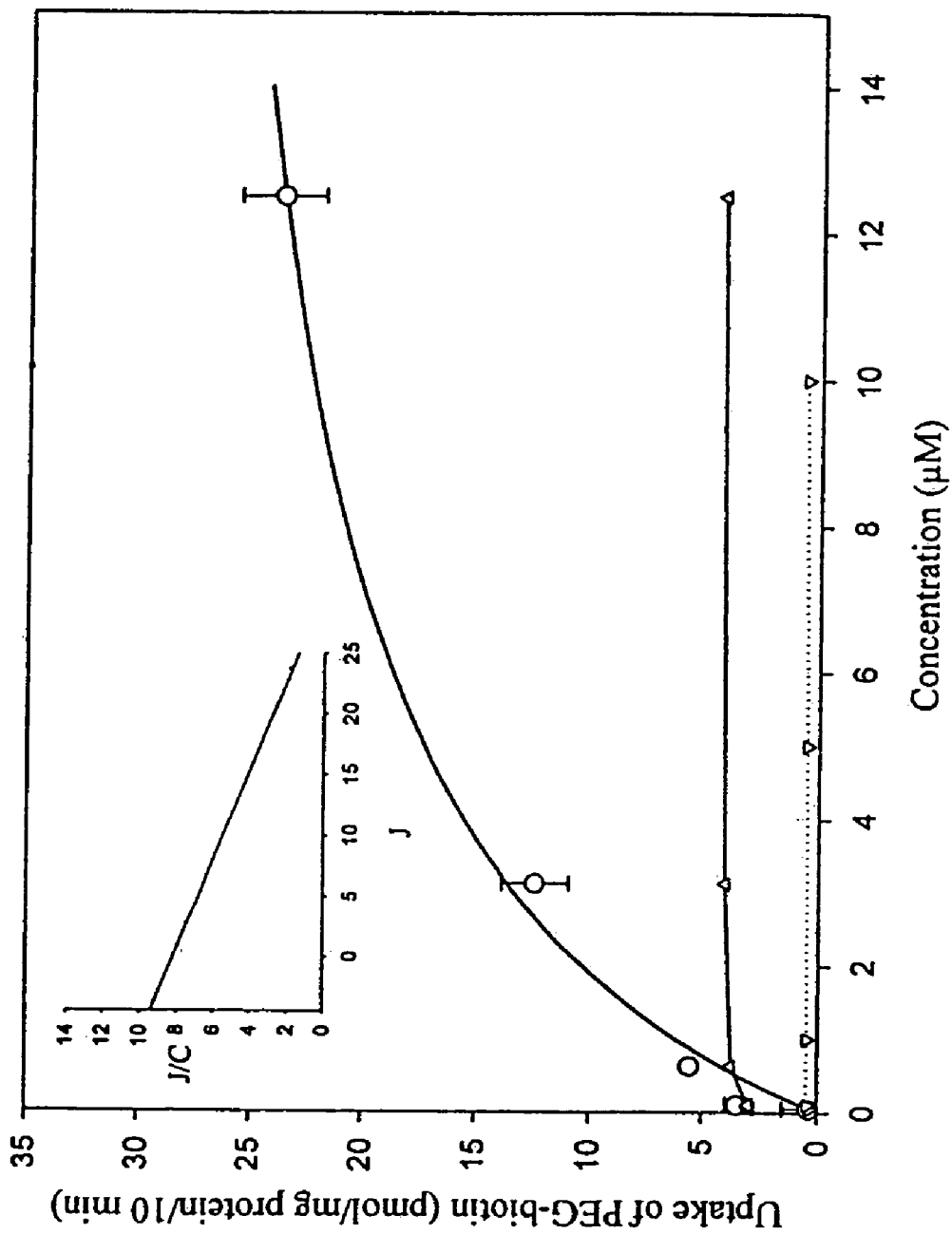
FIG. 2 shows the uptake of biotin-PEG-3400 and PEG-3350 in CHO/hSMVT and CHO/pSPORT cells. The inset shows the transformation of the uptake data into an Eadie-Hofstee plot.

Results of Biotin-PEG-3400 Transport Studies The uptake of biotin-PEG-3400 in CHO/hSMVT cells was concentration dependent and saturable (FIG. 2) with estimated K$_m$ and J$_{max}$ values of 1.26±1.01 µM and 23.46±5.04 pmol/mg protein/10 min, respectively. Transformation of the uptake data into an Eadie-Hofstee plot (r=0.9047) (FIG. 2 inset) indicated that the kinetics of biotin-PEG-3400 matched a single saturable carrier model. Biotin-PEG-3400 uptake was significantly lower (p<0.01) in the control CHO/pSPORT cells (4.22 pmol/mg protein/10 min) compared to CHO/hSMVT cells, but higher than PEG-3350 uptake in CHO/hSMVT cells (<1 pmol/mg protein/10 min) (FIG. 2).

Figure 3:
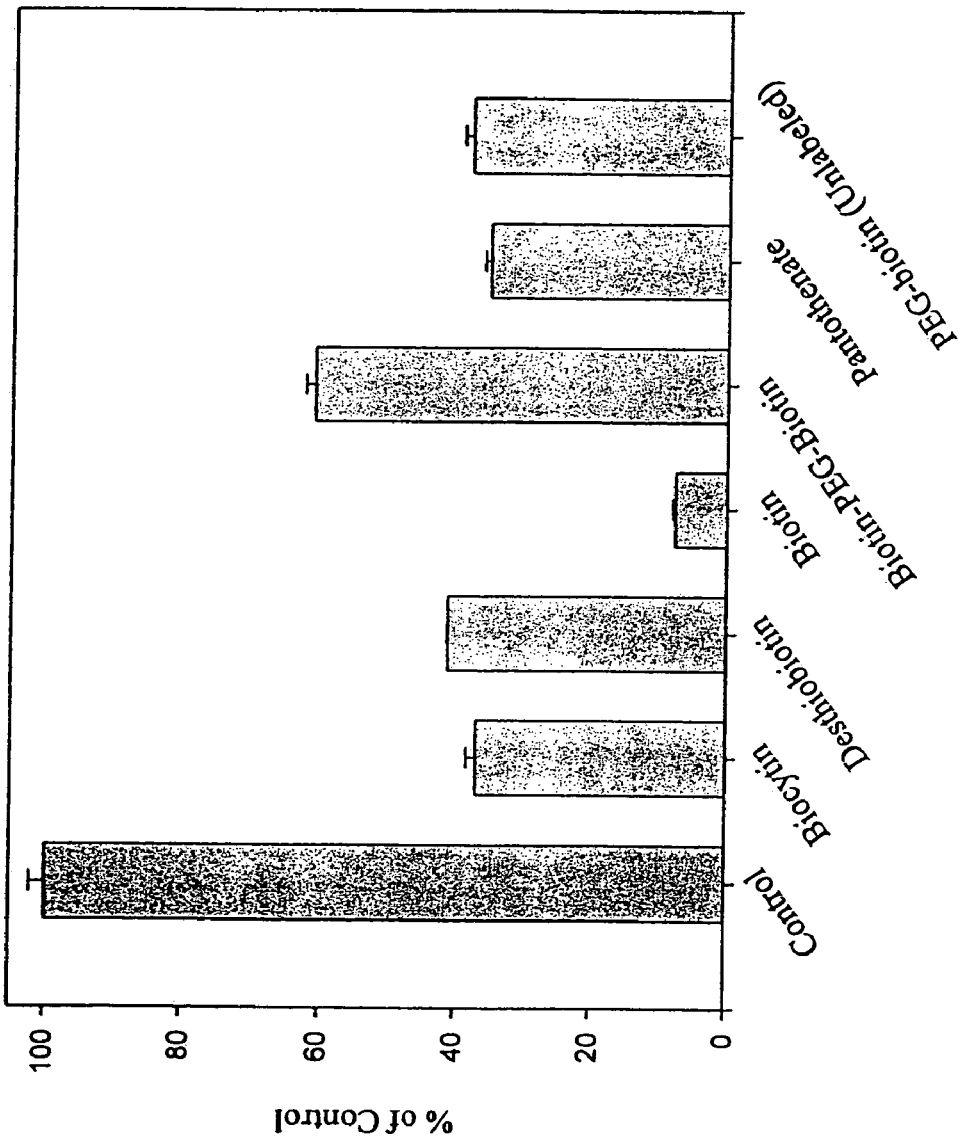
FIG. 3 depicts the uptake of 0.1 μM biotin-PEG-3400 in CHO/hSMVT cells measured for 10 minutes in the presence of 50 μM of SMVT substrates.

The interaction of biotin-PEG-3400 with SMVT was further validated by the CHO/hSMVT inhibition studies. Biotin-PEG-3400 uptake was significantly (p<0.01) inhibited by SMVT substrates biotin, pantothenic acid, desthiobiotin, biocytin, and a transport competitor biotin-PEG-biotin compared to the control, biotin-PEG-3400 alone (~4.57 pmol/mg protein/10 min) (FIG. 3).

Figure 4:
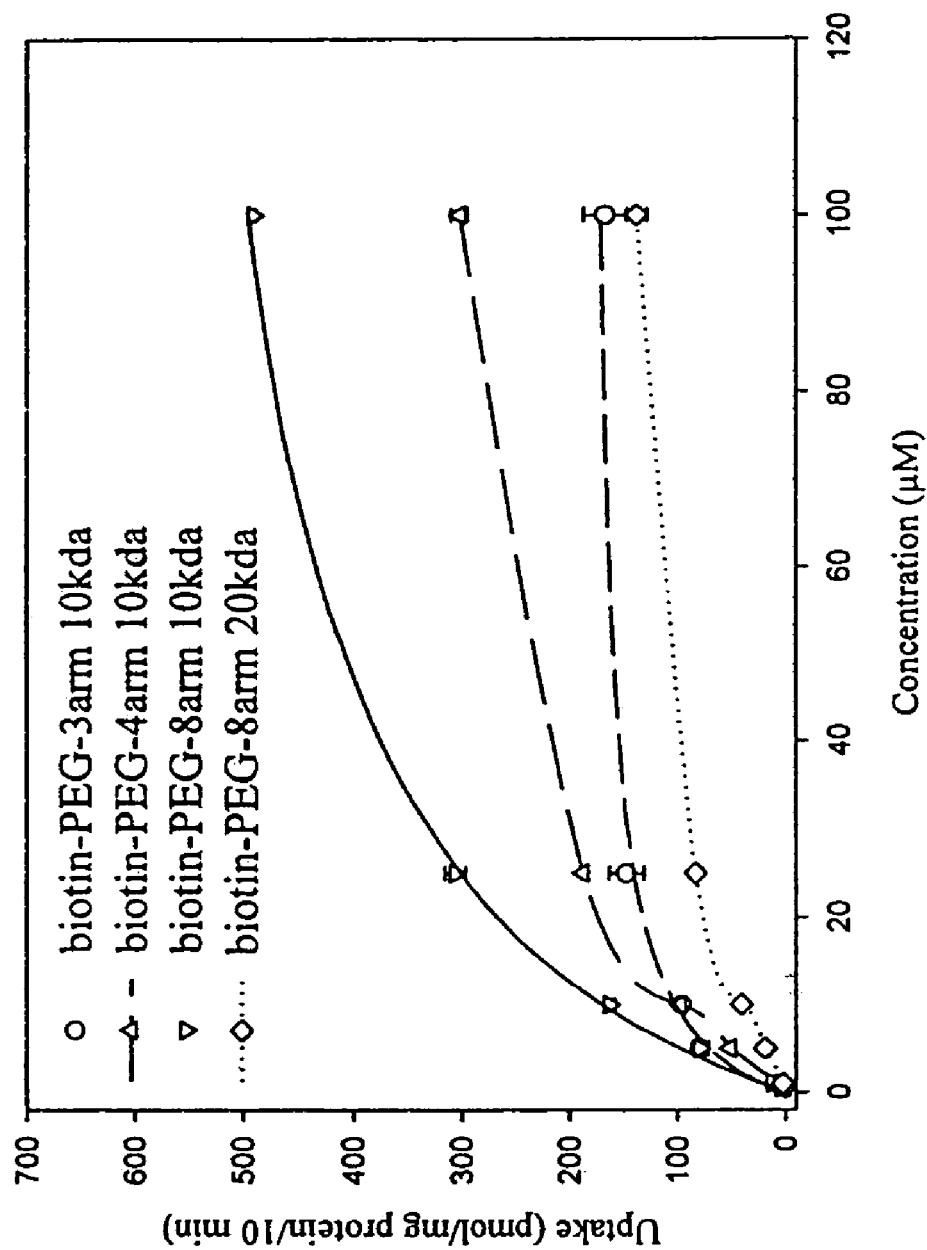
FIG. 4 shows the uptake of various branched biotin-PEGs in CHO/hSMVT cells at various concentrations.

Results of Uptake of branched biotin-PEGs Having shown that biotin-PEG-3400 interacts with SMVT and can potentially serve as a carrier for pharmaceutical macromolecules, we then performed a mechanistic analysis to characterize the substrate structure-transporter interactions using biotin-PEGs of varying shapes and sizes. The branched biotin-PEG molecules displayed concentration dependent and saturable uptake kinetics in CHO/hSMVT cells (FIG. 4) and the kinetic parameters are presented in Table II.

TABLE II

Michaelis-Menten parameters for the uptake of branched biotin-PEG compounds in CHO/hSMVT cells.

| Substrate | $K_m$ (μM) | $J_{max}$ (pmol/mg protein/10 min) |
|---|---|---|
| Biotin-PEG-3 arm 10 kDa | 7.97 (1.95) | 183.27 (13.24) |
| Biotin-PEG-4 arm 10 kDa | 27.61 (1.30) | 385.56 (4.28) |
| Biotin-PEG-8 arm 10 kDa | 27.35 (1.92) | 630.85 (20.38) |
| Biotin-PEG-8 arm 20 kDa | 35.3 (3.92) | 185.45 (6.29) |
| Biotin-PEG-3400 | 1.26 (1.01) | 23.46 (5.04) |

At a given molecular weight of 10 kDa, the estimated $K_m$ and $J_{max}$ values of the biotin-PEGs increased with increasing degree of branching (i.e., number of arms) (Table II). However, at 20 kDa (biotin-PEG-8 arm), while the $K_m$ value increased further, the $J_{max}$ value was substantially lower. Uptake of the branched biotin-PEGs in CHO/pSPORT cells and the uptake of corresponding $NH_2$-PEG controls in CHO/hSMVT cells were extremely low (<1 pmol/mg protein/10 min) and not concentration dependent.

Results of Molecular Modeling of branched biotin-PEGs The hybrid Monte Carlo randomization searches led to the identification of several low-energy (E<2.5 kcal/mole) conformations for the linear and branched biotin-PEGs. The use of differing starting conformations to the search protocol yielded the same ensemble for a given compound, indicating that the conformational searches for the various compounds were convergent and the randomization step number allowed for a thorough coverage of the low energy regions on the conformational hypersurface. A representative 3-dimensional conformation of the linear and branched biotin-PEG molecules is shown in FIGS. 1A and 1B. The values of the molecular descriptors computed for the various biotin-PEG molecules are presented in Table 2, below. The estimated van der Waals surface areas and volumes of the biotin-PEGs increased with increasing degree of branching (linear—8 arm) and molecular weight (3 kDa-20 kDa). A similar pattern was also observed in the Kier and Hall connectivity indices and molecular refractivity, which are indicators of molecular volume. The kappa shape indices for the 10 kDa compounds decreased with increasing branching suggesting a more cyclic ($^1\kappa$), star-shaped ($^2\kappa$), and centrally-branched molecular structure at the highest PEG arm-number. However, all three indices were greater for biotin-PEG-8 arm/20 kDa. With greater branching and size, the molecules were more flexible as indicated by the Kieflex index, and more lipophilic based on logP values. All of the computed parameters were substantially greater for biotin-PEG-8 arm/20 kDa compared to the rest of the compounds. The relevance of these results in the present study is discussed in the following section.

Thus, as shown in the foregoing studies, increased transport is provided by increasing the number of biotin molecules appended to the arms of a branched PEG polymer. In the foregoing studies, the biotinylation of $NH_2$-PEG compounds was 90% complete, which means on an average, there were ~2.7 biotin molecules on the 3 arm, ~3.6 on 4 arm, and ~7.2 on 8 arm PEG molecules. Theoretically speaking, 3 arm PEG molecules would contain fragments with 0-3 biotins, 4 arm PEG molecules would contain fragments with 0-4 biotins and 8 arm PEG molecules would contain fragments with 0-8 biotins. However, due to the high degree of biotinylation (90%), the predominant fraction of biotin-PEGs would contain 3-biotins (in 3 arm PEGs), 4-biotins (in 4 arm PEGs), or 8"-biotins (in 8 arm PEGs). Since tritiation was performed after the biotinylation process, these fractions are not likely to be radioactive. Therefore, for a PEG with n arms, biotin-PEG-(n−1) would be the largest radioactive fraction, with an exponentially decreasing populations of biotin-PEG-(n−2), biotin-PEG-(n−3) and other smaller fragments. Thus, the present study essentially evaluated the transport of PEG molecules containing 2-, 3- or 7-biotins in the presence of PEG molecules with 3-, 4-, or 8-biotins. Given the presence of other less probable biotin-PEG fractions, numerically, the present data represent the average transport of a given compound. The qualitative trends observed in the transport properties are, however, real for the various biotin-PEGs. At a given molecular weight (10 kDa), the total uptake and maximal transport velocity ($J_{max}$) of branched biotin-PEG molecules increased as a function of arm number, i.e., number of appended biotin molecules (Table III).

TABLE III

Computational descriptors derived using the molecular operating environment (MOE) software.

| Biotin-PEG- | $^1\kappa$ | $^2\kappa$ | $^3\kappa$ | Area | $^0\chi + ^0\chi_v$ | $^1\chi + ^1\chi_v$ | SMR | Volume | Kier Flex |
|---|---|---|---|---|---|---|---|---|---|
| 3400 | 0.987 | 0.930 | 0.889 | 3552 | 286 | 186 | 78 | 4298 | 199 |
| 3 arm, 10 kDa | 1.038 | 0.987 | 0.947 | 11815 | 954 | 626 | 274 | 14349 | 656 |
| 4 arm, 10 kDa | 0.984 | 0.918 | 0.868 | 12235 | 990 | 647 | 284 | 14875 | 681 |

TABLE III-continued

Computational descriptors derived using the molecular operating environment (MOE) software.

| Biotin-PEG- | $^1\kappa$ | $^2\kappa$ | $^3\kappa$ | Area | $^0\chi + ^0\chi_v$ | $^1\chi + ^1\chi_v$ | SMR | Volume | Kier Flex |
|---|---|---|---|---|---|---|---|---|---|
| 8 arm, 10 kDa | 0.977 | 0.876 | 0.777 | 13214 | 1086 | 713 | 302 | 16232 | 705 |
| 8 arm, 20 kDa | 0.987 | 0.930 | 0.869 | 24641 | 1997 | 1308 | 552 | 29981 | 1393 |

Given the differing number of biotins on the various PEG molecules, the likelihood of biotin-SMVT interaction increases for PEG molecules with greater number of biotins (e.g., biotin-PEG-8 arm compared to biotin-PEG-3 arm). This may explain the greater uptake observed with biotin-PEG-8 arm/10 kDa compared to biotin-PEG-3 arm/10 kDa. Despite the increase in total uptake, the affinity ($K_m$) of biotin-PEGs to SMVT decreased at higher branching. This result is consistent with those reported elsewhere herein (see examples below), where a slight decrease in SMVT affinity was observed with a compound, biotin-PEG-biotin, compared to biotin-PEG-3400. Given the narrow range of $K_m$ values reported for known SMVT substrates in transfected cell systems (~1-5 µM) (H. Wang, W. Huang, Y-J. Fei, H. Xia, T. L. Y.-Feng, F. H. Leibach, L. D. Devoe, V. Ganaphthy, and P. D. Prasad, Human placental Na+-dependent multivitamin transporter: Cloning, functional expression, gene structure, and chromosomal localization, J. Biol. Chem. 274 (1999) 14875-14883; P. D. Prasad, H. Wang, W. Huang, Y-J. Fei, F. H. Leibach, L. D. Devoe, and V. Ganaphthy. Molecular and functional characterization of the intestinal Na+-dependent multivitamin transporter, Arch. Biochem. Biophys. 366 (1999) 95-106; N. S. Chatterjee, C. K. Kumar, A. Ortiz, S. A. Rubin, and H. M. Said. Molecular mechanism of the intestinal biotin transport process. Am. J. Physiol. 277:C605-C613 (1999); P. D. Prasad, S. Ramamoorthy, F. H. Leibach, and V. Ganaphthy. Characterization of a sodium-dependent vitamin transporter mediating the uptake of pantothenate, biotin and lipoate in human placental choriocarcinoma cells, Placenta 18 (1997) 527-533), the decrease in affinity observed in the present study (from ~1 µM to 35 µM) was quite substantial. These results suggest that the substrate properties of SMVT alters from high affinity, low capacity to low affinity, high capacity based on the degree of branching of poly-biotinylated PEGs. However, increasing the molecular weight of the biotin-PEG complex from 10 kDa to 20 kDa (biotin-PEG-8 arm) resulted in a dramatic drop in its uptake ($J_{max}$) and affinity ($K_m$) to the transporter, suggesting that the inverse relationship between biotin-PEG branching and capacity of trans port was a size-dependent phenomenon.

The computational modeling experiments were performed to understand the role of structural and geometric parameters on the interaction of biotin-PEGs with SMVT. The van der Waals surface area estimates increased as a function of degree of branching and molecular weight of the biotin-PEGs. At 10 kDa, the increase in surface area was marginal between the 3 arm and 8 arm compounds. However, the estimates for 8 arm/20 kDa were ~2-fold greater than those of 3 arm/10 kDa and 4 arm/10 kDa, and 7-fold greater than the linear biotin-PEG-3400. The relationship between linear combination of simple and valence χ indices ($^0\chi + ^0\chi_v$, $^1\chi + ^1\chi_v$) and the volume-related van der Waals 'b' parameter has been described previously (L. H. Hall and L. B. Kier, The relation of molecular connectivity to molecular volume and biological activity, Eur. J. Med. Chem. 16 (1981) 399-407). Molecular refractivity (SMR) has also been used to describe the bulk or global volume-related information (L. B. Kier, Indexes of molecular shape from chemical graphs, Med. Res. Rev. 7 (1987) 417-440). The additive χ index and molecular refractivity values increased with branching and molecular weight, which mirrored the trend observed with van der Waals volume estimates. These results suggest that smaller and less branched biotin-PEGs display the maximum affinity towards SMVT, while increasing the degree of branching and biotinylation can enhance the payload of uptake. The kappa descriptors provided shape-related information on the biotin-PEGs. At 10 kDa, as the number of PEG-arms increased from 3 to 8, all three indices decreased. Thus, the compounds assumed more cyclic and/or star graph-like structures at higher branching. Interestingly, the $^1\kappa$ and $^2\kappa$ indices were similar for the linear biotin-PEG-3400 and biotin-PEG-8 arm/20/kDa and between the values of 3-arm and 4-arm 10 kDa compounds. Based on the Kierflex index, the flexibility of branched biotin-PEGs was shown to increase with branching and size, which may result in poorer interaction with the transporter. The substantially larger values of computed descriptors for biotin-PEG-8 arm/20 kDa compared to the other compounds indicated that beyond a critical mass, increase in molecular size results in substantial loss of uptake and affinity to the transporter. The above results collectively suggest preliminary predictive trend on the role of topological features of biotin-PEG carrier molecules on their ability to interact with SMVT. Further exhaustive studies are, however, necessary to fully understand the role of structural and geometric parameters on the interaction of substrates with SMVT.

EXAMPLE 2

Enhanced Oral Absorption of a Peptide by Targeting the SMVT

Materials RI-K(biotin)-Tat9 and RI-K-Tat9, both tritiated at the N-acetyl terminus, were synthesized in Dr. Stein's lab at Center for Advanced Biotechnology and Medicine (CABM, Piscataway, N.J.) as described in the section below titled 'Peptide Synthesis'. [$^3$H]Biotin, [$^{14}$C]mannitol and [$^{14}$C]PEG-4000 were obtained from NEN-Life Science Products (Boston, Mass.). The human sodium dependent multivitamin transporter, hSMVT, subcloned in the mammalian expression vector, pSPORT, was kindly provided by Dr. Puttur D. Prasad (Medical College of Georgia, Augusta, Ga.). All medium components and reagents for cell culture and molecular assay were obtained from Gibco Life Technologies, Inc. (Grand Island, N.Y.). All other chemicals were received from Sigma Chemical Co. (St. Louis, Mo.) or Fisher Scientific (Fair Lawn, N.J.) and used as received.

Peptide Synthesis RI-K(biotin)-Tat9, N-acetyl-D-Lys:(ε-biotin)-D-Arg-D-Arg-D-Arg-D-Gln-D-Arg-D-Arg-D-Lys-D-Lys-D-Arg-NH$_2$ (SEQ ID NO: 9), was synthesized manually on a PAL resin by Fmoc chemistry using reagents from PerSeptive Biosystems (Framingham, Mass). Biotin was appended to the ε-amine group of the lysine side chain using the reagent, NHS-biotin (N-hydroxy succinimide, Pierce, Rockford, Ill), as follows. After assembly of the peptide and while still attached to the solid support, the Mtt (3-(4,5-dimethyl-2-thiazyl)-2,5-diphenyl-2H-tetrazolium bromide) protecting group was removed from the lysine side chain of RI-K-Tat9 by drop-wise addition of 1% trifluoroacetic acid (TFA) in dichioromethane at the rate of 1 ml/min for 2 hours. The solid support was washed with dimethylformamide, and NHS-biotin in DMF was added at 5-fold molar excess. Conjugation with biotinylation reagent proceeded overnight with vigorous shaking. Peptides were cleaved from the support and deprotected by treatment with a mixture of 90% TFA, 5% thioanisole, 2% anisole and 3% ethanedithiol for 4 hours. The peptides were then purified by reverse-phase high-performance liquid chromatography and characterized by mass spectrometry for the molecular ion. Peptide concentration was determined by amino acid analysis. The synthesis of RI-K-Tat9 N-acetyl-D-Lys-D-Arg-D-Arg-D-Arg-D-Gln-D-Arg-D-Arg-D-Lys-D-Lys-D-Arg-NH$_2$ (SEQ ID NO: 9) entailed the same procedure as RI-K(biotin)-Tat9 except for attachment of biotin.

Cell Culture Protocols The Caco-2 cell line was obtained from American Type Culture Collection (ATCC) (Rockville, Md.) at passage 25. Cells were maintained in Dulbecco's Modified Eagle's Medium (DMEM) containing 10% heat-inactivated fetal bovine serum, 1% nonessential amino acids, penicillin (100 U/ml), and streptomycin (100 mg/ml), in an atmosphere of 95% air and 5% $CO_2$ at 37° C. Culture medium was changed every other day and cells were passed every 3-5 days by trypsinizing cells with 0.05% trypsin and 0.53 mM EDTA at 37° C. for 10 minutes. After harvesting at 90% confluency (determined using a Zeiss Telaval 31 inverse phase contrast microscope), cells were seeded at a density of 63,000/cm$^2$ on Snapwell inserts with 0.4 μm pore diameter (Corning-Costar, Cambridge, Mass.). Cells at passage number 27-30 cultured for 3-4 weeks after seeding were used for all experiments. For cell density determinations, the cell suspensions grown in various T-flasks were combined into a centrifuge tube and shaken gently for even distribution. Using aseptic technique, the cell suspensions were stained with trypan blue and counted using a hemacytometer. Appropriate dilution was made with fresh media (in a centrifuge tube) to bring cell density to 1.25×10$^5$ cells/ml (target cell density on Snapwell: 63,000/cm$^2$). CHO cells were obtained from ATCC at passage 4 and cultured under similar conditions as Caco-2 cells except that trypsinization during cell passage was done for 2 minutes instead of 10 minutes. Upon reaching confluency, the cells were transfected with the human sodium dependent multivitamin transporter, hSMVT, subcloned in the mammalian expression vector, pSPORT. The cells were transfected with hSMVT or pSPORT (vector control) by Lipofectamine according to the manufacturer's instructions (GIBCO BRL). Briefly, after harvesting at 90% confluency, the cells were seeded at a density of 3×10$^5$ cells/well in 12-well culture plates and incubated at 37° C. for 24 hours. For each well, 1 μg of DNA was mixed gently with 200 μl of serum-free medium and 10 μg of Lipofectamine reagent. The mixture was incubated at room temperature for 15 minutes and transferred to each well. Then 0.8 ml of serum-free medium was added to the mixture. After a 5-hour incubation at 37° C., the transfection mixture was removed and replaced with 1 ml of complete growth containing 10% FBS.

Caco-2 Cell Validation Studies A series of validation studies were performed to ensure that the transport results were not confounded by factors that could lead to the misinterpretation of results. In order to validate the barrier properties of the Caco-2 cell monolayers, prior to experimentation, the cells were rinsed twice with pre-warmed Ringer's with glucose buffer (pH 7.4, iso-osmotic) and trans-epithelial electrical resistance (TEER) was measured using an EVOM epithelial voltmeter equipped with an Endohm electrode (World Precision Instruments, Sarasota, Fla.) both before and after experimentation. In addition, marker compounds were selected to characterize the monolayers. Specifically, the transport of mannitol, an indicator of paracellular transport, and poly(ethylene glycol)-4000, a nonabsorbable marker, used as indicators of the barrier properties of the monolayers. The chemical purity of the radiolabeled compounds ranged from 97% to 99% according to the information provided by the manufacturers. Tritium exchange between the $^3$H-labeled compounds and $H_2O$ was quantified by air drying 100 μl aliquots of solutions containing each radiolabeled compound at their respective experimental concentrations in a fume hood overnight. The remaining radioactivity was compared to controls made before evaporation. The extent of adsorptive binding of RI-K(biotin)-Tat9 to the components of the diffusion chamber system was evaluated in a mass-balance study. Transport of RI-K(biotin)-Tat9 was studied using a blank Snapwell™ filter and at the end of the experiment, residual radioactivity in the filter, its plastic support, the O-ring, and the chambers was determined.

Caco-2 Cell Transport Studies An Ussing-type diffusion chamber system (Harvard Apparatus, Natick, Mass.) was used to perform transport studies. The apical solution was a MES Ringer's buffer (pH 6.5) consisting of 114.0 mM NaCl, 5.0 mM KCl, 1.1 mM MgSO$_4$, 1.25 mM CaSO$_4$, and 15 mM 2-(N-morpholino)ethanesulfonic acid (MES). The basolateral solution was a Ringer's buffer (pH 7.4) consisting of 114.0 mM NaCl, 5.0 mM KCl, 1.65 mM Na$_2$HPO$_4$, 0.3 mM NaH$_2$PO$_4$, 25 mM NaHCO$_3$, 1.1 mM MgSO$_4$, and 1.25 mM CaSO$_4$. Both buffers contained 25 mM glucose and were adjusted to 290 mOsm/kg using a vapor pressure osmometer (Wescor Inc, Logan, Utah). For transport experiments using filters with cell monolayers, the inserts were rinsed with Ringer's buffet containing 25 mM glucose three times over a 20 min period at room temperature. The TEER was measured for each monolayer before it was mounted onto the diffusion chamber, which was pre-warmed to 37° C. by placement on the heating blocks. The volume of each half-chamber was 5 ml and the surface area of the Snapwell™ filters available for drug transport was 1 cm$^2$. The fluids in the chambers were circulated using a gas lift mechanism with 5% $CO_2$/95% $O_2$; flow rate was adjusted to 10 m/min and monitored using a J&W ADM2000 gas flow meter (Fisher Scientific, Fair Lawn, N.J.). The donor solution consisted of radiolabeled permeant in the apical buffer [apical (AP) to basolateral (BL) study]. Starting at 30 min, samples were taken from the receptor chamber every 15 min until the end of the experiment (105 min). A minimum of three monolayers was used to determine the permeability of test compound in each study and sample analysis was performed using scintillation counting (Perkin Elmer, Gaithersburg, Md.).

CHO Cell Uptake Studies CHO cells transiently transfected with hSMVT were washed twice with 25 mM uptake buffer, containing 25 mM Hepes/Tris pH 7.5, 140 mM NaCl, 5.4 mM KCl, 1.8 CaCl$_2$, 0.8 mM MgSO$_4$ and 5 mM glucose. Subsequently, the cells were incubated with the permeant at 37° C. for 10 minutes. Washing the cells three times with ice-cold buffer stopped drug uptake. Non-specific uptake was measured in parallel experiments with the control pSPORT vector-transfected CHO cells. Finally, the cells were solubilized by 0.1% v/v Triton X-100, and 0.6 ml was used for scintillation counting. From the remaining volume, 10 µl of solution was taken from each well and protein concentration was determined using the Bio-Rad reagent according to the manufacturer's instructions. Bovine serum albumin was used as the standard.

Gene Expression using Reverse Transcription-Polymerase Chain Reaction (RT-PCR)

The presence of SMVT in Caco-2 cells and transfected CHO cells was determined using RT-PCR. Total RNA from Caco-2, CHO/hSMVT and CHO/pSPORT cells was isolated with TRIzol reagent (promega, Madison, Wis). The first strand of cDNA was synthesized using 3 µg of RNA, 2 pmol of reverse primer, 10 mM dithiothreitol, 0.5 mM dATP, dCTP, dGTP and dTTP, and 200 units of Superscript II reverse transcriptase as described by the manufacturer (GIBCO BRL). Two specific primers were synthesized based on human SMVT. The sequences for forward and reverse hSMVT primers were 5'-CTG TCC GTG CTG GCC CTG GGC-3'(SEQ ID NO: 10) and 5'-GAC CAG GCC AAT GAG GCA GCC-3' (SEQ ID NO: 11), respectively. PCR was performed using 50 µl of reaction volume containing 10 ng of cDNA, 0.2 mM $MgCl_2$, 0.5 µM primers, and 2.5 units of Taq DNA polymerase. The reaction was run for 30 cycles with denaturation at 94° C. for 1 min, annealing at 55° C. for 1 minute, and extension at 72° C. for 1 minute. The PCR products were electrophoresed through 1.5% agarose gel containing ethidium bromide and images captured using NucleoTech imaging system (NucleoTech, San Mateo, Calif).

Functional Assay of SMVT In order to confirm the expression of SMVT in Caco-2 cell monolayers, the transport of biotin (0.1-100 µM) was studied. Transport activity of CHO/hSMVT cells was examined using [$^3$H]biotin (0.1-25 µM). The time-period post-transfection for optimal uptake was determined by performing uptake experiments at 24 hr, 36 hr, 48 hr, and 72 hr after transfection. At each of these time points, uptake studies were performed for 5 min, 10 min, 20 min, and 30 min and the experimental duration (time course) for optimal uptake was also determined.

Concentration Dependence The concentration dependence of RI-K(biotin)-Tat9 in Caco-2 cell monolayers was determined by evaluating its AP to BL or absorptive transport at concentrations ranging from 1-10 µM. The effective permeability, $P_e$, (cm/sec) was determined using the equation $$P_e = dC/dt * V_r / AC_0$$

where $V_r$ is the volume of the receptor chamber (5 ml), A is the surface area of the filter (1.13 cm$^2$), $C_0$ is the initial drug concentration, and dC/dt is the flux (J) determined by the linear slope of receptor drug concentration versus time plot after correcting for dilution. RI-K-Tat9 (0.01-25 µM) was used in the control experiments. The uptake of RI-K-Tat9 (0.1-10 µM) and RI-K(biotin)-Tat9 (0.1-10 µM) was also studied in CHO/hSMVT and CHO/pSPORT cells. The Michaelis-Menten kinetic parameters of Caco-2 and CHO cell transport were then estimated using non-linear regression.

Temperature Dependence The temperature dependence studies were performed to determine the presence or absence of an ATP-dependent mechanism in RI-K(biotin)-Tat9 transport across Caco-2 cells. Prior to experimentation, diffusion chambers mounted with the Snapwells™ containing Caco-2 cells were equilibrated at 5° C., 10° C., 15° C., 25° C. and 37° C. Transport of RI-K(biotin)-Tat9 (1 µM) was then evaluated at the above temperatures and permeability values were calculated.

Inhibition Studies The involvement of SMVT in the Caco-2 cell monolayer transport of RI-K(biotin)-Tat9 was investigated through inhibition studies that were performed by co-incubating RI-K(biotin)-Tat9 with known competitive substrates of SMVT in the donor solution (AP) of the diffusion chambers. The tritiated drug (0.1 µM) was co-incubated with 10 µM and 20 µM concentrations of biotin, biocytin, and desthiobiotin. Further, RI-K(biotin)-Tat9 (0.1 µM) uptake was determined in CHO/hSMVT cells in the presence of biotin, pantothenic acid, desthiobiotin, and biocytin (50 µM) and compared to the control (uptake of RI-K(biotin)-Tat9 alone).

Data Analysis The apparent activation energy ($E_a$) was determined from the slope ($E_a$/2.303 R, where R (molar gas constant)=0.001987 kcal/deg mole) of the log $P_e$ versus 1/T plot(T=absolute temperature (T ° C.+273.16° C.)) based on the Arrhenius equation, $$\log P_e = A - \frac{E_a}{2.303RT}$$

where A is the Arrhenius constant.

The kinetic parameters for the Michaelis-Menten studies were calculated by performing non-linear regression with Scientist™ software (MicroMath, Salt Lake City, Utah) using the following equation:

$$P_e = \frac{P_c}{1 + \frac{C_s}{K_m}} + P_m$$

where $P_e$ is the effective permeability of the substrate transported, $C_s$ is the substrate concentration and $P_m$ and $P_c$ represent the passive and carrier-mediated component of the permeability. All data were initially fitted to a 3-parameter model ($P_c$, $P_m$, $K_m$ for Caco-2 studies, $J_{max}$, $P_m$, $K_m$ for CHO studies). If $P_m$ was not significantly differently from 0, then data was refit using a 2-parameter model ($J_{max}$, $K_m$). The data from inhibition studies were transformed into Lineweaver-Burke plots to determine the nature of the inhibition process (competitive, non-competitive). Subsequently, the inhibition constant ($K_i$) values were estimated using Dixon plots. Data used for the above plots were weighted using 1/SEM$^2$ (S.E.M=Standard Error of Mean). The kinetic parameters for CHO cell studies were estimated by performing non-linear regression using the equation $J=J_{max}*[C]/(K_m+[C])+P_m*C$, where J is the rate of permeant uptake, $P_m$ is the passive uptake component and [C] is the substrate concentration. Data were weighted using 1/S.E.M$^2$.

Statistical analyses were performed using Jandel SigmaStat, version 2.03. One-way analysis of variance was used to test the difference in the mean values of uptake using p<0.05 as the significance level for all tests. Results. The Caco-2 cell validation studies were performed to determine the functional integrity of the monolayers. TEER measurements indicated values of 310-340 Ω.cm$^2$, both before and after the transport experiments. The permeability of mannitol was determined to be 2.12 (±0.45)×10$^{-6}$ cm/sec and that of PEG-4000 was minimal (~10$^{-8}$ cm/sec). These results indicate that the cell monolayers were not leaky or damaged. The studies performed to measure tritium exchange indicated no significant differences in the radioactivity of the air-dried samples when compared to the controls, indicating the absence of proton transfer. The mass-balance study indicated minimal binding of RI-K(biotin)-Tat9 to the components of the diffusion chamber (2-4%). For all the permeants studied, concentrations in the receptor chamber were linear with time for the duration of the experiments.

Figure 5:
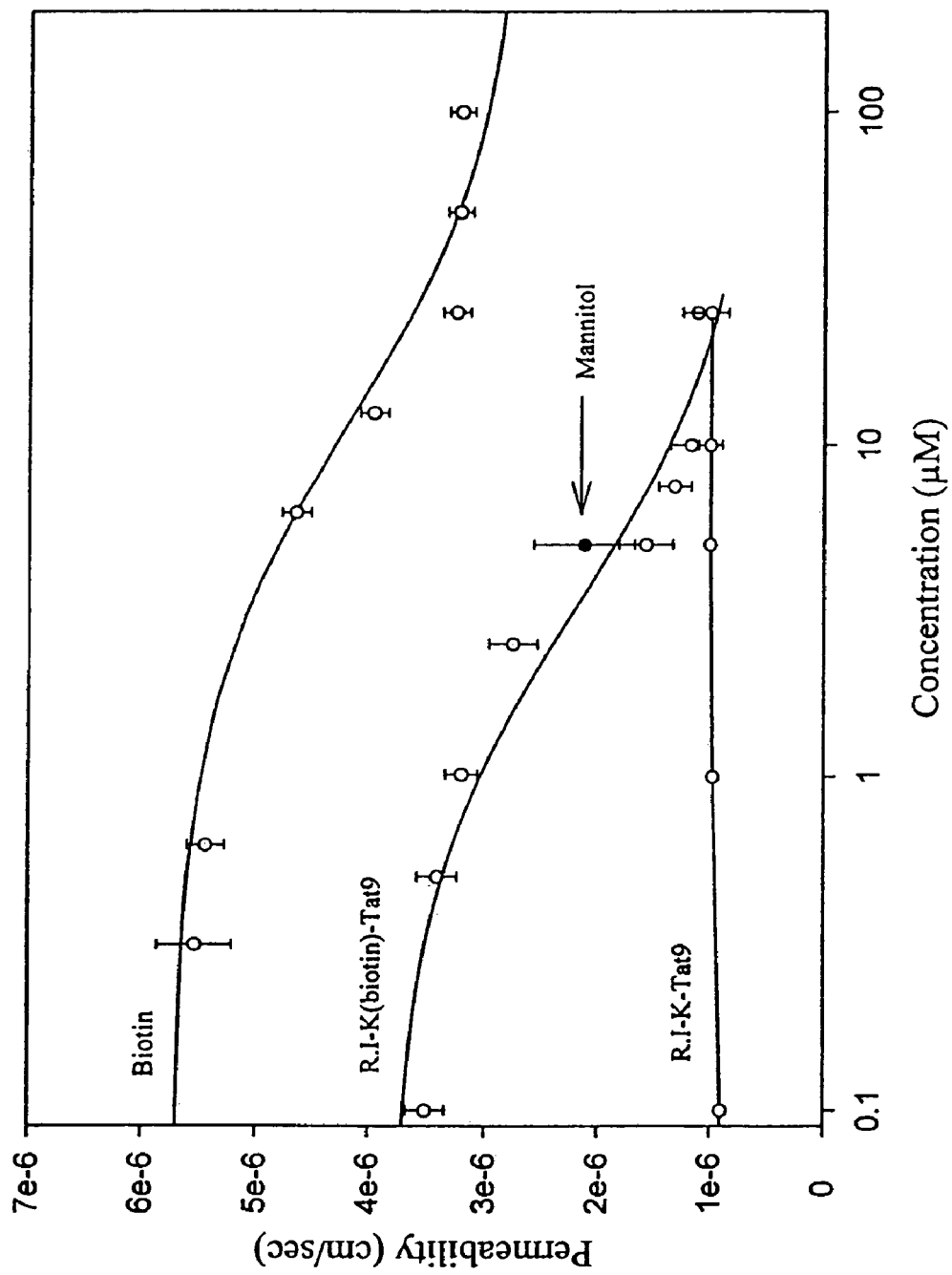
FIG. 5 depicts the absorptive transport of biotin, RI-K-Tat9 and RI-K(biotin)-Tat9 across Caco-2 cell monolayers.

Functional Assay of SMVT The transport of biotin across Caco-2 cell monolayers was studied to demonstrate the functional expression of SMVT in this cell line. The absorptive transport of biotin was concentration dependent and saturable (FIG. 5). The Michaelis-Menten kinetic parameters of biotin transport are shown in Table IV.

TABLE IV

Michaelis-Menten parameters for biotin and RI-K(biotin)-Tat9 transport across Caco-2 cell monolayers and uptake in CHO/hSMVT cells.

| Cell System | Kinetic Parameter | Biotin | RI-K(biotin)-Tat9 |
|---|---|---|---|
| Caco-2 Cell Monolayer Transport | $P_c$ (*10$^{-6}$) (cm/sec) | 3.35 (0.45) | 3.22 (0.30) |
| | $P_m$ (*10$^{-6}$) (cm/sec) | 2.67 (0.43) | 0.57 (0.31) |
| | $K_m$ (µM) | 11.28 (6.45) | 3.27 (1.46) |
| CHO/hSMVT Cellular Uptake | $J_{max}$ (pmol/mg protein/10 min) | 174.61 (47.53) | 227.26 (29.33) |
| | $P_m$ (pmol/mg protein/10 min) | 3.50 (3.0) | 32.90 (4.48) |
| | $K_m$ (µM) | 1.39 (0.59) | 1.00 (0.13) |

$P_c$: Carrier-Mediated Permeability Component;
$P_m$: Passive Permeability Component;
$J_{max}$: Maximum Uptake Rate;
$K_m$: Michaelis Constant.
Numbers in parentheses represent Standard Deviation (S.D);
n = 3.

The initial rate time point (10 minutes) for biotin uptake in the CHO/hSMVT cells was selected because maximal uptake was observed at 30 minutes in the time course studies. The duration post-transfection for optimum uptake was determined to be 48 hours (data not shown). Biotin uptake was concentration dependent and saturable (FIG. 6) with $K_m$ and $J_{max}$ values of 1.39±0.59 µM and 174.61±47.53 pmol/mg protein/10 min, respectively. Uptake was significantly lower (p<0.01) in the control CHO/pSPORT cells (23.73 pmol/mg protein/10 min).

Figure 7:
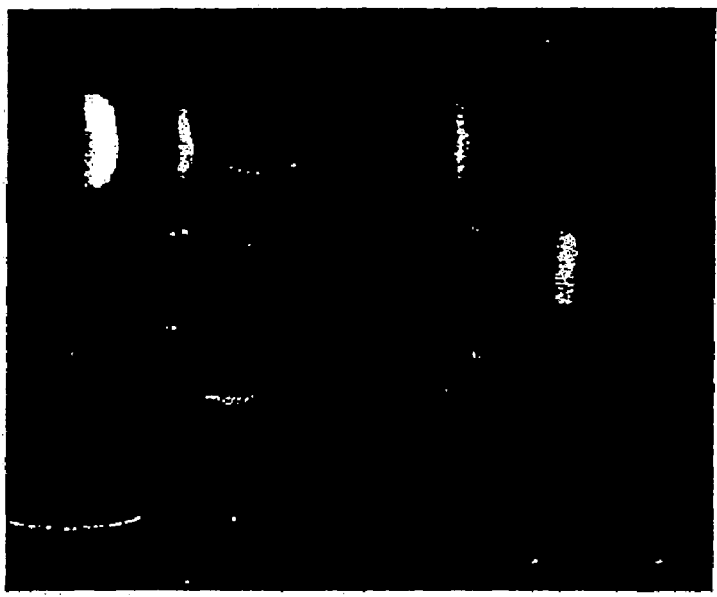
FIG. 7 shows images of PCR products after electrophoresis through a 1.5% agarose gel indicating the presence of the SMVT gene in Caco-2 and CHO/hSMVT cells and its absence in CHO/pSPORT cells. The size of the marker is shown in base pair units.

SMVT Expression in Caco-2 and CHO cells A single amplified DNA band was detected in Caco-2 and CHO/hSMVT cells and was absent in the CHO/pSPORT control cells (FIG. 7). The DNA was ~400 base pairs (bp) as expected from the size of the fragment between the forward (923-943) and reverse (1333-1313) primer positions.

Concentration Dependence of RI-K-Tat9 and RI-K(biotin)-Tat9 The absorptive transport of RI-K-Tat9 across Caco-2 cell monolayers was low ($P_m$~0.9×10$^{-6}$ cm/s), not concentration dependent and the probable result of passive diffusion (FIG. 5). Therefore further studies with RI-K-Tat9 were not performed. The absorptive transport of RI-K(biotin)-Tat9 across Caco-2 cells exhibited concentration dependent and saturable kinetics (FIG. 5). The Michaelis-Menten kinetic parameters for RI-K(biotin)-Tat9 transport are presented in Table I. The $K_m$ value for absorptive transport was low (3.27 µM), suggesting the potential involvement of a high affinity, low capacity transporter system.

Figure 6:
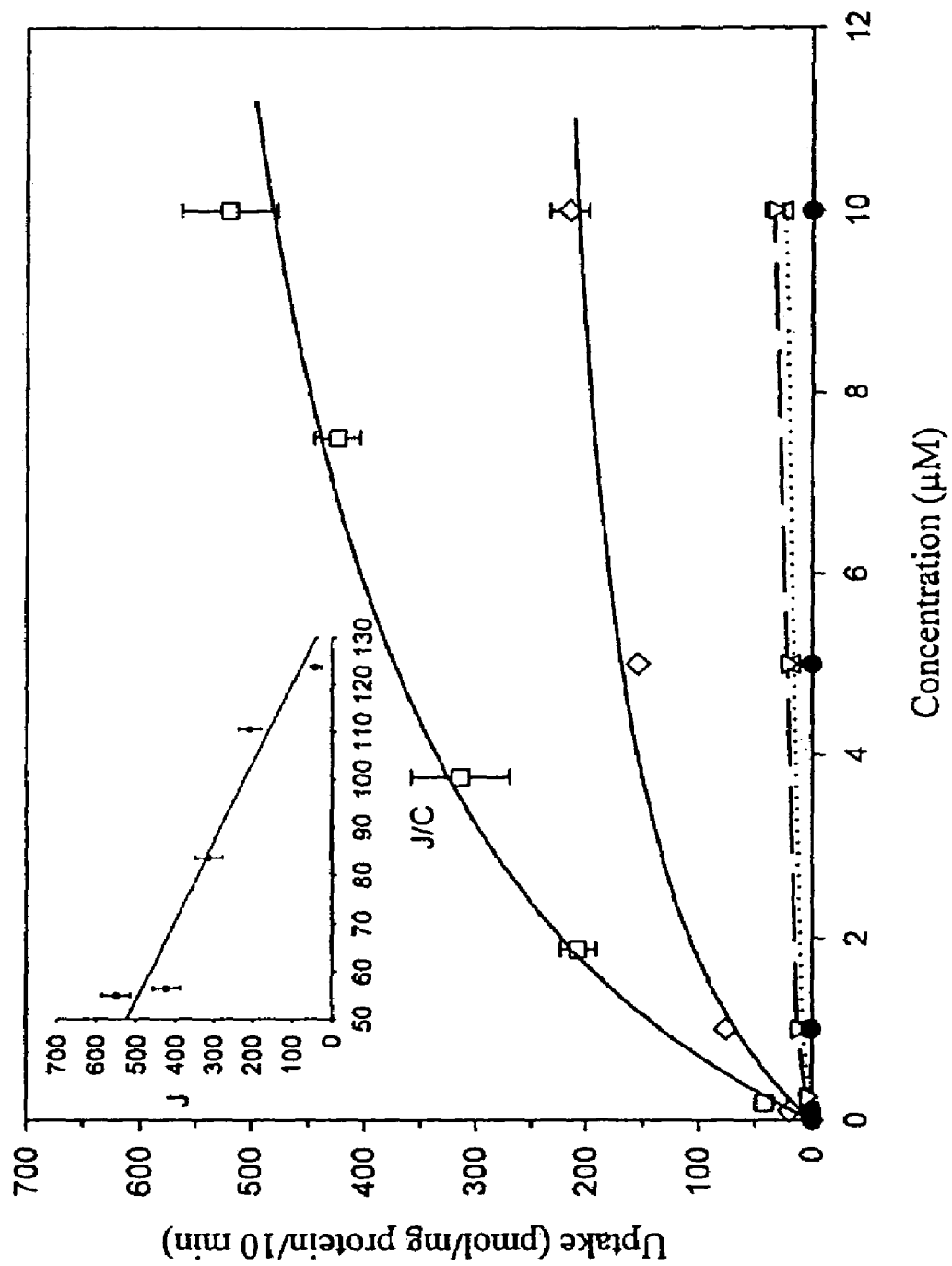
FIG. 6 shows the uptake of biotin, RI-K-Tat9 and RI-K (biotin)-Tat9 in CHO/hSMVT and CHO/pSPORT cells.

The uptake of RI-K(biotin)-Tat9 in CHO/hSMVT cells was concentration dependent and saturable (FIG. 2) with $K_m$ and $J_{max}$ values of 1.00±0.13 µM and 227.26±29.33 pmol/mg protein/10 min, respectively. Transformation of the uptake data into an Eadie-Hofstee plot (r=0.96) (FIG. 6 inset) indicated that the kinetics of RI-K(biotin)-Tat9 uptake matched a single saturable carrier model. The uptake of RI-K-Tat9 in CHO/hSMVT was extremely low (<1 pmol/mg protein/10 min) and not concentration dependent, indicating the absence of any interaction with hSMVT (FIG. 6). RI-K(biotin)-Tat9 uptake in CHO/pSPORT cells (~33.83 pmol/mg protein) was significantly lower (p<0.01) than in CHO/hSMVT cells, but higher than RI-K-Tat9 uptake in CHO/hSMVT and CHO/pSPORT cells (<1 pmol/mg protein/10 min).

Figure 8:
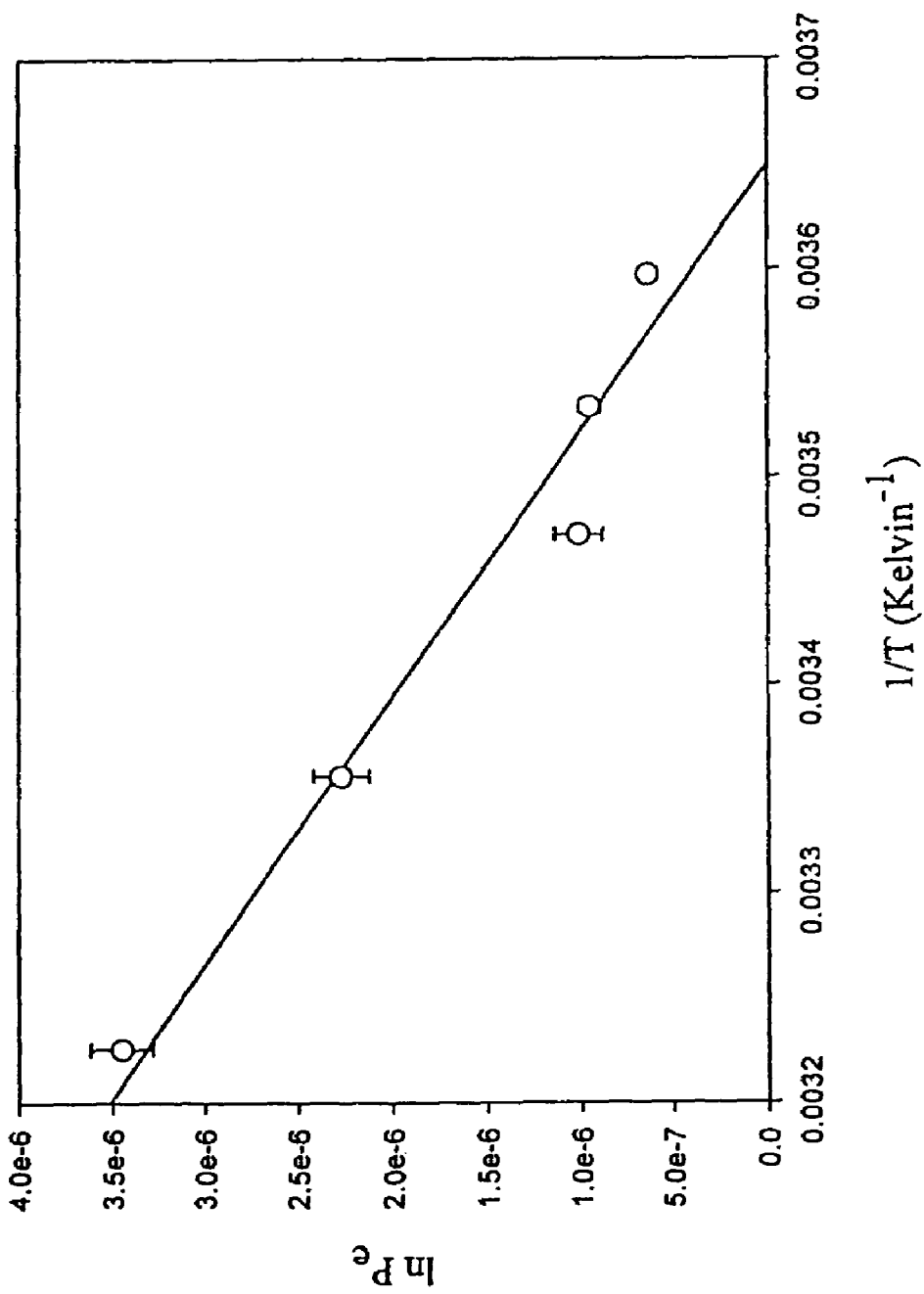
FIG. 8 depicts the temperature dependence of RI-K(biotin)-Tat9 transport across Caco-2 cell monolayers in the AP to BL direction.

Temperature Dependence The energy dependence of RI-K(biotin)-Tat9 transport across Caco-2 cell monolayers was evaluated. The $P_e$ values for RI-K(biotin)-Tat9 transport decreased with decreasing temperature. The $E_a$ value estimated from the Arrhenius plot was 9.11 kcal/mole (FIG. 8).

Inhibition Studies

Figure 9:
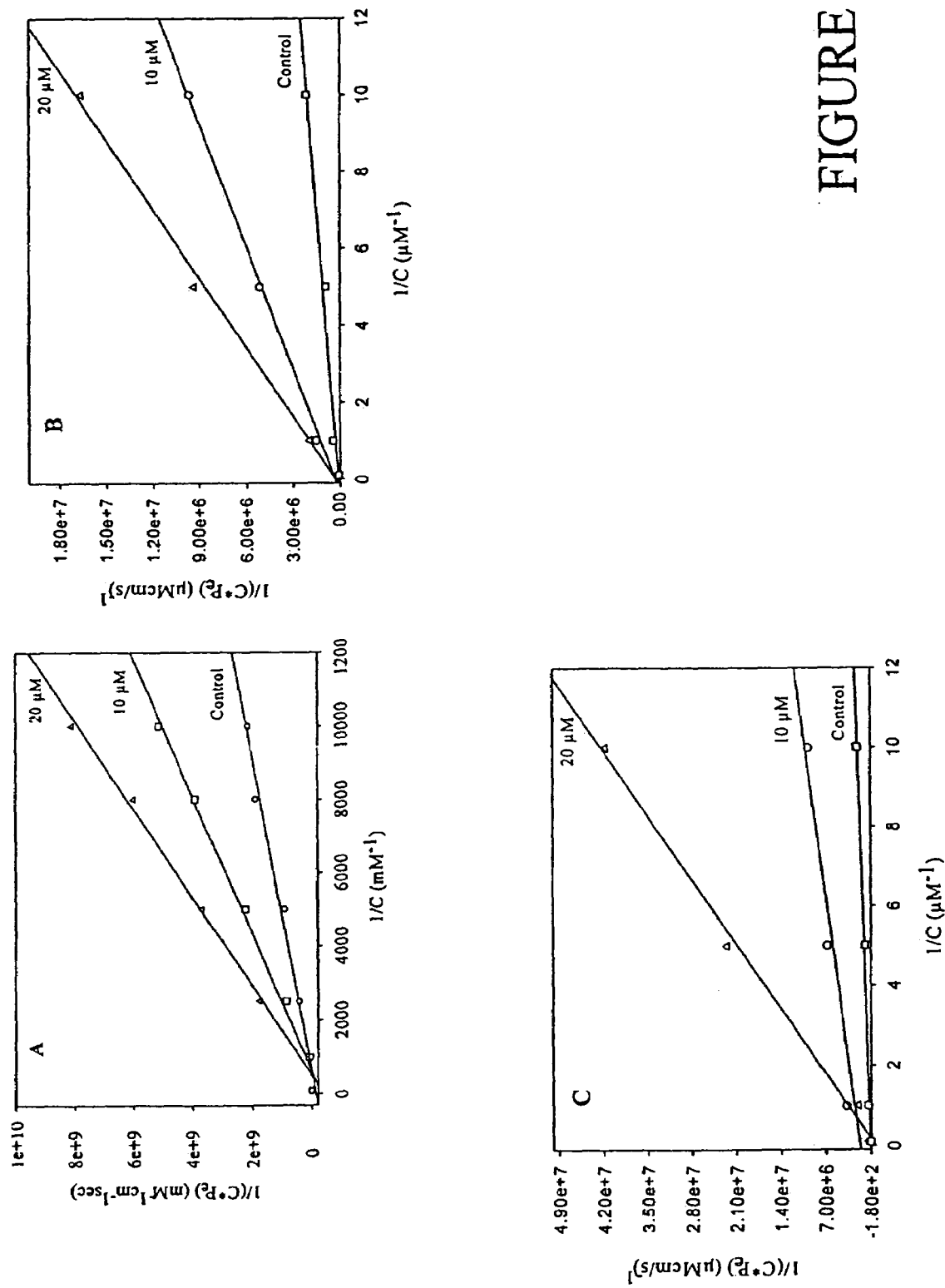
FIG. 9 shows a Lineweaver-Burke plots of RI-K(biotin)-Tat9 transport across Caco-2 cell monolayers in the presence of A) biotin, B) biocytin, and C) desthiobiotin, used as inhibitors at 10 and 20 μM.

Inhibition studies were performed with biotin, biocytin and desthiobiotin, known competitive substrates of SMVT. The Lineweaver-Burke plots suggested competitive inhibition of RI-K(biotin)-Tat9 transport by biotin (FIG. 9A) and its structural analogues biocytin (FIG. 9B) and desthiobiotin (FIG. 9C) with $K_i$ values of 7.88 µM, 3.27 µM, and 1.18 µM, respectively.

Figure 10:
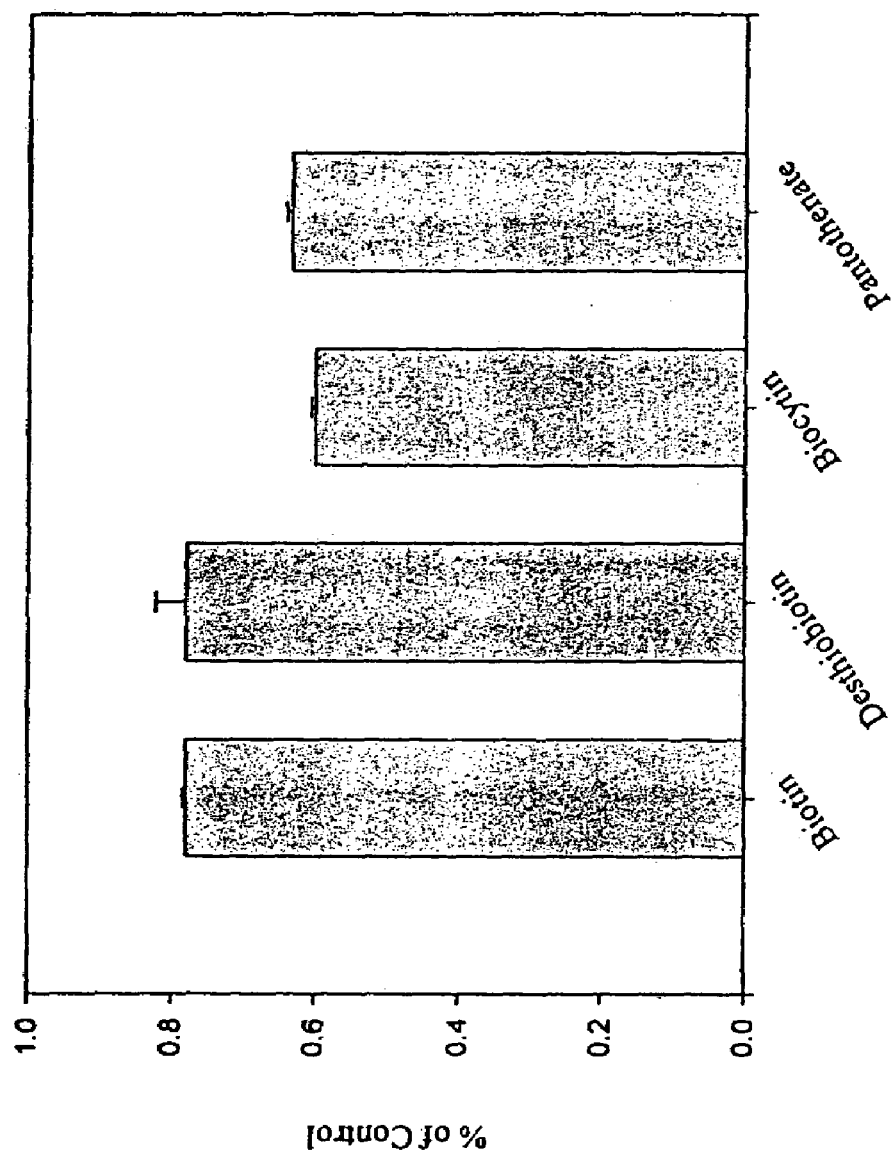
FIG. 10 shows the uptake of 0.1 μM RI-K(biotin)-Tat9 in CHO/hSMVT cells measured for 10 minutes in the presence of 50 μM of SMVT substrates.

The interaction of RI-K(biotin)-Tat9 with hSMVT was further evident from CHO/hSMVT cell inhibition studies. RI-K(biotin)-Tat9 uptake was significantly inhibited by biotin, pantothenic acid, desthiobiotin, and biocytin compared to the control, RI-K(biotin)-Tat9 alone-(~41.93 pmol/mg protein/10 min) (FIG. 10).

EXAMPLE 3

Further Enhancement of Intestinal Absorption Demonstrated Using CHO Cells

Materials PEG:(RI-K-Tat9)$_8$ and PEG:(RI-K(biotin)-Tat9)$_8$ were synthesized as described below. α,ω-Biotin-PEG-NHS (PEG M.W.=3400) was purchased from Shearwater Polymers, Inc. (Huntsville, Ala.) and tritiated ([$^3$H]biotin-PEG-3400, specific radioactivity 1.542 mCi/mmol) as described below. [$^{14}$C]mannitol and [$^{14}$C]PEG-3350 were obtained from NEN-Life Science Products (Boston, Mass.). The human sodium dependent multivitamin transporter, hSMVT, subcloned in the mammalian expression vector, pSPORT, was kindly provided by Dr. Puttur D. Prasad (Medical College of Georgia, Augusta, Ga.). All medium components and reagents for cell culture were obtained from Gibco Life Technologies, Inc. (Grand Island, N.Y.). All other chemicals were received from Sigma Chemical Co. (St. Louis, Mo.) or Fisher Scientific (Fair Lawn, N.J.) and used as received.

Synthesis of PEG:Tat9 Conjugate RI-K(biotin)-Tat9-Cys was manually synthesized on a PAL resin by Fmoc chemistry using reagents from PerSeptive Biosystems (Framingham, Mass.). For radiolabeling, the assembled peptide on the solid support (prior to N-acetylation) was allowed to react with tritiated acetic anhydride (specific activity 6.6 Ci/mmol) in the presence of coupling activation reagents BOP, HOBt, and DIEA. Acetylation of the peptide was completed with an excess of unlabelled acetic anhydride. After cleavage from the solid support and ether precipitation, the radiolabeled peptide was purified by chromatography on Sephadex G-10 using phosphate-buffered saline (PBS) (0.15 M NaCl, 20 mM potassium phosphate buffer, pH 7.4) for elution.

The starting material for the carrier polymer was α,ω-diamino-PEG (M.W~2000 Da) (Shearwater Polymers Inc.).

It was then co-polymerized by the method of Kohn et al. (Nathan, A.; Zalipsky, S.; Ertel, S. I.; Agathos, S. N.; Yarmush, M. I.; Kohn, J. Copolymers of lysine and polyethylene glycol: a new family of functionalized drug carriers. Bioconj. Chem. 1993, 4, 54-62) with an equimolar amount of BOC-Asp using HOBt and BOP as catalysts. The resulting PEG-Asp copolymer was purified by precipitation with 10-volumes of cold ether. Using GPC/HPLC, the copolymer was estimated to have a molecular weight of ~27 kDa. The BOC protecting group on Asp was removed using trifluoroacetic acid (100%). The PEG-Asp conjugate dissolved in PBS (pH 8.0) was reacted with 3-fold molar excess of the bifunctional coupling agent, SPDP (Pierce Chemical Co., Rockford, Ill.), dissolved in dimethylsulfoxide, for 6 hours. This coupling reagent essentially converts an amino group to a thiol group protected by the thipyridine (TP) group. The conjugate was precipitated with ether again to remove excess SPDP reagents. The concentration of SPDP reacted polymer was determined on an aliquot based on the release of 2-thiopyridine (TP) using DTT. In this analytical procedure, an aliquot of the reaction mixture was reacted with excess DTT (pH 8.0) for 15 minutes and the amount of TP liberated was quantified spectrophotometrically at 343 nm (Carlsson, J.; Drevin, H.; and Axen, R. Protein thiolation and reversible protein-protein conjugation. N-Succinimidyl 3-(2-pyridyldithio)propionate, a new heterobifunctional reagent. Biochem. J. 1978, 173(3), 723-737). The SPDP-treated polymer was reacted with excess RI-K(biotin)-Tat9-Cys in PBS (pH 7.5) for 16 hours and coupling of peptide to the carrier was monitored at 343 nm. The PEG:RI-K(biotin)-Tat9-Cys conjugate was maintained under argon at −20° C. until use for transport experiments.

Biotin-PEG-3400 Tritiation The succinimide ester of biotin-PEG-3400 (biotin-PEG-CO2-NHS, 15.6 µmol) (Shearwater Polymers, Inc.) dissolved in 4 ml sodium carbonate (50 mM, pH 9.0) was added to 10-equivalent diaminobutane (1.64 mmol) and the mixture stirred overnight. Following aqueous dilution (30 ml), the resultant product was with extracted thrice with methylene chloride (30 ml) and reduced to 0.5 ml using a rotary evaporator. Subsequently, it was precipitated with ethyl ether, purified using HPLC with SEC column and dried under speed vacuum. It was then dissolved in 0.5 ml DMF and reacted with [$^3$H]acetic anhydride using BOP/HOBt as coupling reagents. The product was ether precipitated and dried under air.

Cell Culture Protocols The Caco-2 cell line was obtained from American Type Culture Collection (ATCC) (Rockville, Md.) at passage 25. Cells were maintained in Dulbecco's Modified Eagle's Medium (DMEM) containing 10% heat-inactivated fetal bovine serum, 1% nonessential amino acids, penicillin (100 U/ml), and streptomycin (100 mg/ml), in an atmosphere of 95% air and 5% $CO_2$ at 37° C. Culture medium was changed every other day and cells were passed every 3-5 days by trypsinizing cells with 0.05% trypsin and 0.53 mM EDTA at 37° C. for 10 minutes. After harvesting at 90% confluency (determined using a Zeiss Telaval 31 inverse phase contrast microscope), cells were seeded at a density of 63,000/cm$^2$ on Snapwell inserts with 0.4 µm pore diameter (Corning-Costar, Cambridge, Mass.). Cells at passage number 27-30 cultured for 3-4 weeks after seeding were used for all experiments. For cell density determinations, the cell suspensions grown in various T-flasks were combined into a centrifuge tube and shaken gently for even distribution. Using aseptic technique, the cell suspension was stained with trypan blue and counted using a hemacytometer. Appropriate dilution was made with fresh media (in a centrifuge tube) to bring cell density to 1.25×10$^5$ cells/ml (target cell density on Snapwell: 63,000/cm$^2$). CHO cells were obtained from ATCC at passage 4 and cultured under similar conditions as Caco-2 cells except that trypsinization during cell passage was done for 2 minutes instead of 10 minutes. Upon reaching confluency, the cells were transfected with the human sodium dependent multivitamin transporter, hSMVT, subcloned in the mammalian expression vector, pSPORT. The cells were transfected with hSMVT or pSPORT (vector control) by Lipofectamine according to the manufacturer's instructions (GIBCO BRL). Briefly, after harvesting at 90% confluency, the cells were seeded at a density of 3×10$^5$ cells/well in. 12-well culture plates and incubated at 37° C. for 24 hours. For each well, 1 µg of DNA was mixed gently with 200 µl of serum-free medium and 10 µg of Lipofectamine reagent. The mixture was incubated at room temperature for 15 minutes and transferred to each well. Then 0.8 ml of serum-free medium was subsequently added to the mixture. After a 5-hour incubation at 37° C., the transfection mixture was removed and replaced with 1 ml of complete growth containing 10% FBS.

Caco-2 Cell Validation Studies In order to validate the barrier properties of the Caco-2 cell monolayers, prior to experimentation, the cells were rinsed twice with pre-warmed Ringer's with glucose buffer (pH 7.4, iso-osmotic) and trans-epithelial electrical resistance (TEER) was measured using an EVOM epithelial voltmeter equipped with an Endohm electrode (World Precision Instruments, Sarasota, Fla.) both before and after experimentation. In addition, marker compounds were selected to characterize the monolayers. Specifically, mannitol, an indicator of paracellular transport, and poly(ethylene glycol)-4000, a nonabsorbable marker, were used as indicators of the barrier properties of the monolayers. Tritium exchange between the $^3$H-labeled compounds and H2O was quantified by air-drying 100 µl aliquots of solutions containing the radiolabeled compound at their respective experimental concentrations in a fume hood overnight. The remaining radioactivity was compared to controls made before evaporation.

Caco-2 Cell Transport Studies An Ussing-type diffusion chamber system (Harvard Apparatus, Natick, Mass.) was used to perform transport studies. The apical solution was a MES Ringer's buffer (pH 6.5) consisting of 114.0 mM NaCl, 5.0 mM KCl, 1.1 mM MgSO$_4$, 1.25 mM CaSO$_4$, and 15 mM 2-(N-morpholino)ethanesulfonic acid (MES). The basolateral solution was a Ringer's buffer (pH 7.4) consisting of 114.0 mM NaCl, 5.0 mM KCl, 1.65 mM Na$_2$HPO$_4$, 0.3 mM NaH$_2$PO$_4$, 25 mM NaHCO$_3$, 1.1 mM MgSO$_4$, and 1.25 mM CaSO$_4$. Both buffers contained 25 mM glucose and were adjusted to 290 mOsm/kg using a vapor pressure osmometer (Wescor Inc, Logan, Utah). For transport experiments using filters with cell monolayers, the inserts were rinsed with Ringer's buffer containing 25 mM glucose three times over a 20 min period at room temperature. The TEER was measured for each monolayer before it was mounted onto the diffusion chamber, which was pre-warmed to 37° C. by placement on the heating blocks. The volume of each half-chamber was 5 ml and the surface area of the Snapwell filters available for drug transport was 1 cm$^2$.

The fluids in the chambers were circulated using a gas lift mechanism with 5% $CO_2$/95% $O_2$; flow rate was adjusted to 10 ml/min and monitored using a J&W ADM2000 gas flow meter (Fisher Scientific, Fair Lawn, N.J.). The donor solution consisted of radiolabeled permeant in the apical buffer [apical (AP) to basolateral (BL) study]. Starting at 30 min, samples were taken from the receptor chamber every 15 min until the end of the experiment (105 min). A minimum of three monolayers was used to determine the permeability of test compound in each study and sample analysis was performed using scintillation counting (Perkin Elmer, Gaithersburg, Md.).

CHO Cell Uptake Studies. CHO cells transiently transfected with hSMVT (CHO/hSMVT) were washed twice with 25 mM uptake buffer, containing 25 mM Hepes/Tris pH 7.5, 140 mM NaCl, 5.4 mM KCl, 1.8 $CaCl_2$, 0.8 mM $MgSO_4$ and 5 mM glucose. Subsequently, the cells were incubated with the permeant at 37° C. for 10 minutes. Uptake was stopped by washing the cells thrice with ice-cold buffer. Non-specific uptake was measured in parallel experiments with the control pSPORT vector-transfected CHO cells. Finally, the cells were solubilized by 0.1% v/v Triton X-100, and 0.6 ml was used for scintillation counting. From the remaining volume, 10 μl of solution was taken from each well and protein concentration was determined using the Bio-Rad reagent according to the manufacturer's instructions. Bovine serum albumin was used as the standard.

Concentration Dependence of biotin-PEG-3400. The concentration dependence of biotin-PEG-3400 (0.6-100 μM) was determined by evaluating its AP to BL or absorptive transport across Caco-2 cell monolayers. The effective permeability, Pe, (cm/sec) was determined using the equation $Pe=dC/dt*Vr/AC_0$, where Vr is the volume of the receptor chamber (5 ml), A is the surface area of the filter (1 $cm^2$), $C_0$ is the initial drug concentration, and dC/dt is the flux (J) determined by the linear slope of receptor drug concentration versus time plot after correcting for dilution. PEG-3350 (0.1-100 μM) was used in the control experiments. The uptake of biotin-PEG-3400 (0.05-12.5 μM) was also studied in CHO/hSMVT cells with simultaneous determination in control CHO/pSPORT cells. PEG-3350 (0.05-10 μM) uptake in CHO/hSMVT cells was determined in the control studies. The Michaelis-Menten kinetic parameters of Caco-2 and CHO cell transport were then estimated using non-linear regression.

Inhibition of biotin-PEG-3400. The involvement of SMVT in the Caco-2 cell monolayer transport of biotin-PEG-3400 was investigated through inhibition studies that were performed by co-incubating biotin-PEG-3400 with competitive substrates of SMVT in the donor solution (AP) of the diffusion chambers. The tritiated carrier mimic was co-incubated with 10 μM and 20 μM concentrations of biotin, structural analogues biocytin and desthiobiotin and a transport competitor, biotin-PEG-biotin.

Concentration Dependence of PEG:(RI-K(biotin)-Tat9)$_8$ Conjugate. Following the permeability determinations of biotin-PEG-3400, the absorptive transport of PEG:(RI-K(biotin)-Tat9)$_8$ (0.1-30 μM) was evaluated across Caco-2 cell monolayers and permeability values determined. Nonbiotinylated PEG:(RI-K-Tat9)$_8$ (0.1-30 μM) was used in the control studies. The uptake of PEG:(RI-K(biotin)-Tat9)$_8$ conjugate (0.003-30 μM) was also studied in CHO/hSMVT cells. Conjugate uptake in CHO/pSPORT cells and uptake of PEG:(RI-K-Tat9)$_8$ (0.04-45 μM) in CHO/hSMVT were estimated in the control experiments.

Inhibition of PEG:(RI-K(biotin)-Tat9)$_8$ Conjugate. The uptake of PEG:(RI-K(biotin)-Tat9)$_8$ conjugate (0.1 μM) was studied in CHO/hSMVT cells in the presence of biotin, pantothenic acid, desthiobiotin, biocytin, biotin-PEG-3400 and biotin-PEG-biotin (50 μM) and compared to the control (uptake of PEG:(RI-K(biotin)-Tat9)$_8$ alone).

Data Analysis. The Michaelis-Menten kinetic parameters for the Caco-2 cell monolayer transport studies were estimated by performing weighted non-linear regression with Scientist software (MicroMath, Utah) using the following equation: $P_e=P_m+P_c/(1+C/K_m)$, where $P_e$ is the effective permeability of the substrate transported, C is the substrate concentration and $P_m$ and $P_c$ represent the passive and carrier-mediated component of the permeability. The data from inhibition studies were transformed into Lineweaver-Burke plots to determine the nature of the inhibition process (competitive, non-competitive). Ki values were determined using the equation
$P_e=P_m+(P_c/(C+K_m(1+I/K_i)))$, where $P_e$, the effective permeability (cm/s), is related to the maximum flux, $J_{max}$, drug concentration, C, concentration of the inhibitor, I, affinity constant, $K_m$, and the estimated inhibition constant, $K_i$. Data used for the above plots were weighted using $1/S.E.M.^2$. The kinetic parameters for CHO cell studies were estimated by performing non-linear regression using the equation $J=J_{max}*[C]/(K_m+[C])$, where J is the rate of permeant uptake, Jmax is the maximal uptake velocity and [C] is the substrate concentration. Data were weighted using $1/S.E.M.^2$. Statistical analyses were performed using Jandel SigmaStat, version 2.03. One-way analysis of variance was used to test the difference in the mean values of uptake using $p<0.05$ as the significance level for all tests.

Results: Caco-2 Cell Monolayer Validation Studies. The Caco-2 cell validation studies were performed to determine the functional integrity of the monolayers. TEER measurements indicated values of 300-350 $\Omega cm^2$, both before and after the transport experiments. The permeability of mannitol (5 μM) was determined to be 1.42 (±0.28)×$10^{-6}$ cm/sec and that for PEG-3350 was ~1×$10^{-6}$ cm/sec. These results indicate that the cell monolayers were not leaky or damaged. The studies performed to measure tritium exchange indicated no significant differences in the radioactivity of the air-dried samples when compared to the controls, indicating the absence of proton transfer. For all the compounds studied, concentrations in the receptor chamber were linear with time for the duration of the experiments.

Figure 11:
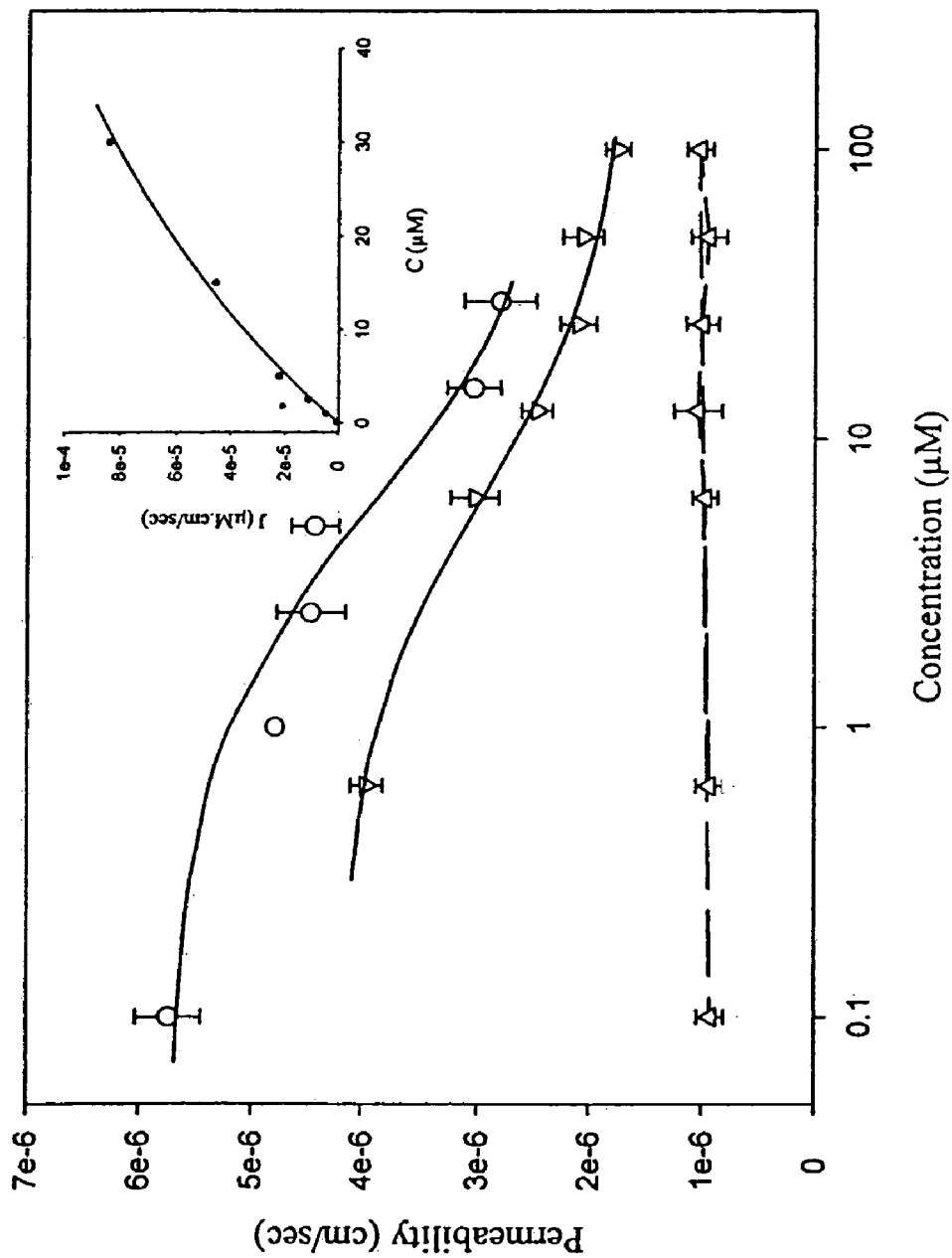
FIG. 11 depicts the absorptive transport of biotin-PEG-3400 (∇), PEG-3350 (Δ), and PEG:RI-K(biotin)-Tat9)8 (○) across Caco-2 cell monolayers.

Biotin-PEG-3400 Transport Studies: Concentration Dependence of biotin-PEG-3400. The absorptive transport of PEG-3350 across Caco-2 cell monolayers was low (~1×$10^{-6}$ cm/sec), not concentration dependent and the probable result of passive diffusion. However, biotin-PEG-3400 transport across Caco-2 cells followed concentration dependent and saturable kinetics (FIG. 11). The Michaelis-Menten kinetic parameters for biotin-PEG-3400 transport are presented in Table V.

TABLE V

Michaelis-Menten parameters for biotin-PEG-3400 and PEG:RI-K(biotin)-Tat9 transport across Caco-2 and CHO/hSMVT cells.

| Cell System | Kinetic Parameter | Biotin-PEG-3400 | PEG:(RI-K(biotin)-Tat9)$_8$ |
|---|---|---|---|
| Caco-2 Cell Monolayer Transport | $P_c$ (*$10^{-6}$) (cm/sec) | 2.56 (0.11) | 3.39 (0.53) |
| | $P_m$ (*$10^{-6}$) (cm/sec) | 1.61 (0.07) | 2.18 (0.57) |
| | $K_m$ (μM) | 6.61 (1.25) | 6.13 (3.74) |
| CHO/hSMVT Cell Uptake | $J_{max}$ (pmol/mg protein/10 min) | 23.46 (5.04) | 1288.18 (54.25) |
| | $K_m$ (μM) | 1.26 (1.01) | 8.19 (0.96) |

$P_c$: Carrier-Mediated Permeability Component;
$P_m$: Passive Permeability Component;
$J_{max}$: Maximum Uptake Rate;
$K_m$: Michaelis Constant.
Numbers in parentheses represent Standard Deviation (S.D);
n = 3.

The low $K_m$ (6.61 μM) value for biotin-PEG-3400 transport indicated the potential involvement of a high affinity, low capacity transporter system. The uptake of biotin-PEG-3400 in CHO/hSMVT cells was concentration dependent and saturable (see FIG. 2 described above) with estimated $K_m$ and $J_{max}$ values of 1.26±1.01 µM and 23.46±5.04 pmol/mg protein/10 min, respectively. Transformation of the uptake data into an Eadie-Hofstee plot (r=0.9047) (FIG. 2 inset) indicated that the kinetics of biotin-PEG-3400 matched a single saturable carrier model. Biotin-PEG-3400 uptake was significantly lower (p<0.01) in the control CHO/pSPORT cells (4.22 pmol/mg protein/10 min) compared to CHO/hSMVT cells, but higher than PEG-3350 uptake in CHO/hSMVT cells (<1 pmol/mg protein/1 min) (FIG. 2).

Figure 12:
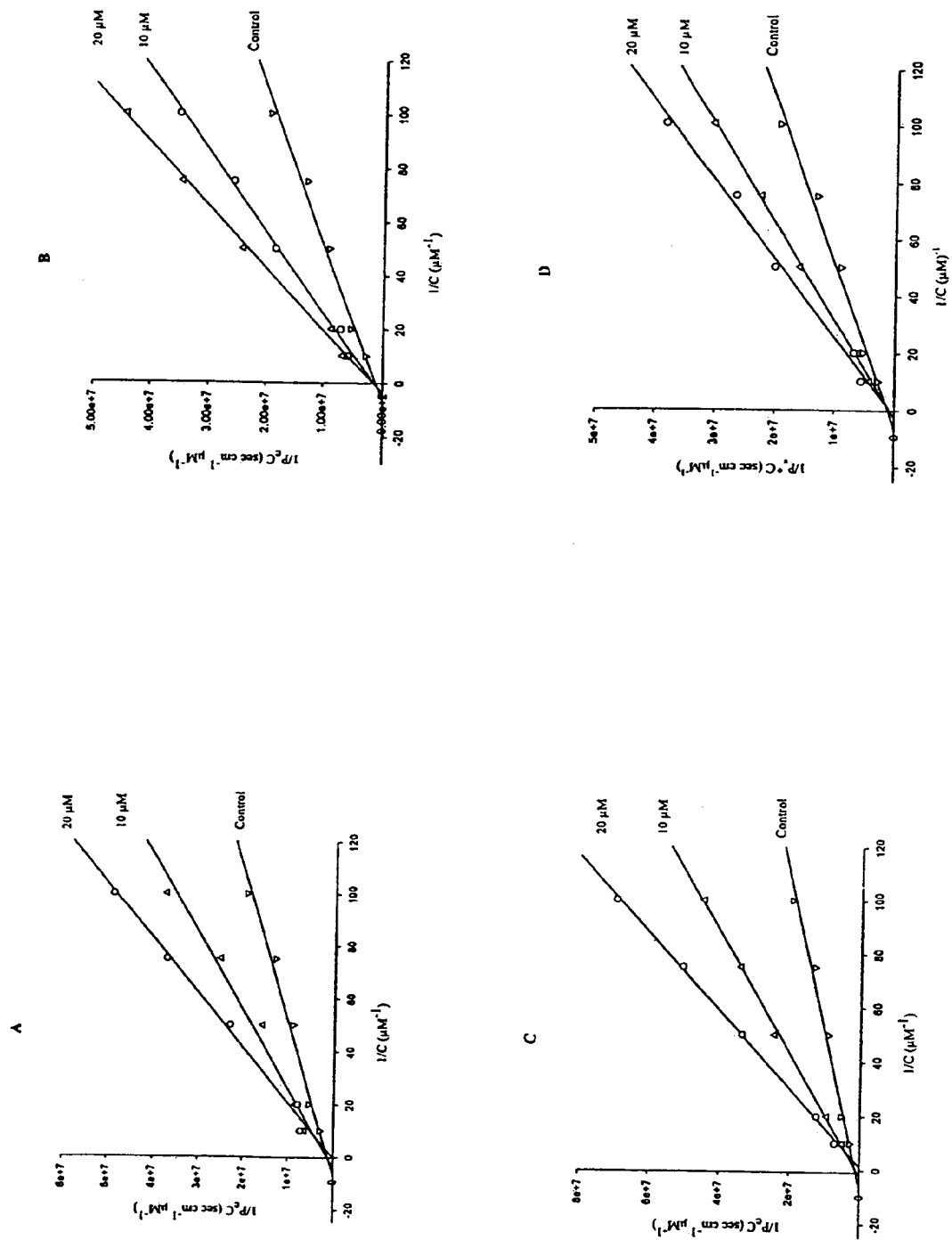
FIG. 12 A-D show Lineweaver-Burke plots of biotin-PEG-3400 transport across Caco-2 cell monolayers in: the presence of A) biotin, B) biocytin, and C) desthiobiotin, and D) biotin-PEG-biotin, used as inhibitors at 10 and 20 μM.

Inhibition of biotin-PEG-3400. Biotin-PEG-3400 inhibition studies across Caco-2 cell monolayers were performed with known SMVT substrate biotin, its structural analogues desthiobiotin and biocytin, and the competitor, biotin-PEG-biotin. The Lineweaver-Burke plots suggested competitive inhibition of biotin-PEG-3400 transport by biotin (FIG. 12A), desthiobiotin (FIG. 12B), biocytin (FIG. 12C), and biotin-PEG-biotin (FIG. 12D) with inhibition constant (Ki) values of 6.78 µM, 11.47 µM, 14.01 µM, and 19.08 µM, respectively.

Figure 13:
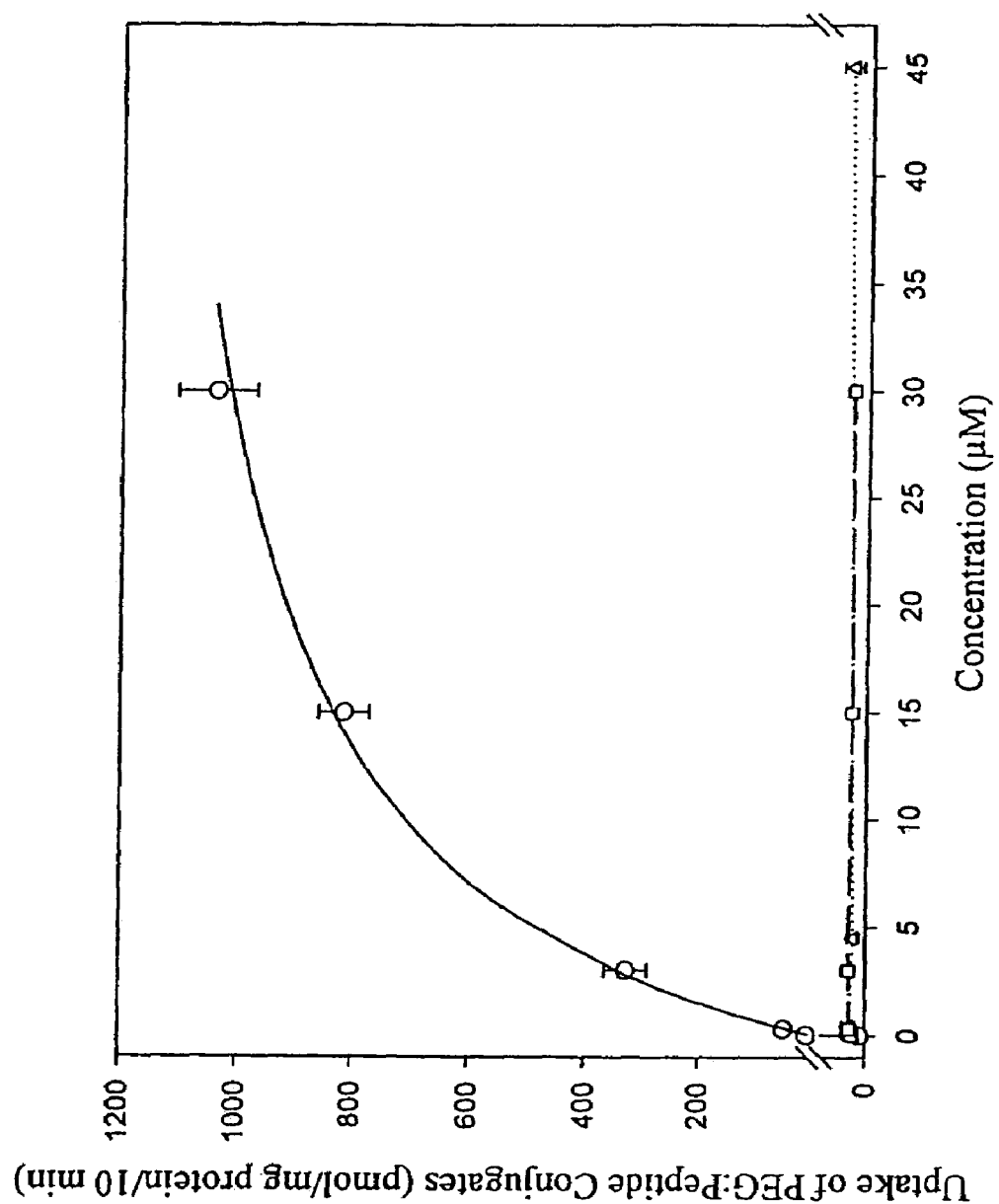
FIG. 13 shows the uptake of PEG:(RI-K(biotin)-Tat9)$_8$ in CHO/hSMVT cells (○), CHO/pSPORT cells (□) and PEG: (RI-K-Tat9)$_8$ uptake in CHO/hSMVT (Δ) cells.

PEG:(RI-K(biotin)-Tat9)$_8$ Conjugate Transport Studies: Concentration Dependence of PEG:(RI-K(biotin)-Tat9)$_8$ Having established the feasibility of transporting a large biotinylated PEG molecule by means of SMVT, the transport of PEG:(RI-K(biotin)-Tat9)$_8$ conjugate across Caco-2 cell monolayers was examined. The Caco-2 cell absorptive permeability of PEG:(RI-K(biotin)-Tat9)$_8$ conjugate entailed carrier-mediated and saturable transport kinetics (FIG. 11). The Michaelis-Menten kinetic parameters for PEG:(RI-K(biotin)-Tat9)$_8$ transport are presented in Table I above. In the control experiments, transport of PEG:(RI-K-Tat9)$_8$ conjugate was extremely low (<10–7 cm/sec) and barely detectable. Based on the low $K_m$ value (6.13 µM) for PEG:(RI-K(biotin)-Tat9)$_8$ transport, the role of SMVT was implicated and uptake studies in transfected CHO cells were performed. PEG:(RI-K(biotin)-Tat9)$_8$ uptake in CHO/hSMVT cells exhibited concentration dependent and saturable kinetics with estimated $K_m$ and $J_{max}$ values of 8.19 µM and 1288.18 pmol/mg protein/10 min, respectively (FIG. 13). In the control studies, uptake of PEG:(RI-K(biotin)-Tat9)$_8$ in CHO/pSPORT cells and PEG:RI-K-Tat9 uptake in CHO/hSMVT cells were extremely low (<1 pmol/mg protein/10 min).

Figure 14:
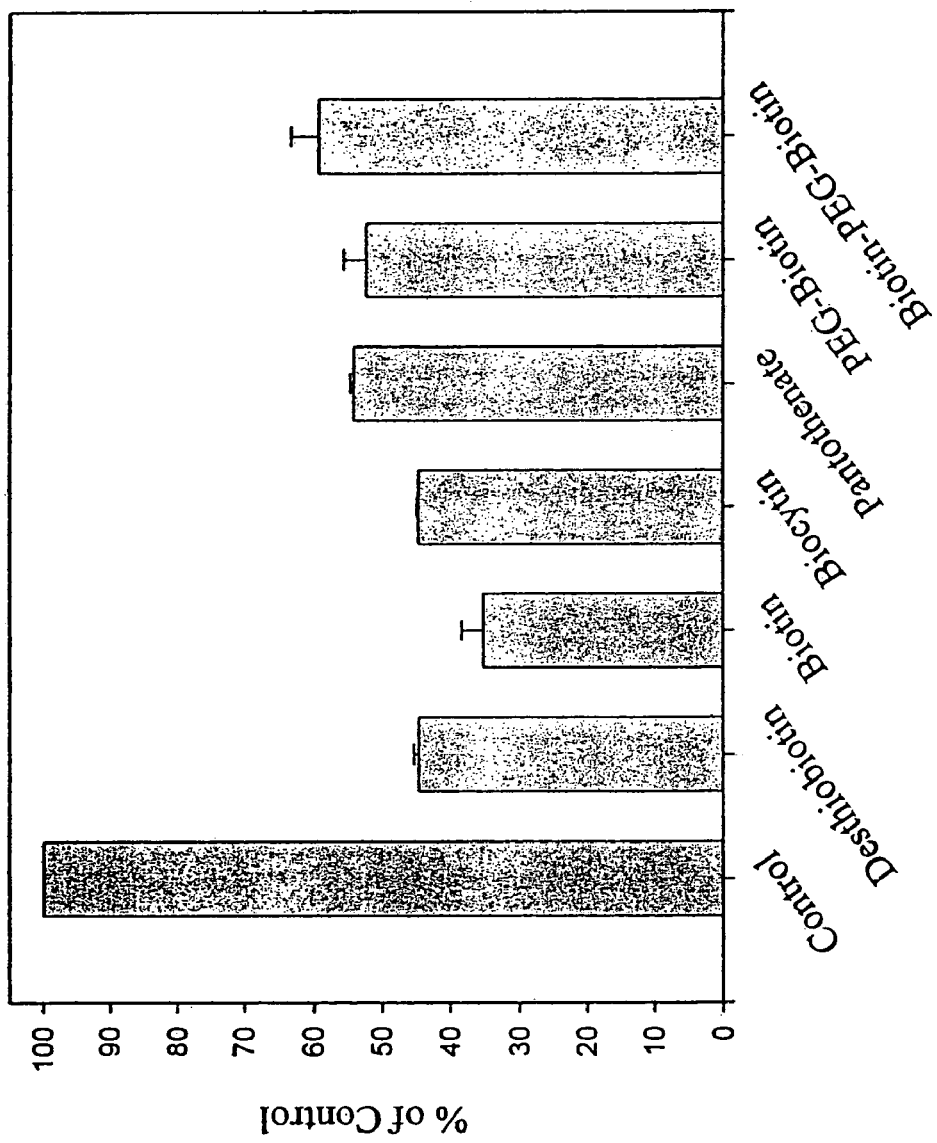
FIG. 14 depicts the uptake of 0.1 μM PEG:(RI-K(biotin)-Tat9)$_8$ in CHO/hSMVT cells measured for 10 minutes in the presence of 50 μM of SMVT substrates.

Inhibition of PEG:(RI-K(biotin)-Tat9)$_8$ Conjugate. Uptake of PEG:(RI-K(biotin)-Tat9)$_8$ in CHO/hSMVT cells was significantly lower (p<0.05) in the presence of known SMVT substrates biotin, pantothenic acid, desthiobiotin, biocytin and compounds evaluated in this study, biotin-PEG-3400 and biotin-PEG-biotin, compared to the control (PEG:(RI-K(biotin)-Tat9)$_8$ alone ~11.44 pmol/mg protein/10 min) (FIG. 14).

EXAMPLE 4

Transport of Conjugates Across Endothelial Cells

Isolation and culture of BBMECs. Bovine Brain Microvessel Endothelial Cells (BBMECs) were used as an in vitro model of BBB. BBMECs were isolated from bovine brain by a two-step enzymatic method and the cells were cultured on collagen coated Transwell™ plates or polystyrene plates in an atmosphere of 95% air and 5% $CO_2$ at 37° C. Transendothelial electrical resistance (TEER) and several molecular markers were used to validate the integrity of the cell culture system.

Characterization of Biotin transporter. The molecular expression of SMVT in BBMECs was determined using RT-PCR. Upon confluency of BBMEC monolayers, concentration dependence (1-1000 µM) and sodium dependence (0-130 µM) of biotin uptake were determined at 37° C. Further, inhibition studies were performed by coincubating biotin with various derivatives and structural analogues such as pantothenic acid, desthiobiotin, iminobiotin, diaminobiotin and biocytin at different concentrations.

Transport and Uptake of Biotin Conjugated Peptides and polymers. Transport and uptake of RI-K-Tat9, and RI-K(biotin)-Tat were studied using BBMECs. The cells were cultured on 12-well Transwell™ filters for 7-8 days and transport was evaluated. Uptake studies were performed similar to those employed for biotin. All studies were performed at 37° C. Transport and cellular uptake of biotin-PEGs having 3- or 8-arms at M.W. $10^4$ gmol$^{-1}$ or linear form at M.W. 3350 was determined and compared with non-conjugated PEG controls.

Figure 16:
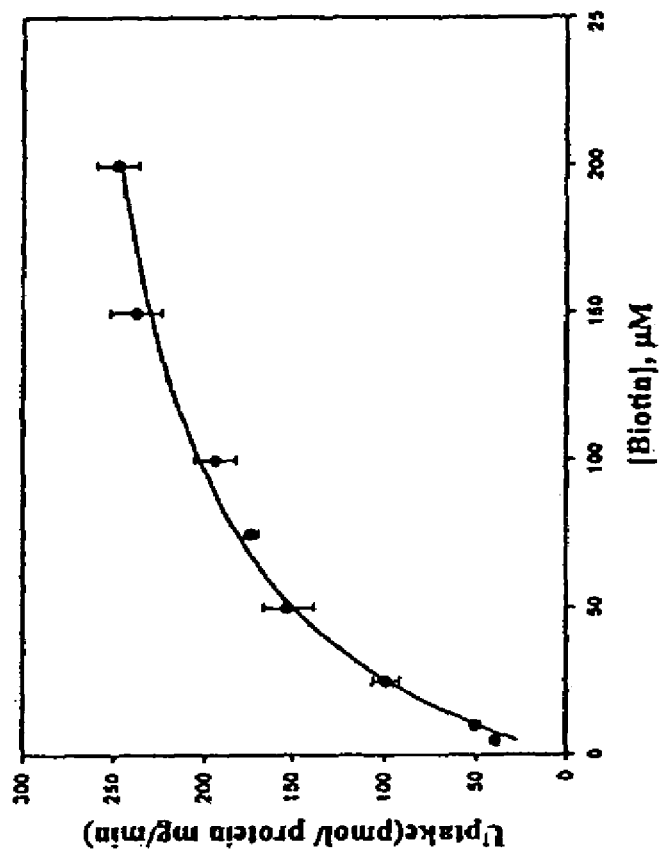
FIG. 16 shows the concentration dependence of biotin uptake in BBMECs.
Figure 17:
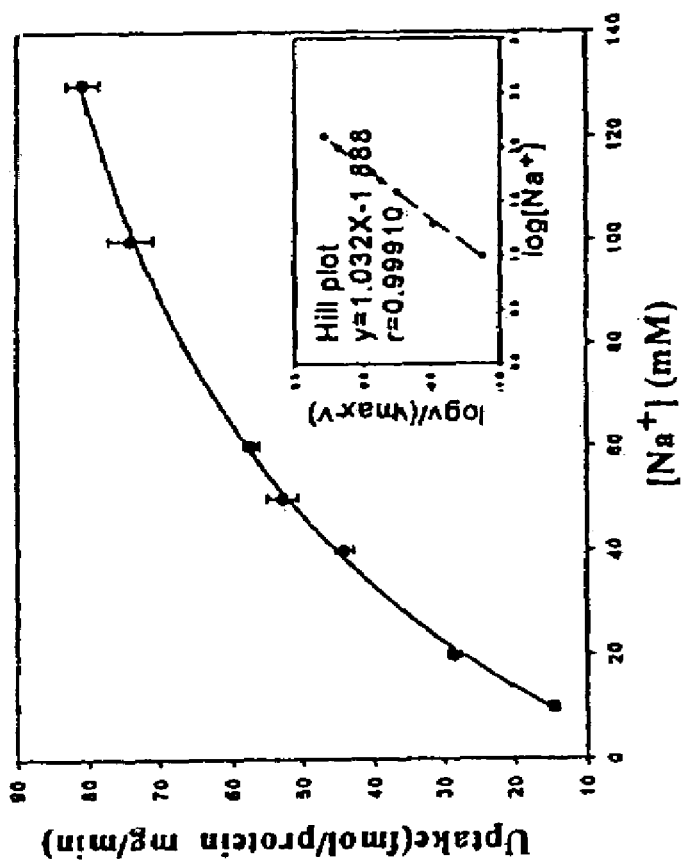
FIG. 17 depicts the influence of sodium ion on biotin uptake by BBMECs.

The cells were confirmed to be endothelial in nature by the expression of Factor VIII-related antigen. RT-PCR studies indicated the molecular expression of SMVT (ca. 400 bp) in BBMECs (Data not shown). The SMVT-mediated transport of biotin in BBMECs was concentration dependent ($K_m$: 54.6 µM) and saturable. The influence of sodium concentration on biotin transport was studied and the Na$^+$-biotin coupling ratio for SMVT was determined to be 1 based on the Hill equation (FIG. 16). Desthiobiotin and pantothenic acid inhibited the uptake of biotin significantly while the inhibitory effect of iminobiotin and diaminobiotin were very weak. Transport and uptake of RI-K(biotin)-Tat9 were concentration dependent (~$K_m$: 40 µM) and saturable (FIGS. 18 and 19) while the apparent permeability ($P_{app}$) RI-K-Tat9 was passive and low ($P_{app}$: 7.3×10$^{-6}$ cm/sec). The permeability and cellular uptake of biotin-conjugated PEGs and control PEGs into BBMECs were determined. The permeability of Biotin-PEG-3350 is 2.4-fold greater than the permeability of PEG-3350. This phenomenon is more obvious when highly branched PEGs were used. The permeabilities of biotin conjugated 3- and 8-arms PEGs were 4.7- and 16-fold greater, respectively, than the permeabilities of their controls. Similar results were observed in the cellular uptake studies.

EXAMPLE 5

Brain Uptake and Distribution of Biotin-PEG

This in vivo study was performed in order to investigate the uptake of biotin-PEG to the brain. In addition, plasma level as well as distribution into other organs such as liver, heart, spleen and kidney were evaluated. Plasma concentration and uptake of Biotin-PEG (8 arm/10 kDa) to various organs were evaluated following a single i.v. dose (0.1 mg/100 g body weight) using mice, as an in vivo model. FIG. 19A shows the brain uptake of the conjugate as a function of time. The elimination half life of the conjugate was estimated to be 50 minutes approximately based on the plasma concentration-time profile. Among the organs analyzed for conjugate distribution, kidneys showed the highest accumulation (FIG. 19B).

EXAMPLE 6

Conjugates Bearing Multiple Formyl-Methionyl Peptides Display Enhanced Binding to but Not Activation of Phagocytic Cells In the following experiment, a specific chemotactic peptide, N-formyl-methionine-leucine-phenylalanine (fMLP), was used to evaluate potential transport of therapeutic agents into macrophages and other phagocytes, which possess a high-affinity receptor for fMLP. The specificity of targeting is achievable because related low affinity receptors and orphan receptors are more widely distributed.

Materials. N-Formyl-methionine-leucine-phenylalanine (fMLF) peptide was purchased from Sigma (St. Louis, Mo.). Radioactive [$^{45}$Ca]calcium chloride (specific activity 16 mCi/mg) and fML[$^{3}$H]F (40 Ci/mmol) were from DuPont-NEN Research Products (Boston, Mass.). The human cells used in this study (HL-60 and Jurkat T-cells) were purchased from the American Type Culture Collection (Manassas, Va.). Branched amino-PEGs with three (10 kDa), four (10 kDa) or eight arms (20 kDa) and α,ω-diamino-PEG (3.4 kDa) were purchased from Shearwater Polymers (Huntsville, Ala.). Dichloromethane (DCM) and N,N-dimethyl formamide (DMF) were purchased from Fisher Scientific (Pittsburgh, Pa.). Trifluoroacetic acid (TFA), diisopropylcarbodiimide (DIPC) and p-toluenethiosulfonic acid (PTSA) were obtained from Aldrich Chemical (Milwaukee, Wis.). N-Hydroxysuccinimide-digoxigenin (NHS-DIG) was obtained from Boehringer-Mannheim (Indianapolis, Ind.). Fluorescamine was a gift from S. Udenfriend. Hanks' balanced salt solution (HBSS) and RPMI tissue culture medium were purchased from GIBCO (Grand Island, N.Y.).

Quantitation of primary amino groups. Fluorescamine (Udenfriend et al., 1972) was used to monitor conversion of primary amines to amides. A fluorescence signal is obtained only by reaction with primary amines and not with amides or with secondary or aromatic amines. To each well of the 96-well plates, 0.1 mL of sample was added. Then 0.05 mL of 0.2 M borate buffer (pH 9.3) was added to each well, and 0.05 mL of fluorescamine (0.5 mg/mL in acetonitrile) was added and mixed immediately. The fluorescence intensity was measured at an excitation wavelength of 390 nm and emission wavelength of 475 nm.

Synthesis of Linear PEG-Aspartate Copolymer. This carrier copolymer was prepared by copolymerization of tBoc-aspartic acid and α,ω-diamino-PEG (3400 Da), using a modification of previous methods (Nathan et al., 1993; Poiani et al., 1994). The tBoc group was removed by treatment with TFA, thereby providing primary amino groups (—NH$_2$) for attachment of fMLF. Copolymer size was determined by size exclusion chromatography using PEG-tyrosine molecular weight standards prepared by us. The molecular weight was estimated to be 29 kDa. The structure of the resulting copolymer (m~8, n~75) is:

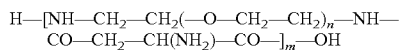

Conjugation of PEG-aspartate copolymer with fMLF and DIG. Linear PEG-aspartate (PEG/A) copolymer (about 10 mg) was reacted with 7-fold excess (relative to amino groups) of fMLF peptide, 3.5 molar excess of DIPC, 0.5 equivalent of PTSA and 4-dimethylaminopyridine (4-DMAP) in DMF:DCM (1:1 v/v). The total volume of the reaction was adjusted to 1 mL. The reaction mixture was incubated at room temperature for 24 hours with gentle stirring. Then the polymer was precipitated with 10 volumes of ice-cold ethyl ether and dissolved in 90% phosphate-buffered saline (PBS) pH=7.4, 10% acetonitrile. The unreacted peptide was separated from polymer by ultrafiltration with Microcon 10 (molecular weight cut-off=10 kDa Amicon/Millipore, Inc., Bedford, Mass.). The retentate was dried and dissolved in PBS. The extent of peptide conjugated to the polymer was estimated using the fluorescamine assay. Separately, 4 mg of PEG/A or 4 mg of PEG/A-fMLF were reacted with 1 mg of NHS-DIG, dissolved in DMSO, in 0.5 μL of PBS, adjusted with NaOH to pH 8.0, with stirring overnight. The products were precipitated with ether, dissolved in PBS and separated from the unreacted reagent by ultrafiltration with Microcon 10. The products were PEG/A-fMLF$_4$ and PEG/A-fMLF$_4$-DIG$_4$, and PEG/A-DIG$_8$.

Conjugation of fMLF with Branched (B) PEG. Addition of fMLF to the 8-arm branched amino-PEGs was accomplished in a similar manner as above. In order to achieve a range of molar ratio of fMLF conjugated to the copolymer, three sets of reactions with 14, 8 and 2-fold excess fMLF were set up. Fluorescamine assay was used to determine the average extent of conjugation of fMLF on the polymer, which was 8 (100%), 5.5 (68%) and 1.1 (14%) fMLF residues per polymer, respectively, for each reaction. These products are denoted B8-PEG-fMLF$_8$, B8-PEG-fMLF$_{5.5}$ and B8-PEG-fMLF$_{1.1}$, respectively. Similarly, a 14-fold molar excess of fMLF was used for reactions with 3-arm and 4-arm branched amino-PEGs to achieve 100% coupling, yielding B3-PEG-fMLF$_3$ and B4-PEG-fMLF$_4$.

Competitive Receptor Binding Assay. HL-60 cells were propagated in RPMI 1640 supplemented with 2 mM L-glutamine and 10% (v/v) heat-inactivated fetal bovine serum, and were subcultured every 3 days at a ratio of 1:4. Cells were grown at 37° C. in an atmosphere of 5% CO$_2$. Dimethyl sulfoxide (DMSO, 1.3%) was added to the culture (3×10$^5$ cells/mL) 48 h before the binding assay to initiate cellular differentiation. Differentiated HL-60 cells (2×10$^5$) were washed with PBS, pH 7.4, and resuspended in 1.77 mM KH$_2$PO$_4$, 8.0 mM Na$_2$HPO$_4$, 0.117 M NaCl, 0.15 mM CaCl$_2$, 0.5 mM MgCl, 1% bovine serum albumin (binding buffer) with fML[$^3$H]F (30,000 cpm) and unlabeled fMLF (0.1 nM-200 nM) or conjugate. The cells were incubated for 15 min at 37° C. with gentle shaking. They were collected by centrifugation at 3,000 g for 5 min at room temperature. The supernatant was removed and cells were resuspended in 0.1 mL of binding buffer and carefully added to the very top of tubes (Denville Scientific, South Plainfield, N.J., catalog #C19002) that contained 0.3 mL of 10% sucrose. They were centrifuged for 5 min. The cells settled to the bottom and any unbound ligand remained in the middle of the tube. The tubes were placed in dry ice for 5 min, and then their bottoms were cut off to collect the cells. Cell-bound and free radioactivity were determined by liquid scintillation counting.

Intracellular Calcium Assay. HL-60 cells (2×10$^5$ cells/mL) were grown in the presence of 1.3% DMSO for 5 days. For each time course experiment, 2×10$^6$ cells were resuspended in 5 mL of HBSS containing 2 mCi/mL of $^{45}$CaCl$_2$ as the sole source of calcium. After 90 min incubation at 37° C., cells were washed twice as above with cold HBSS. Vesicle-associated and cytoplasmic $^{45}$Ca were measured prior to and at 1, 2, 3, 4, 5 and 10 min after the addition of the fMLF or conjugated compounds. The EC$_{50}$ for cellular activation is the concentration of each compound tested resulting in 50% maximal stimulation of calcium efflux by this assay. Cell pellets were treated with 0.5% Triton X-100/0.1 M NaOH and centrifuged in tubes containing 0.3 mL of 10% sucrose and radioactivity associated with the pellets was measured; this represents vesicle-associated $^{45}$Ca. The top portion of the tube, which contained the cytoplasmic $^{45}$Ca was also measured. The peak level of transient increase in cytoplasmic calcium and decrease in vesicle-associated calcium represents efflux of calcium from intracellular storage compartments, that is stimulated by fMLF interaction with membrane receptors (Montero et al., 1994; Klinker et al., 1996; Azuma et al., 1996; Anderson and Mohamed Goolam, 1997).

Uptake by HL-60, Jurkat and Peritoneal Cells. Human Jurkat T-cell growth conditions were the same as for HL-60 cells, except that the subcultivation ratio was 1:3. Jurkat cells (2×10$^5$) or fully differentiated HL-60 cells were washed twice with PBS and incubated in binding buffer (see above) with conjugate for 30 min at 37° C. Each conjugate (1 µg, dissolved at a concentration of 333 nM) was used in these experiments. Cells were lysed, the membranes and cell debris were removed by centrifugation (5 min. at 14,000×g) and the enzyme-linked immunosorbent assay (ELISA) for DIG was performed on the supernatant as described below. In order to study primary peritoneal cells, BALB/c mice were injected in the peritoneal cavity with 5 µg of PEG/A-DIG$_4$-fMLF$_4$ (n=3 mice), or PEG/A-DIG$_4$ (n=4 mice). After 1 h, the cavity was flushed with medium and cells were collected and washed twice with cold PBS, as described above.

Cells were resuspended in 100 µL of PBS, containing 0.6% Tween 20, vortexed briefly and kept on ice for 30 min. Microscopic examination confirmed complete cell lysis. Uptake of DIG was determined by ELISA of the supernatant. Anti-DIG-Fab fragment and anti-DIG-horseradish peroxidase (POD) were purchased from Boehringer Mannheim. Anti-DIG-Fab (1 mg/mL) was diluted 1:100 and anti-DIG-POD (150 U/mL) was diluted 1:10,000. ELISA was performed according to the manufacturer's procedure. DIG content was proportional to the difference in absorbance at 495 nm and 450 nm. A standard curve for PEG/A-DIG$_4$ and PEG/A-fMLF$_4$-DIG$_4$ was included in each assay. In order to account for the potential different amounts of peritoneal cells from each mouse, the results were normalized to the amount of protein, as measured with the Bradford assay (BioRad, Hercules Calif.).

RESULTS Competitive Binding of fMLF Conjugates to Differentiated HL-60 Cells. In order to determine the effect of different numbers of targeting groups on polymer avidity for differentiated HL-60 cells, conjugates were tested for their binding activity, measured by their ability to compete with fML[$^3$H]F for cell binding. The HL-60 cells used for these experiments were differentiated for 48 hours with DMSO. HL-60 cells treated with DMSO for five days yielded similar results. However, HL-60 cells that were not subjected to a differentiation-inducing regimen did not bind to fMLP. HL-60 cells, which are derived from human promyelocytic leukemia cells, have the capacity to respond to many stimuli to differentiate into many cell types of the monocytic-granulocytic class. The categorization of the differentiated states by the nomenclature for normal cell types is somewhat arbitrary, since the cells tend to have properties that overlap these categories. Although. DMSO is considered to induce cells to differentiate along the granulocytic pathway, the final phenotype of these cells is not identical to normal granulocytes (reviewed by Collins, 1987). The functional properties of HL-60 differentiated cells are similar (although not identical) to neutrophils (Dahlgren et al., 1987). They are able to undergo azurophilic granule release and to generate O$_2$ (Seifert et al., 1992). Expression of the receptor for fMLF is one of the early events of differentiation of HL-60 cells and its presence is the only requirement for binding of fMLF to these cells (Prossnitz et al,. 1993).

Figure 20:
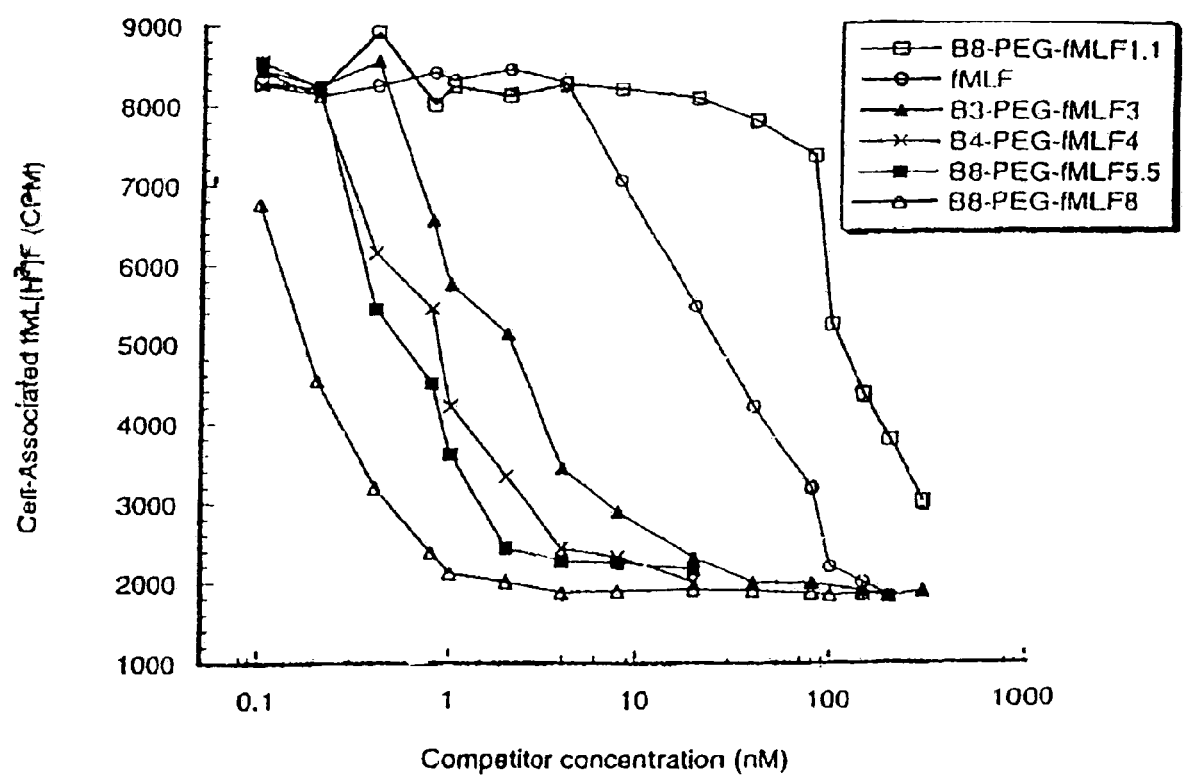
FIG. 20 depicts the competition of free and branched polymer-conjugated fMLF for binding to differentiated HL-60 cells.
Figure 21:
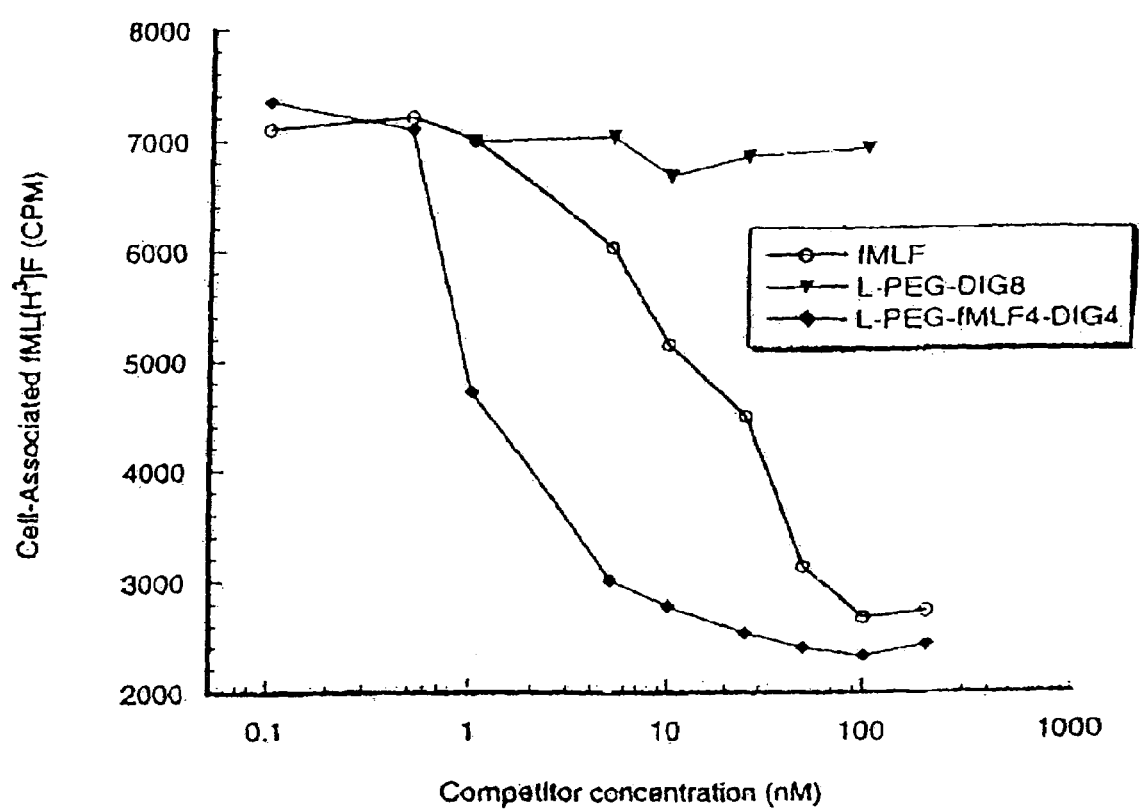
FIG. 21 shows the competition of free and linear polymer-conjugated fMLF for binding to differentiated HL-60 cells.

The polymers tested included PEG/A-fMLF$_4$, PEG/A-fMLF$_4$-DIG$_4$, PEG/A-DIG$_8$, B8-PEG-fMLF$_{1.1, 5.5}$ and $_8$, B4-PEG-fMLF$_4$ and B3-PEG-fMLF$_3$. FIGS. 20 and 21 show the result of competitive binding studies. The amount of fML[$^3$H]F was kept constant while the concentration of the conjugates was varied. The binding curves (FIGS. 20 and 21) show that the specific binding is about 75% of the total binding. The binding constant (Kd) estimated here for fMLF is 28 nM, which is close to that (33 nM) determined by Derian-et al. (1996). As can be seen in FIG. 20 and Table VI, the increased Kd of B8-PEG-fMLF$_{1.1}$ (190 nM) relative to the free fMLF peptide (28 nM) indicates that attachment to the polymer reduces the avidity of the peptide for binding to cellular receptors. However, polymers with multiple fMLF moieties attached showed increased avidity for differentiated HL-60 cells, with B8-PEG-fMLF$_8$ showing the lowest Kd (0.18 nM), and the greatest avidity relative to the number of fMLF peptides (Kd fMLF=0.18 nM 8=1.44 nM).

TABLE VI

| Competitor | Avidity Kd (nM) | Cell Activation EC$_{50}$ (nM) | Relative Avidity Kd/fMLP | Avidity Activation EC50/K$_d$ |
|---|---|---|---|---|
| fMLF | 28 | 4.7 | 28 | 0.168 |
| B8-PEG-fMLF$_{1.1}$ | 190 | — | 209 | — |
| B3-PEG-fMLF$_3$ | 1.9 | 9.6 | 5.7 | 5.05 |
| B4-PEG-fMLF$_4$ | 0.8 | 5.0 | 3.2 | 6.25 |
| B8-PEG-fMLF$_{5.5}$ | 0.5 | 5.3 | 2.75 | 10.6 |
| B8-PEG-fMLF$_8$ | 0.18 | 5.0 | 1.44 | 27.8 |
| PEG/A-fMLF$_4$ | 1.1 | ND | 4.4 | — |
| PEG/A-fMLF$_4$-DIG$_4$ | 1.2 | 5.9 | 4.8 | 4.92 |

The size or shape of the polymer does not seem to play a major role in avidity of binding, since the linear polymer with 4 copies of fMLF showed properties similar to its branched counterpart, both displaying a Kd of about 1 nM (Table VI). Furthermore, whether the other four potential attachment sites on the linear PEG/A were either unoccupied or were occupied with DIG, made little difference in the Kd (FIG. 21, Table VI). Thus, additional moieties such as therapeutic or diagnostic drugs may be added to the targeting polymer without compromising the binding avidity.

Figure 22:
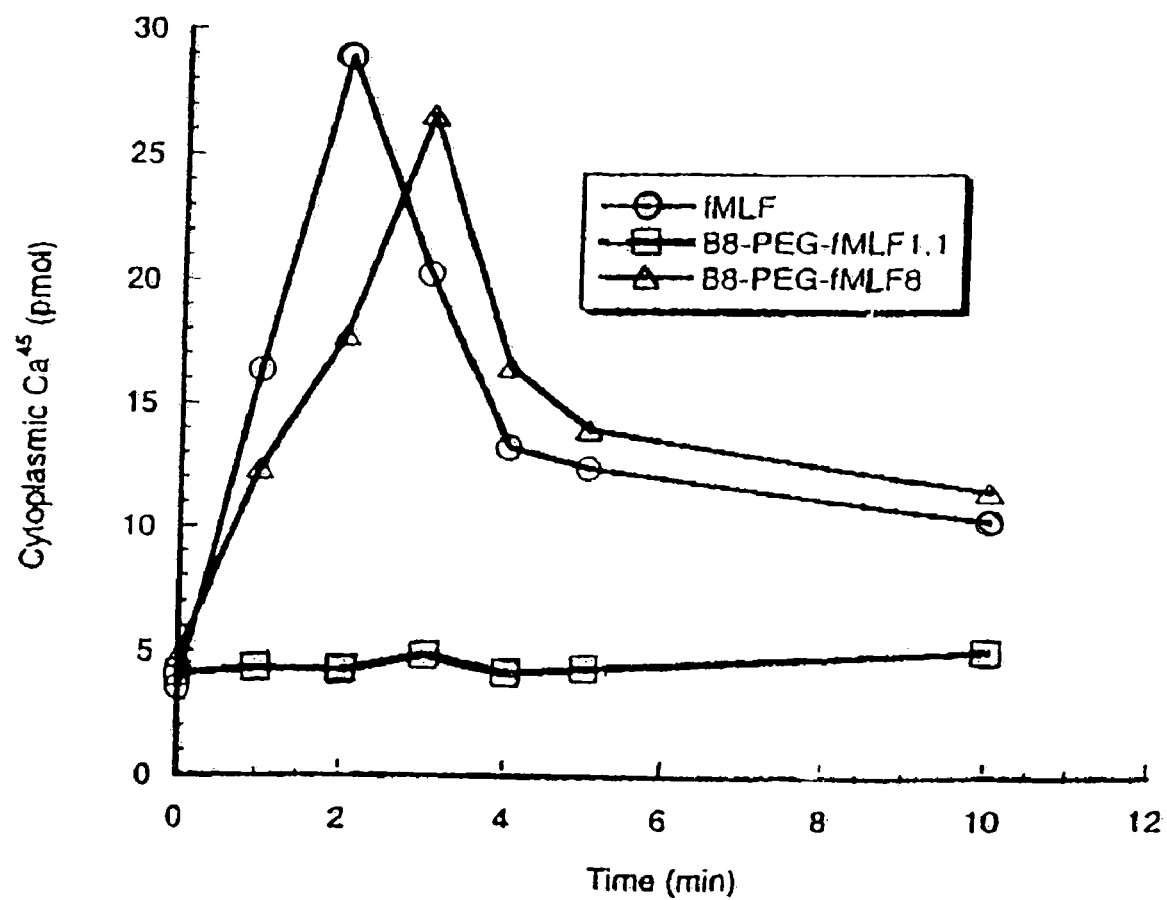
FIG. 22 is a time course of calcium release from intracellular stores in differentiated HL-60 cells.
Figure 23:
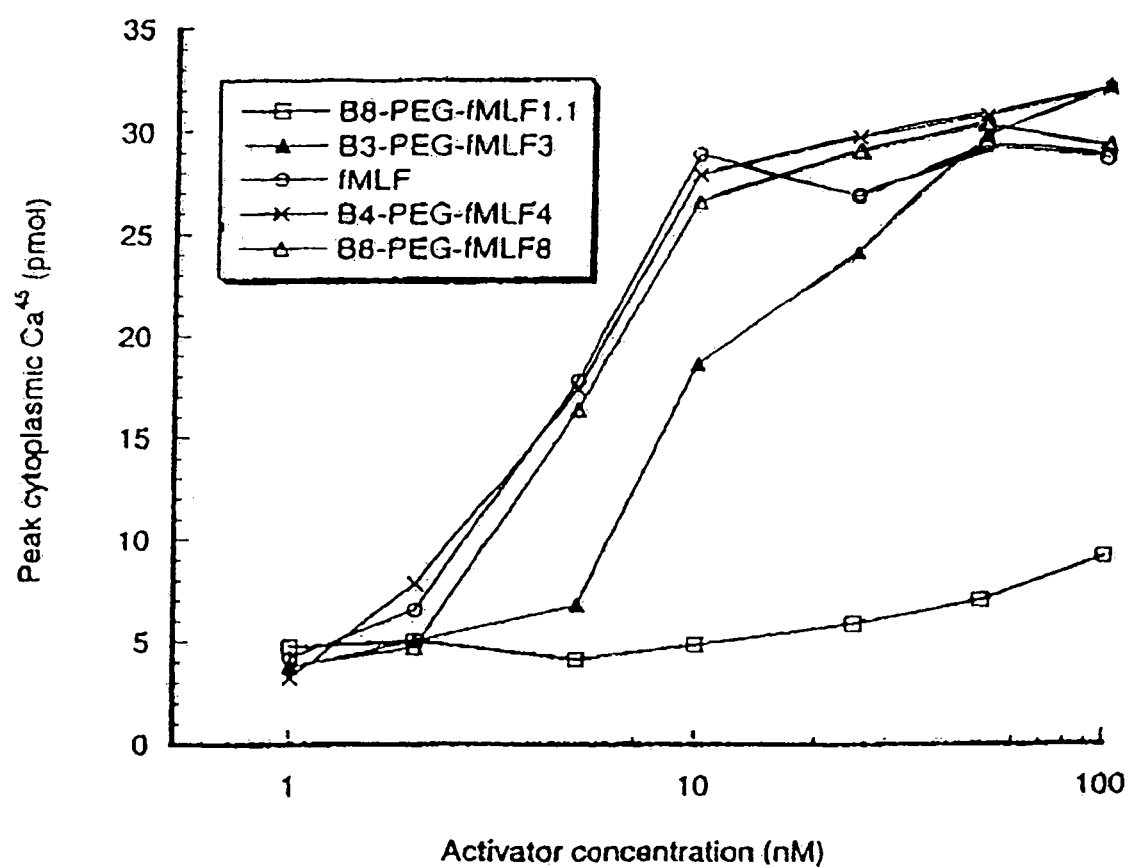
FIG. 23 shows the mobilization of calcium in differentiated HL-60 cells by fMLF and polymer conjugated-fMLF.

Cellular Activation of HL-60 Cells. Upon binding of the chemotactic peptide to the G-protein coupled receptor, one of the early events related to cellular activation is the release of Ca$^{++}$ from membrane-bound intracellular compartments into the cytoplasm (Azuma et al., 1996; Anderson and Mahomed Goolam, 1997; Prossnitz et al., 1999). The release of calcium is rapid, reaching its maximum value in 2-3 min followed by slow recovery to near basal level (FIG. 22). Similar kinetics of calcium release were observed in the response of differentiated HL-60 cells to free fMLF and to polymers bearing multiple fMLF moieties (FIG. 22). As was the case for binding to these cells, B8-PEG-fMLF$_{1.1}$ showed reduced ability relative to free fMLF to activate differentiated HL-60 cells, with virtually no flux of calcium even at 100 nM polymer. Activation also resembled binding in being enhanced by the presence of multiple fMLF moieties on a polymer, so that three fMLF residues on a polymer yielded readily detectable activation and four fMLF residues on a polymer were about as potent as free fMLF by this assay (FIG. 23 and Table 1). However, unlike the binding assay, the Ca++efflux into the cytoplasm did not further increase as the copy number of fMLF per polymer increased beyond 4 (FIG. 23 and Table 1). All of the conjugates with the copy number of fMLF greater than or equal to 4 showed similar half-maximal release of intracellular calcium (EC50) of about 5 nM of conjugate, which is the same as the EC50 value (4.7 nM) for the free peptide (Table 1). Thus, the presence of multiple ligands (>3) on PEG does not increase the activation potency as much as it increases binding avidity for macrophage-like cells.

Comparison of cellular binding and activation by various conjugates (Table 1) reveals that while no conjugate is quite as potent in activating differentiated HL-60 cells as is free fMLF, the avidity of conjugate for these cells increases with increasing number of fMLF moieties. This increase is most remarkable when expressed as Kd for the conjugate, but is still evident when a relative avidity is calculated per peptide, by multiplying the Kd of the conjugate by the average number of fMLF moieties that it carries. The ratio of avidity (1/Kd) to cellular activation ("toxicity") activity (1/EC50), measured by EC50/Kd, is 0.168 for free fMLF and increases from 5.05 to 27.8 for conjugates as number of fMLF moieties increases from 3 to 8. Although the effect of molecular shape was not systematically studied, note that both avidity and cellular activation activity were nearly the same for branched and linear polymers harboring 4 copies of fMLF.

Figure 24:
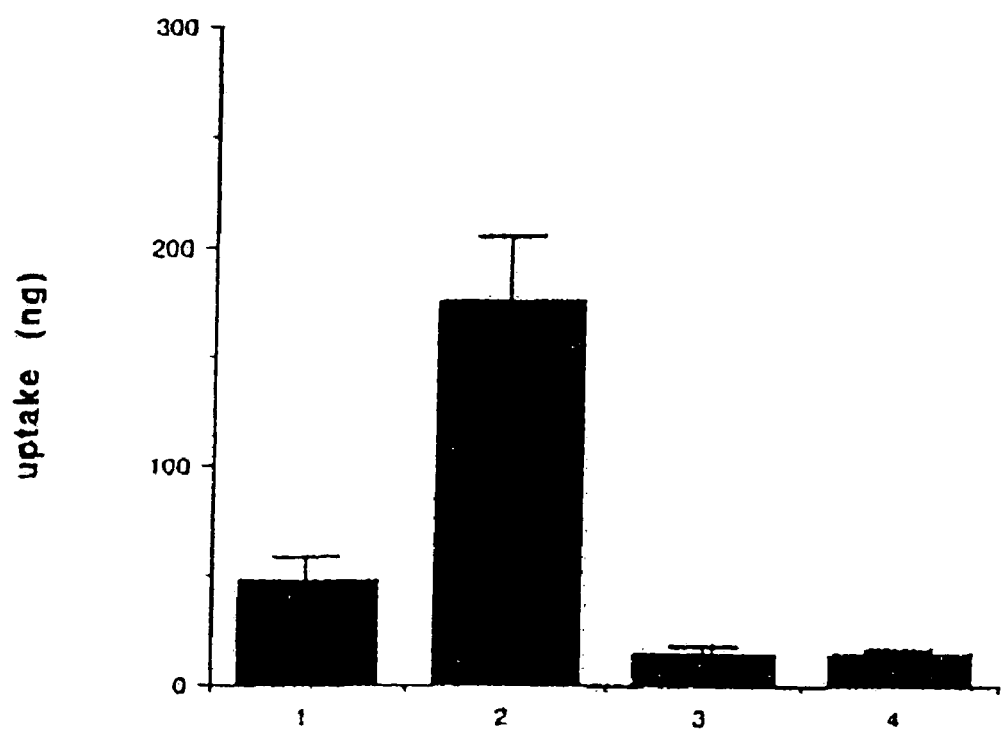
FIG. 24 shows the association of PEG/A-fMLF4-DIG4 and PEG/A-DIG4 with cells.

Targeting drugs to cells. In order to directly show the accumulation of PEG/A-drug-ligand conjugates, PEG/A-fMLF4-DIG4 (333 nM) was incubated with differentiated HL-60 cells. The DIG ELISA demonstrated that 18% of this conjugate had been bound and/or internalized by these macrophage-like cells (FIG. 24). When the negative control conjugate, PEG/A-DIG$_8$, was incubated with HL-60 cells, 4.7% uptake was observed. This much lower accumulation in the absence of fMLF confirmed the importance of this ligand in the interaction of conjugates with macrophage-like cells. Lymphocytic Jurkat cells, which do not express the fMLF receptor, accumulated both PEG/A-DIG$_8$ (1.5%) and PEG/A-fMLF4-DIG4 (1.3%) to a much lesser extent (FIG. 24). These values represent nonspecific cellular binding of polymers. These results indicate the specificity of binding of PEG/A-fMLF4-DIG4 to HL-60 cells. The 4.7% accumulation of PEG/A-DIG4 by HL-60 cells might reflect the tendency of these macrophage-like cells to bind and phagocytose polymeric PEG/A molecules non-specifically.

Figure 15:
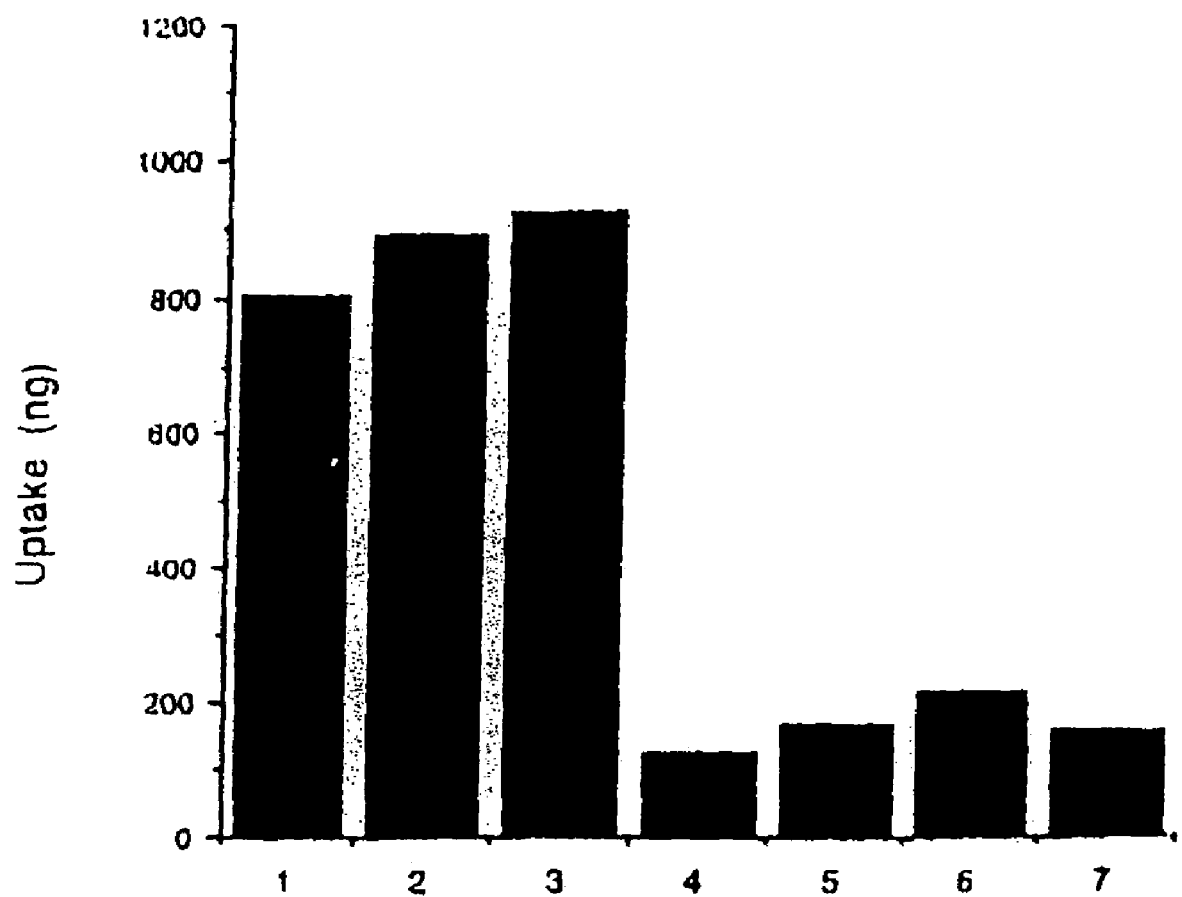
FIG. 15 depicts specific targeting of peritoneal macrophages by fMLF.

Injection of PEG/A-fMLF$_4$-DIG$_4$ into the peritoneal cavity of BALB/c mice was used to determine the in vivo properties of this conjugate, in contrast to using the differentiated HL-60 cell line. The mice in this study were not injected with thioglycol, and, therefore, the macrophages in the peritoneal cavity were not activated. These non-activated peritoneal cells accumulated DIG to about a 5-fold greater extent from the targeted conjugate, PEG/A-fMLF$_4$-DIG$_4$, than from the non-targeted conjugate, PEG/A-DIG$_8$ (FIG. 15). In fact, 17% of the administered PEG/A-fMLF$_4$-DIG$_4$ was taken up by peritoneal cells, whereas they accumulated only 3.3% of the non-targeted PEG/A-DIG$_8$. This low level of accumulation of non-targeted DIG is not surprising, since we have shown that in culture there is some nonspecific binding of PEG/A to promyelocytic HL-60 cells (FIG. 24). Peritoneal incubation for less than 1 h (15 or 30 min) gave similar results. It should be noted that the DIG that was accumulated in cells is expected to remain conjugated to its PEG/A carrier, but this was not confirmed.

These results demonstrate the ability of multiple fMLF moieties to target a polymeric drug delivery molecule (Huang et al., 1998) to phagocytic cells. Such phagocytic cells populate the reticuloendothelial system and play a key role in host defense against bacteria (Seifert and Schultz, 1991). Macrophages recognize bacteria through a specific receptor for peptides containing N-formyl methionine, which is the initiating amino acid in prokaryote protein synthesis. The high affinity formyl methionine receptor (referred to here as the fMLF receptor) is a member of the G-protein coupled receptor family (Gierschik et al., 1991; Prossnitz and Ye, 1997; Le et al., 2001). The binding of fMLF to this receptor initiates a series of cascades, resulting in chemotaxis (Martinet et al., 1994) and cellular activation (Montero et al., 1994). Since this receptor is present on phagocytic cells, such as macrophages and neutrophils (Niedel et al., 1980), it could serve as a targeting ligand for delivering drugs to these cells.

This approach to drug delivery is based on the use a PEG-based carrier with multiple attachment sites to which drugs or targeting moieties can be linked (Huang et al., 1998). By appending drugs via the bioreversible disulfide bond, that can be designed to varying degrees of susceptibility to cleavage by reducing agents (Huang et al., 1998), the circulating time of the carrier can be adjusted, allowing it to reach the targeted cells, before releasing its drug cargo. The multiple attachment sites on the PEG-based carrier can not only provide a high payload of drug, but also can be used for appending one or more moieties for targeting specific cellular receptors or promoting cell uptake of the conjugate. In this study, the enhancement in avidity for the targeted receptor on phagocytic cells by multivalent binding of the fMLF ligand is demonstrated. Thus, a concentration of only 0.18 nM B8-PEG-fMLF4 is needed to get 50% occupancy of the macrophage cell surface fMLF receptors, as opposed to 190 nM for B8-PEG-fMLF1.1, with only one appended ligand, an increase in avidity of more than 1000-fold (Table 1).

After binding of the free fMLF chemotactic peptide to a phagocytic cell, a rapid receptor-mediated internalization takes place (Niedel et al., 1979). Our results show that polymers with multiple fMLF moieties are capable of binding to and/or entering cells in culture and in vivo. In the present study we have not fully defined the possible mechanism of internalization, and have only used the model indicator compound digoxigenin stably linked by an amide bond to the carrier polymer rather than an actual therapeutic or diagnostic agent. Some of our results (FIGS. 24 and 25) do not distinguish between binding and internalization.

A potential cause of adverse effects of targeting fMLF receptors on phagocytes is cellular activation caused by this interaction. Cellular activation is mediated by a complex chain of signal transduction events (reviewed by Prossnitz and Ye, 1997), and can be monitored by the mobilization of calcium from intracellular stores (Camps et al., 1992). This transient increase in intracellular free calcium correlates with acidification and stimulation of superoxide ($O_2$—) release. The level of free fMLF required for half maximal effect on $Ca^{2+}$ release has been reported to be 2-4 nM (Wenzel-Seifert and Seifert, 1990), in agreement with the determination of 5 nM herein, while the EC50 for superoxide production has been reported to be 15-30 nM fMLF (Klinker et al., 1996). In this study all conjugates with four or more copies of fMLF and free fMLF displayed an EC50 value of about 5 nM for calcium release (Table 1 and FIG. 23). Therefore, the cooperative effect that was observed in binding is less pronounced for cellular activation. This difference indicates that polymers targeted to phagocytic cells with multiple fMLF moieties should be much more potent as targeting agents than as cellular activators. At a concentration of 1 nM B8-PEG-fMLF8, nearly 100% of the fMLF receptors were occupied by the targeted drug carrier, whereas little or no cellular activation occurred.

PEG based copolymers have been found to be biocompatible and are currently being developed for multiple in vivo applications. (Poiani et al., 1994). These include the use of biotin targeting moieties to promote sodium-dependent multivitamin transporter (SMVT) mediated transport of molecules across the intestinal epithelium (see previous examples). In the present study, the high molecular weight (>20 KDa) and inertness of PEG-based conjugate would be expected to confer on appended drugs an extended in vivo half-life and protection from degradative processes and immune system surveillance (Davis et al., 1981). Therefore, we show that a PEG-based carrier containing multiple copies of fMLF can be used to target drugs to macrophages and other phagocytic cells without the adverse effects of activation of these cells. Furthermore, the relative lack of enhancement of cellular activation by polymers carrying multiple targeting fMLF groups might indicate that drugs appended to such polymers would be less likely to be inactivated by the many degradative mechanisms induced by phagocyte activation.

The present invention is not to be limited in scope by the specific embodiments describe herein. Indeed, various modifications of the invention in addition to those described herein will become apparent to those skilled in the art from the foregoing description and the accompanying figures. Such modifications are intended to fall within the scope of the appended claims.

It is further to be understood that all base sizes or amino acid sizes, and all molecular weight or molecular mass values, given for nucleic acids or polypeptides are approximate, and are provided for description.

Various publications are cited herein, the disclosures of which are incorporated herein by reference in their entireties.

Anderson, R., and Mahomed Goolam, A. (1997) Calcium efflux and influx in f-met-leu-phe (fMLP)-activated human neutrophils are chronologically distinct events. Clin. Exp. Immunol. 110, 132-138.

Azuma, E. K., Yuo, A, Matsushima, K., Kasahara, T., Mizoguchi, H., Saito, M., Takaku, F., and Kitagawa, S. (1996) Activation and priming of human monocytes by monocyte chemotactic and activating factor: Cooperation with other inflammatory cytokines and close association between an increase in cytoplasmic free Ca2+ and intracellular acidification. Exp. Hematol. 24, 169-175.

Benelli, R., Mortarini, R., Anichini, A., Giunciuglio D., Noonan D. M., Monatalti, S., Tacchetti, C., and Albini, A. (1998) Monocyte-derived dendritic cells and monocytes migrate to HIV-Tat RGD and basic peptides. AIDS 12, 261-268.

Camps, M., Carozzi, A., Schnabel, P., Scheer, A., Parker, P. J., and Gierschik, P. (1992) Lysosome-selective stimulation of phospholipase C-b2 by G-protein-bg-subunits. Nature 369, 684-686.

Collins, S. J. (1987) The HL-60 promyelocytic leukemia cell line: Proliferation, differentiation, and cellular oncogene expression. Blood 70, 1233-1244.

Dahlgren, C., Anderson, T., and Stendahl, O. (1987) Chemotactic factor binding and functional capacity: A comparison between human granulocytes and differentiated HL-60 cells. J. Leukocyte Biol. 42, 245-252.

Davis, S., Abuchowiski, A., Park, Y. K., and Davis, F. E. (1981) Alteration of the circulating half life and antigenic properties of bovine adenosine deaminase in mice by attachment of polyethylene glycol. Clin. Exp. Immunol. 46, 649-652.

Derian, C. K., Solomon, H. F., Higgins, J. D. III, Beblavy M. J., Santulli, R. J., Bridger, G. J., Pike, M. C., Kroon, D. J., and Fischman, A. J. (1996) Selective inhibition of N-formylpeptide-induced neutrophil activation by carbamate-modified peptide analogues. Biochemistry 35, 1265-1269.

Gierschik, P., Moghtader, R., Straub, C., Dietrich, K., and Jacobs, K. H. (1991) Signal amplification in HL-60 granulocytes. Evidence that the chemotactic peptide receptor catalytically activates guanine-nucleotide-binding regulatory proteins in native plasma membranes. Eur. J. Biochem. 197, 725-732.

Huang, S.-Y., Pooyan, S., Wang, J., Choudhury, I., Leibowitz, M. J., and Stein, S. (1998) A polyethylene glycol copolymer for carrying and releasing multiple copies of cysteine-containing peptides. Bioconj. Chemistry 9, 612-617

Klinker, J. F., Wenzel-Seifert, K., and Seifert, R. (1996) G-Protein-coupled receptors in HL-60 human leukemia cells. Gen. Pharmacol. 27, 33-54.

Le, Y., Oppenheim, J. J., and Wang, J. M. (2001) Pleiotropic roles of formyl peptide receptors. Cytokine Growth Factor Revs. 12, 91-105.

Lees, W. J., Spaltenstein, A., Kingery-Wood, J. E., and Whitesides, G. M. (1994) Polyacrylamides bearing pendant alpha-sialoside groups strongly inhibit agglutination of erythrocytes by influenza A virus: Multivalency and Steric stabilization of particulate biological systems. J. Med. Chem. 37, 3419-3433.

Lobenberg, R., and Kreuter, J. (1996) Macrophage targeting of azidothymidine: a promising strategy for AIDS therapy. AIDS Res. and Human Retrovirol. 12, 1709-1715.

Mankertz, J. Matthes, E. Rokos, K. Von Baeyer, H. Pauli, G., and Riedel, E. (1996) Selective endocytosis of fluorothymidine and azidothymidine coupled to LDL into HIV infected mononuclear cells. Biochim. Biophys. Acta 1317, 233-237

Martinet, Y., Martinet, N., Vignaud, J. D., and Plenat, F. (1994) Blood monocytes chemotaxis. J. Immunol. Methods. 174, 209-214.

Medda, S. Das, N. Mahato, S. B., Mahadaven, P. R., and Basu, M. K. (1995) Glycoside-bearing liposome delivery systems against macrophage-associated disorders involving *Mycobacterium leprea* and *Mycobacterium tuberculosis*. Indian J. Biochem. Biophys. 32, 147-151

Mistry, P. K., Wraight, E. P., and Cox, T. M. (1996) Therapeutic delivery of proteins to macrophages: implications for treatment of Gaucher's disease. Lancet 348, 1555-1559.

Montero, M., Garcia-Sancho, J., and Alvarez, J. (1994) Activation by chemotactic peptide of a receptor-operated Ca2+ entry pathway in differentiated HL60 cells. J. Biol. Chem. 269, 29451-29456.

Niedel, J. E., Kahane, I., and Cuatrecasas, P. (1979) Receptor-mediated internalization of fluorescent chemotactic peptide by human neutrophils. Science. 205, 1412-1414.

Niedel, J., Kahane, I., Lachman, L., and Cuatrecasas, P. (1980) A subpopulation of culture d human promyelocytic leukemia cells (HL-60) displays the formyl peptide chemotactic receptor. Proc. Natl. Acad. Sci. USA 77, 1000-1004.

Poiani, G. J. Riley, D. J., Fox, J. D., Kemnitzer, J. E., Gean, K. F., and Kohn, J. (1994) Conjugation of cis-4-hydroxy-L-proline and poly(PEG-Lys), a water soluble poly(ether urethane): Synthesis and evaluation of antifibrotic effect in vitro and in vivo. Bioconj. Chem. 5, 621-630.

Prossnitz, E. R., Quechenberger, O., Cochrane, C. G., and Ye, R. D. (1993) Signal transducing properties of the N-formyl peptide receptor expressed in undifferentiated HL60 cells. J. Immunol. 151, 5704-5715.

Prossnitz, E. R., and Ye, R. D. (1997) The N-formyl peptide receptor: A model for the study of chemoattractant receptor structure and function. Pharmacol. Ther. 74, 73-102.

Randolph, G. J., Beaulieu, S., Lebecque, S., Steinman, R. M., and Muller, W. A. (1998) Differentiation of monocytes into dendritic cells in a model of transendothelial trafficking. Science 282, 480-483.

Ramanathan, S., Pooyan, S., Stein, S., Wang, J., Leibowitz, M. J., and Sinko, P. J. (2001) Targeting the sodium-dependent multivitamin transporter (SMVT) for improving the oral absorption properties of larger peptides. Pharmaceut. Res. In press.

Rossi, L. Brandi G., Schiavano G. F., Balestra, E., Millo, E., Scarfi, S., Damonte, G., Gasparini, A., Magnani, M. Perno, C. F., Benatti, U., and De Flora, A. (1998) Macrophage protection against human immunodeficiency virus or herpes simplex virus by red blood cell-mediated delivery of a heterodinucleotide of aziothymidine and acyclovir. AIDS Res. and Human Retrovirol. 14,435-444.

Seifert R., and Schultz, G. (1991) The superoxide-forming NADPH oxidase of phagocytes: an enzyme regulated by multiple mechanisms. Rev. Physiol. Biochem. Pharmacol. 117, 1-338.

Seifert, R., Serke, S., Huhn, D., Bessler, W. G., Hauschildt S., Metzegae, J., Wiesmuller, K.-H., and Jung, G. (1992) Incomplete functional differentiation of HL-60 leukemic cells by synthetic lipopropeptides. Partial inhibition by pertussis toxin of enhanced superoxide formation. Eur. J. Biochem. 203, 143-151.

Sigal, G. B., Mammen, M., Dahmann, G., and Whitesides, G. M. (1996) Polyacrylamides bearing pendant-sialoside groups strongly inhibit agglutination of erythrocytes by influenza virus: The strong inhibition reflects enhanced binding through cooperative polyvalent interactions. J. Amer. Chem. Soc. 11b, 3789-3800.

Udenfriend, S., Stein, S., Bohlen, P., and Dairman, W. (1972) Fluorescamine, a new reagent for assay of amino acids, peptides, proteins and other primary amines in the picomole range. Science 178, 871.

Venier-Julienne, M. C., Vouldoukis, I., Monjour, L., and Benoit, J. P. (1995) In vitro study of the anti-leishmanial activity of biodegradable nanoparticles. J. Drug Targeting 3, 23-29.

Wenzel-Seifert, K., and Seifert, R. (1990) Nucleotide-, chemotactic peptide- and phorbal ester induced exocytosis in HL-60 leukemic cells. Immunobiol. 181, 298-316.

What is claimed:

1. A transcompartmental delivery promoting composition comprising:
   a) a branched PEG having multiple arms, each having a functional group, at least one peptide selected from the group consisting of SEQ ID NOS: 1-8 independently covalently bound to one of said arms, and at least one cell uptake promoter consisting of formyl-methionyl-leucyl phenylalanine (fMLF) covalently bound to said peptide selected from the group consisting of SEQ ID NOS: 1-8;
   or
   b) a branched PEG having multiple arms, each having a functional group, at least one cell uptake promoter consisting of formyl-methionyl-leucyl phenylalanine (fMLF) independently covalently bound to one of said arms; and at least one peptide selected from the group consisting of SEQ ID NOS: 1-8 independently covalently bound to one of said arms.

2. The composition of claim 1, wherein the polymer is a branched PEG having at least 3 arms comprising a functional group.

3. The composition of claim 1, wherein the polymer is a branched PEG having at least 4 arms comprising a functional group.

4. The composition of claim 1, wherein the polymer is a branched PEG having 8 arms comprising a functional group.

5. The composition of claim 4, wherein the polymer is a branched PEG having 8 arms comprising a functional group, and an fMLF is attached to at least two of the arms.

6. The composition of claim 4, wherein the polymer is a branched PEG having 8 arms comprising a functional group, and fMLF is attached to four of the arms.

7. The composition of claim 1, wherein at least two peptides selected from the group consisting of SEQ ID NOS: 1-8 are independently bound to a functional group of an arm of the branched PEG.

8. The composition of claim 1, consisting of a PEG having 8 arms, at least two fMLF moieties independently covalently bound to one of the functional groups of a PEG arm, and a peptide selected from the group consisting of SEQ ID NOS: 1-8 covalently bound to at least one of the functional groups of an arm of the branched PEG.

9. The composition of claim 1, consisting of a PEG having 8 arms, at least four fMLF moieties independently covalently bound to one of the functional groups of a PEG arm, and a at least one of the peptides selected from the group consisting of SEQ ID NOS: 1-8 are independently covalently bound to a functional group of an arm of the branched PEG.

10. The composition of claim 1, wherein four peptides selected from the group consisting of SEQ ID NOS: 1-8 are independently covalently bound to a functional group of an arm of the branched PEG.

11. The composition of claim 1, wherein the branched PEG size is about 20 kDa.

* * * * *

SEQUENCE LISTING

```
<160> NUMBER OF SEQ ID NOS: 12

<210> SEQ ID NO 1
<211> LENGTH: 11
<212> TYPE: PRT
<213> ORGANISM: Artificial Sequence
<220> FEATURE:
<223> OTHER INFORMATION: synthetic
<220> FEATURE:
<221> NAME/KEY: VARIANT
<222> LOCATION: 10
<223> OTHER INFORMATION: Xaa = Any Amino Acid

<400> SEQUENCE: 1

Arg Lys Lys Arg Arg Gln Arg Arg Arg Xaa Cys
1               5                   10

<210> SEQ ID NO 2
<211> LENGTH: 11
<212> TYPE: PRT
<213> ORGANISM: Artificial Sequence
<220> FEATURE:
<223> OTHER INFORMATION: synthetic

<400> SEQUENCE: 2

Arg Lys Lys Arg Arg Gln Arg Arg Arg Cys Cys
1               5                   10

<210> SEQ ID NO 3
<211> LENGTH: 11
<212> TYPE: PRT
<213> ORGANISM: Artificial Sequence
<220> FEATURE:
<223> OTHER INFORMATION: synthetic

<400> SEQUENCE: 3

Arg Lys Lys Arg Arg Gln Arg Arg Arg Lys Cys
1               5                   10

<210> SEQ ID NO 4
<211> LENGTH: 11
<212> TYPE: PRT
<213> ORGANISM: Artificial Sequence
<220> FEATURE:
<223> OTHER INFORMATION: synthetic

<400> SEQUENCE: 4

Arg Lys Lys Arg Arg Gln Arg Arg Arg Cys Cys
1               5                   10
```

```
<210> SEQ ID NO 5
<211> LENGTH: 11
<212> TYPE: PRT
<213> ORGANISM: Artificial Sequence
<220> FEATURE:
<223> OTHER INFORMATION: synthetic

<400> SEQUENCE: 5

Arg Lys Lys Arg Arg Gln Arg Arg Arg Lys Cys
 1               5                  10

<210> SEQ ID NO 6
<211> LENGTH: 11
<212> TYPE: PRT
<213> ORGANISM: Artificial Sequence
<220> FEATURE:
<223> OTHER INFORMATION: synthetic

<400> SEQUENCE: 6

Gln Lys Lys Arg Arg Gln Arg Arg Arg Lys Cys
 1               5                  10

<210> SEQ ID NO 7
<211> LENGTH: 11
<212> TYPE: PRT
<213> ORGANISM: Artificial Sequence
<220> FEATURE:
<223> OTHER INFORMATION: synthetic

<400> SEQUENCE: 7

Arg Lys Lys Arg Arg Pro Arg Arg Arg Cys Cys
 1               5                  10

<210> SEQ ID NO 8
<211> LENGTH: 11
<212> TYPE: PRT
<213> ORGANISM: Artificial Sequence
<220> FEATURE:
<223> OTHER INFORMATION: synthetic

<400> SEQUENCE: 8

Cys Lys Arg Arg Arg Gln Arg Arg Lys Lys Arg
 1               5                  10

<210> SEQ ID NO 9
<211> LENGTH: 10
<212> TYPE: PRT
<213> ORGANISM: Artificial Sequence
<220> FEATURE:
<223> OTHER INFORMATION: synthetic

<400> SEQUENCE: 9

Lys Arg Arg Arg Gln Arg Arg Lys Lys Arg
 1               5                  10

<210> SEQ ID NO 10
<211> LENGTH: 21
<212> TYPE: DNA
<213> ORGANISM: Artificial Sequence
<220> FEATURE:
<223> OTHER INFORMATION: primer

<400> SEQUENCE: 10
ctgtccgtgc tggccctggg c                                        21

<210> SEQ ID NO 11
```

```
-continued

<211> LENGTH: 21
<212> TYPE: DNA
<213> ORGANISM: Artificial Sequence
<220> FEATURE:
<223> OTHER INFORMATION: primer

<400> SEQUENCE: 11
gaccaggcca atgaggcagc c                                              21

<210> SEQ ID NO 12
<211> LENGTH: 4
<212> TYPE: PRT
<213> ORGANISM: Artificial Sequence
<220> FEATURE:
<223> OTHER INFORMATION: synthetic

<400> SEQUENCE: 12

Lys Cys Cys Cys
  1
```